United States Patent
Melander et al.

(10) Patent No.: US 11,582,970 B2
(45) Date of Patent: Feb. 21, 2023

(54) 2-AMINOIMIDAZOLE-PHENYL DERIVATIVES USEFUL FOR CONTROLLING MICROBIAL GROWTH

(71) Applicant: NORTH CAROLINA STATE UNIVERSITY, Raleigh, NC (US)

(72) Inventors: Christian Melander, Raleigh, NC (US); David Kendall Jung, Durham, NC (US); Samuel Onofre Reyes, Cary, NC (US)

(73) Assignee: North Carolina State University, Raleigh, NC (US)

( * ) Notice: Subject to any disclaimer, the term of this patent is extended or adjusted under 35 U.S.C. 154(b) by 91 days.

(21) Appl. No.: 16/492,722

(22) PCT Filed: Mar. 8, 2018

(86) PCT No.: PCT/US2018/021474
§ 371 (c)(1),
(2) Date: Sep. 10, 2019

(87) PCT Pub. No.: WO2018/169752
PCT Pub. Date: Sep. 20, 2018

(65) Prior Publication Data
US 2022/0000118 A1    Jan. 6, 2022

Related U.S. Application Data

(60) Provisional application No. 62/471,464, filed on Mar. 15, 2017.

(51) Int. Cl.
| | | |
|---|---|---|
| *A01N 47/30* | (2006.01) | |
| *A61P 31/04* | (2006.01) | |
| *A01P 1/00* | (2006.01) | |
| *A01N 47/32* | (2006.01) | |
| *A01N 47/36* | (2006.01) | |
| *A61K 31/4168* | (2006.01) | |
| *A61K 31/4178* | (2006.01) | |
| *A61K 31/4184* | (2006.01) | |
| *A61K 31/4439* | (2006.01) | |
| *A61K 31/5377* | (2006.01) | |
| *A61L 2/232* | (2006.01) | |
| *C07D 233/88* | (2006.01) | |
| *C07D 235/30* | (2006.01) | |
| *C07D 401/12* | (2006.01) | |
| *C07D 403/12* | (2006.01) | |
| *C07D 405/12* | (2006.01) | |
| *C07D 409/12* | (2006.01) | |
| *C09D 5/14* | (2006.01) | |

(52) U.S. Cl.
CPC .......... *A01N 47/30* (2013.01); *A01N 47/32* (2013.01); *A01N 47/36* (2013.01); *A01P 1/00* (2021.08); *A61K 31/4168* (2013.01); *A61K 31/4178* (2013.01); *A61K 31/4184* (2013.01); *A61K 31/4439* (2013.01); *A61K 31/5377* (2013.01); *A61L 2/232* (2013.01); *A61P 31/04* (2018.01); *C07D 233/88* (2013.01); *C07D 235/30* (2013.01); *C07D 401/12* (2013.01); *C07D 403/12* (2013.01); *C07D 405/12* (2013.01); *C07D 409/12* (2013.01); *C09D 5/14* (2013.01); *A61L 2202/24* (2013.01)

(58) Field of Classification Search
None
See application file for complete search history.

(56) References Cited

U.S. PATENT DOCUMENTS

| | | | |
|---|---|---|---|
| 7,897,631 B2 | 3/2011 | Melander et al. | |
| 7,906,544 B2 | 3/2011 | Melander et al. | |
| 8,840,912 B2 | 9/2014 | Melander et al. | |
| 9,005,643 B2* | 4/2015 | Melander .......... | A61K 31/4168 514/397 |
| 9,295,257 B2 | 3/2016 | Melander et al. | |
| 2009/0270475 A1 | 10/2009 | Melander et al. | |
| 2014/0221374 A1* | 8/2014 | Vernier ................ | C07D 417/14 544/122 |
| 2015/0183746 A1 | 7/2015 | Melander et al. | |

(Continued)

FOREIGN PATENT DOCUMENTS

WO    2009/145829    12/2009

OTHER PUBLICATIONS

Vo, D. et al., ACS Chemical Biology 2014 vol. 9, pp. 711-721.*

(Continued)

*Primary Examiner* — Daniel R Carcanague
(74) *Attorney, Agent, or Firm* — Myers Bigel, P.A.

(57) ABSTRACT

Provided are 2-aminoimidazole-phenyl derivative compounds of Formula (I): which compounds are useful in methods of controlling microbial growth, such as by enhancing the effects of an antibiotic administered in combination with the compound. Compositions including these compounds, devices including these compounds, and methods of using the same are also provided.

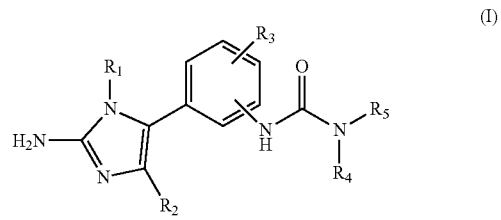

(I)

49 Claims, No Drawings

(56) References Cited

U.S. PATENT DOCUMENTS

2015/0183770 A1 7/2015 Amberg et al.
2022/0125763 A1* 4/2022 Jung ..................... A61K 38/12

OTHER PUBLICATIONS

International Search Report and Written Opinion corresponding to PCT/US2018/021474 (dated May 8, 2018) (7 pages).
Musk et al. "Chemical Countermeasures for the Control of Bacterial Biofilms: Effective Compounds and Promising Targets" Current Medicinal Chemistry, 13(18):2163-2177 (2006).
Donlan et al. "Biofilms: Survival Mechanisms of Clinically Relevant Microorganisms" Clinical Microbiology Reviews, 15(2):167-193 (2002).
Rasmussen et al. "Quorum-sensing inhibitors as anti-pathogenic drugs" International Journal of Medical Microbiology, 296(2-3):149-161 (2006) (Abstract only).
Geske et al. "Small Molecule Inhibitors of Bacterial Quorum Sensing and Biofilm Formation" Journal of the American Chemical Society, 127(37):12750-13080 (2005) (Abstract only).
Dong et al. "Quorum Sensing and Quorum-Quenching Enzymes" The Journal of Microbiology, 43(S):101-109 (2005).
Nealson et al. "Cellular Control of the Synthesis and Activity of the Bacterial Luminescent System" Journal of Bacteriology, 104(1):313-322 (1970).
Hentzer et al. "Inhibition of quorum sensing in Pseudomonas aeruginosa biofilm bacteria by a halogenated furanone compound" Microbiology-Sgm, 148:87-102 (2002).
Hu et al. "Bacterial Biofilm Inhibitors from Diospyros dendo" Journal of Natural Products, 69(1):118-120 (2006) (Abstract only).
Chinese Office Action corresponding to CN 201880032076.9; dated Jan. 5, 2021 (19 pages, including English translation).
Bunders et al. "Identification of aryl 2-aminoimidazoles as biofilm inhibitors in Gram-negative bacteria" Bioorganic & Medicinal Chemistry Letters, 20(12): 3797-3800 (2010).
Extended European Search Report corresponding to EP 18767442.9; dated Aug. 6, 2020 (10 pages).
Panmanee et al. "High-Throughput Screening for Small-Molecule Inhibitors of *Staphylococcus epidermidis* RP62a Biofilms" Journal of Biomolecular Screening, 18(7): 820-829 (2013).
Russian Office Action corresponding to RU2019132671; dated Jul. 5, 2021 (17 pages, including English translation).
First Japanese Office Action corresponding to JP 2019-572349; dated Feb. 22, 2022 (11 pages, including English translation).
Milton, Morgan E., et al., "Re-sensitizing Multidrug Resistant Bacteria to Antibiotics by Targeting Bacterial Response Regulators: Characterization and Comparison of Interactions between 2-Aminoimidazoles and the Response Regulators BfmR from Acinetobacter baumannii and QseB from Fra", Frontiers in molecular biosciences, 5 (Article 15), 2018, 1-12.

* cited by examiner

2-AMINOIMIDAZOLE-PHENYL DERIVATIVES USEFUL FOR CONTROLLING MICROBIAL GROWTH

CROSS REFERENCE TO RELATED APPLICATIONS

This application is a 35 U.S.C. § 371 national phase application of International Application Serial No. PCT/US2018/021474, filed Mar. 8, 2018, which claims the benefit of U.S. provisional patent application Ser. No. 62/471,464, filed Mar. 15, 2017, the disclosure of which is incorporated by reference herein in its entirety.

STATEMENT OF GOVERNMENT SUPPORT

This invention was made with Government support under grant number HHSN272201500010C awarded by the National Institutes of Health. The U.S. Government has certain rights to this invention.

BACKGROUND

Biofilms are complex communities of microorganisms that are commonly found on a variety of substrates or surfaces that are moist or submerged (Musk et al., *Curr. Med. Chem.*, 2006, 13, 2163; Donlan et al., *Clin. Microbiol. Rev.*, 2002, 15, 167). Though primarily populated by bacteria, biofilms can also contain many different individual types of microorganisms, e.g., bacteria, archaea, protozoa and algae. The formation of biofilms can be thought of as a developmental process in which a few free-swimming (planktonic) bacteria adhere to a solid surface and, in response to appropriate signals, initiate the formation of a complex sessile microcolony existing as a community of bacteria and other organisms. Bacteria within biofilms are usually embedded within a matrix, which can consist of protein, polysaccharide, nucleic acids, or combinations of these macromolecules. The matrix is a critical feature of the biofilm that protects the inhabiting organisms from antiseptics, microbicides, and host cells. It has been estimated that bacteria within biofilms are upwards of 1,000-fold more resistant to conventional antibiotics (Rasmussen et al., *Int. J Med. Microbiol.*, 2006, 296, 149).

Biofilms play a significant role in infectious disease. It is estimated that biofilms account for between 50-80% of microbial infections in the body, and that the cost of these infections exceeds $1 billion annually. For example, persistent infections of indwelling medical devices remain a serious problem for patients, because eradication of these infections is virtually impossible. A few diseases in which biofilms have been implicated include endocarditis, otitis media, chronic prostatitis, periodontal disease, chronic urinary tract infections, and cystic fibrosis. The persistence of biofilm populations is linked to their inherent insensitivity to antiseptics, antibiotics, and other antimicrobial compounds or host cells.

Deleterious effects of biofilms are also found in non-medical settings. For example, biofilms are a major problem in the shipping industry. Biofilms form on and promote the corrosion of ship hulls and also increase the roughness of the hulls, increasing the drag on the ships and thereby increasing fuel costs.

Given the breadth of detrimental effects caused by bacterial biofilms, there has been an effort to develop small molecules that will inhibit their formation (Musk et al., *Curr. Med. Chem.*, 2006, 13, 2163). The underlying principle is that if bacteria can be maintained in the planktonic state, they will either not attach to a target surface and/or they can be killed by a lower dose of microbicide.

Despite the extent of biofilm-driven problems, examples of structural scaffolds that inhibit biofilm formation are rare (Musk et al., *Curr. Med. Chem.*, 2006, 13, 2163). The few known examples include the homoserine lactones (Geske et al., *J. Am. Chem. Soc.*, 2005, 127, 12762), which are naturally-occurring bacterial signaling molecules that bacteria use in quorum sensing (Dong et al., *J. Microbiol.*, 2005, 43, 101; Nealson et al., *J. Bacteriol.*, 1970, 104, 313), brominated furanones isolated from the macroalga *Delisea pulchra* (Hentzer et al., *Microbiology-Sgm*, 2002, 148, 87), and ursene triterpenes from the plant *Diospyros dendo* (Hu et al., *J. Nat. Prod.*, 2006, 69, 118).

More recently, 2-amino imidazole derivatives with activity in inhibiting biofilms and/or controlling microbial growth have been explored. See, e.g., Melander et al., U.S. Pat. Nos. 7,906,544, 7,897,631, 8,840,912, 9,005,643, 9,295,257.

Bacteria have an unparalleled ability to overcome foreign chemical insult. For example, resistance to vancomycin, "the antibiotic of last resort," has become more prevalent, and strains of vancomycin-resistant *Staphylococcus aureus* have become a serious health risk. It has been predicted that it is simply a matter of time before different bacterial strains develop vancomycin resistance, and the safety net that vancomycin has provided for decades in antibiotic therapy will no longer be available.

Therefore, the identification of chemical architectures useful to inhibit biofilm development and/or control microbial growth is needed, and especially those that may enhance the effectiveness of antibiotics.

SUMMARY

Active compounds are provided herein, which compounds are useful, e.g., as antibiotic adjuvants in the control of bacterial growth. Included are compounds of Formula (I):

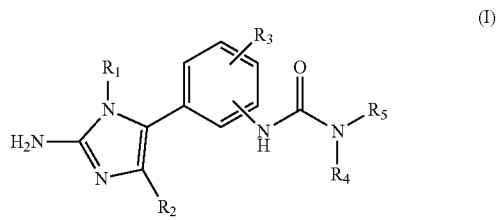

wherein:

$R_1$ is selected from the group consisting of H and alkyl (e.g., lower alkyl);

$R_2$ is selected from the group consisting of H, alkyl (e.g., lower alkyl), aryl, and heteroaryl;

$R_3$ is selected from the group consisting of H, halo and alkoxy;

or $R_2$ and $R_3$ together form a fused ring; and $R_4$ and $R_5$ are each independently selected from the group consisting of alkyl, aryl, cycloalkyl, heterocyclo, and heteroaryl, or a pharmaceutically acceptable salt or prodrug thereof.

In some embodiments, the compounds are compounds of Formula (I)(a):

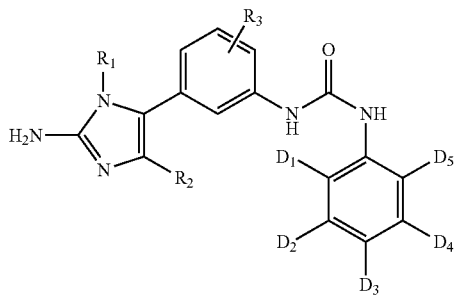
(I)(a)

wherein:

R₁, R₂ and R₃ are as defined above, and $D_1$, $D_2$, $D_3$, $D_4$, and $D_5$ are each independently selected from the group consisting of H, halo, alkyl (e.g., lower alkyl), acyl, alkoxy (e.g., methoxy or ethoxy), aryl, heteroaryl, amino, amide, nitro, hydroxyl, thiol, sulfone, sulfoxide, nitrile, nitro, and haloalkyl (e.g., fluoroalkyl such as trifluoromethyl (—CF₃)), or wherein $D_1$ and $D_2$, $D_2$ and $D_3$, $D_3$ and $D_4$, or $D_4$ and $D_5$ together form a fused ring (e.g., a cyclohexane or cyclohexene fused ring), optionally substituted, or a pharmaceutically acceptable salt or prodrug thereof.

In some embodiments of Formula (I)(a), at least one of $D_1$, $D_2$, $D_3$, $D_4$, and $D_5$ is lower alkyl. In some embodiments, $D_3$ is lower alkyl (e.g., n-propyl, and n-butyl). In some embodiments, $D_3$ is lower alkyl (e.g., n-propyl, and n-butyl), and $D_1$, $D_2$, $D_4$, and $D_5$ are each H. In some embodiments, the compound is a compound of Formula (I)(a)(1):

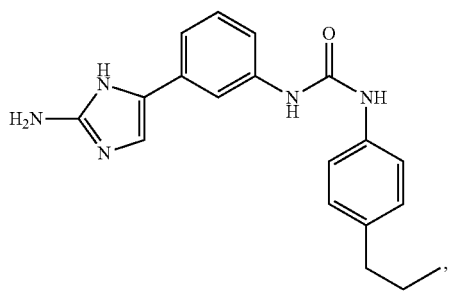
(I)(a)(1)

or a pharmaceutically acceptable salt thereof.

In some embodiments, at least one of $D_1$, $D_2$, $D_3$, $D_4$, and $D_5$ is heteroaryl. In some embodiments, $D_2$ is heteroaryl (e.g., imidazole). In some embodiments of Formula (I)(a), the compound is a compound of Formula (I)(a)(2):

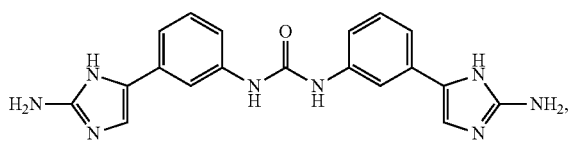
(I)(a)(2)

or a pharmaceutically acceptable salt thereof.

In some embodiments of Formula (I)(a), at least one of $D_1$, $D_2$, $D_3$, $D_4$, and $D_5$ is halo. In some embodiments, $D_2$ and $D_4$ are each halo (e.g., Br). In some embodiments, the compounds are compounds of Formula (I)(a)(3):

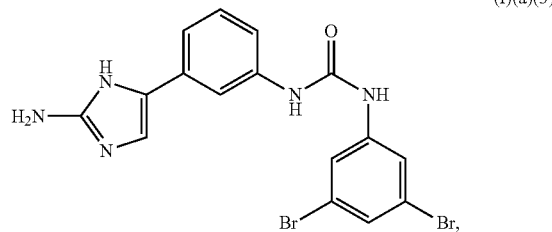
(I)(a)(3)

or a pharmaceutically acceptable salt thereof.

In some embodiments, at least one of $D_1$, $D_2$, $D_3$, $D_4$, and $D_5$ is halo, and at least one of $D_1$, $D_2$, $D_3$, $D_4$, and $D_5$ is haloalkyl. In some embodiments, $D_3$ is fluoro-alkyl (e.g., trifluoromethyl), and $D_4$ is halo (Cl). In some embodiments, $R_2$ is lower alkyl (e.g, methyl, ethyl, and n-propyl). In some embodiments, the compound is a compound of Formula (I)(a)(4):

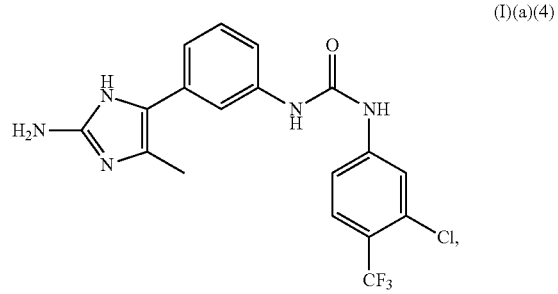 [SMILES: Cc1nc(N)[nH]c1-c1cccc(NC(=O)Nc2ccc(C(F)(F)F)c(Cl)c2)c1]
(I)(a)(4)

or a pharmaceutically acceptable salt thereof.

In some embodiments, the compounds are compounds of Formula (I)(b):

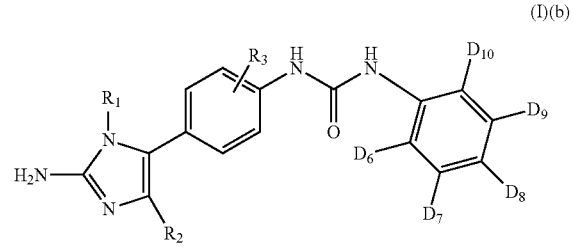
(I)(b)

wherein:

R₁, R₂ and R₃ are as defined above, and $D_6$, $D_7$, $D_8$, $D_9$, and $D_{10}$ are each independently selected from the group consisting of H, halo, alkyl, acyl, alkoxy, aryl, heteroaryl, amino, amide, nitro, hydroxyl, thiol, sulfone, sulfoxide, nitrile, nitro, and haloalkyl (e.g., fluoroalkyl such as trifluoromethyl (—CF₃)), or wherein $D_6$ and $D_7$, $D_7$ and $D_8$, $D_8$ and $D_9$, or $D_9$ and $D_{10}$ together form a fused ring, or a pharmaceutically acceptable salt or prodrug thereof.

In some embodiments of Formula (I)(b), at least one of $D_6$, $D_7$, $D_8$, $D_9$, and $D_{10}$ is heteroaryl. In some embodiments, $D_8$ is heteroaryl (e.g., 2-amino imidazole). In some embodiments, the compound is a compound of Formula (I)(b)(1):

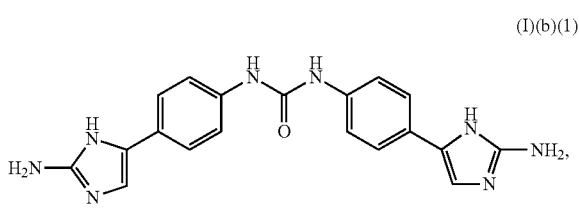 [SMILES: Nc1ncc(-c2ccc(NC(=O)Nc3ccc(-c4cnc(N)[nH]4)cc3)cc2)[nH]1]

or a pharmaceutically acceptable salt thereof.

In some embodiments of Formula (I)(b), $D_8$ and $D_9$ together form a fused ring (e.g., cyclohexane fused ring), optionally substituted. In some embodiments, the compound is a compound of Formula (I)(b)(2):

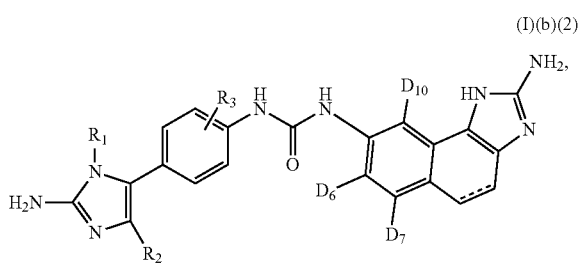

or a pharmaceutically acceptable salt thereof. In some embodiments, the compound is a compound of Formula (I)(b)(3):

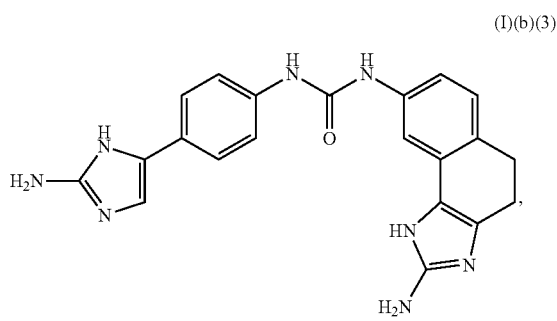 [SMILES: Nc1ncc(-c2ccc(NC(=O)Nc3ccc4c(c3)-c3[nH]c(N)nc3CC4)cc2)[nH]1]

or a pharmaceutically acceptable salt thereof.

Compositions are provided, which include a carrier and an effective amount of a compound disclosed herein. The effective amount of the compound may enhance the effects of an antibiotic that is administered in combination with the compound. Compositions are also provided that include a compound disclosed herein in a carrier (e.g., a pharmaceutically acceptable carrier).

Compositions are further provided that include a compound disclosed herein covalently coupled to a substrate. In some embodiments, the substrate includes a polymeric material. In some embodiments, the substrate includes a solid support. In some embodiments, the substrate includes a drainpipe, glaze ceramic, porcelain, glass, metal, wood, chrome, plastic, vinyl, and Formica® brand laminate (The Diller Corporation, Cincinnati, Ohio). In some embodiments, the substrate includes shower curtains or liners, upholstery, laundry, and carpeting.

Coating compositions are provided, including: (a) a film-forming resin; (b) a solvent that disperses said resin; (c) an effective amount of the compounds or compositions disclosed herein, wherein said effective amount of the compound may enhance the effects of an antibiotic that is administered in combination with the compound; and (d) optionally, at least one pigment. In some embodiments, the compound is covalently coupled to the resin. In some embodiments, the resin includes a polymeric material.

Substrates coated with a coating composition disclosed herein are also provided. In some embodiments, the substrate includes a polymeric material. In some embodiments, the substrate includes a solid support. In some embodiments, the substrate includes a drainpipe, glaze ceramic, porcelain, glass, metal, wood, chrome, plastic, vinyl, and Formica® brand laminate. In some embodiments, the substrate includes shower curtains or liners, upholstery, laundry, and carpeting.

Methods of controlling biofilm formation and/or microbial growth on a substrate are provided, including the step of contacting the substrate with a compound and/or composition disclosed herein, e.g., in an amount effective to enhance the effects of an antibiotic that is administered in combination with the compound, thereby inhibiting biofilm formation and/or bacterial growth. In some embodiments, the substrate may include a drainpipe, glaze ceramic, porcelain, glass, metal, wood, chrome, plastic, vinyl, and Formica® brand laminate. In some embodiments, the biofilm includes Gram-negative bacteria.

Methods for treating a bacterial infection in a subject in need thereof are provided, including administering to said subject a compound and/or composition disclosed herein. In some embodiments, the compound and/or composition is administered in an amount effective to enhance the effects of an antibiotic that is administered in combination with the compound, thereby inhibiting a biofilm component or inhibit growth of said bacterial infection or reduce a bacterial component of the infection. In some embodiments, the bacterial infection is resistant to one or more antibiotics.

Also provided are medical devices, including (a) a medical device substrate; and (b) an effective amount of a compound disclosed herein, either coating the substrate, or incorporated into the substrate, wherein said effective amount of the compound may enhance the effects of an antibiotic that is administered in combination with the compound. In some embodiments, the medical device substrate may include stents, fasteners, ports, catheters, scaffolds and grafts. In some embodiments, the compound is covalently coupled to said substrate.

Compounds and/or compositions as taught there for use in a method of treatment, for example to control a biofilm and/or microbial growth, e.g., by enhancing the effects of an antibiotic that is administered in combination with the compound, are further provided. Also provided is the use of compounds and/or compositions disclosed herein for the preparation of a medicament for the treatment and/or prevention of a bacterial or other microbial infection, e.g., by enhancing the effects of an antibiotic that is administered in combination with the compound.

DETAILED DESCRIPTION OF EMBODIMENTS

The present invention is further described below. All patent references referred to in this patent application are hereby incorporated by reference in their entireties to the extent consistent with the disclosures herein.

A. Definitions

The following definitions are used herein.

"Active compound" as used herein refers to the various embodiments of compounds described in Section B (2-aminoimidazole-phenyl derivatives) set forth below.

"Imidazole" refers to the commonly-known structure:

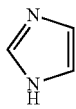

"H" refers to a hydrogen atom. "C" refers to a carbon atom. "N" refers to a nitrogen atom. "O" refers to an oxygen atom. "Halo" refers to F, Cl, Br or I. The term "hydroxy," as used herein, refers to an —OH moiety. "Br" refers to a bromine atom. "Cl" refers to a chlorine atom. "I" refers to an iodine atom. "F" refers to a fluorine atom.

An "acyl group" is intended to mean a group —C(O)—R, where R is a suitable substituent (for example, an acetyl group, a propionyl group, a butyroyl group, a benzoyl group, or an alkylbenzoyl group).

"Alkyl," as used herein, refers to a straight or branched chain hydrocarbon containing from 1 or 2 to 10 or 20 or more carbon atoms (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, etc.). In some embodiments the alkyl can be a lower alkyl. "Lower alkyl" refers to straight or branched chain alkyl having from 1 to 3, or from 1 to 5, or from 1 to 8 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like.

As generally understood by those of ordinary skill in the art, "saturation" refers to the state in which all available valence bonds of an atom (e.g., carbon) are attached to other atoms. Similarly, "unsaturation" refers to the state in which not all the available valence bonds are attached to other atoms; in such compounds the extra bonds usually take the form of double or triple bonds (usually with carbon). For example, a carbon chain is "saturated" when there are no double or triple bonds present along the chain or directly connected to the chain (e.g., a carbonyl), and is "unsaturated" when at least one double or triple bond is present along the chain or directly connected to the chain (e.g., a carbonyl). Further, the presence or absence of a substituent depending upon chain saturation will be understood by those of ordinary skill in the art to depend upon the valence requirement of the atom or atoms to which the substituent binds (e.g., carbon).

"Haloalkyl," as used herein, a refers to a straight or branched chain hydrocarbon containing from 1 or 2 to 10 or 20 or more carbon atoms (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, etc.) in which at least one of the hydrogen atoms have been replaced with halo (e.g., F, Cl, Br or I). Representative examples of "haloalkyl" include, but are not limited to, fluoroalkyl (e.g., trifluoromethyl (—$CF_3$)).

"Alkenyl," as used herein, refers to a straight or branched chain hydrocarbon containing from 2 to 10 or 20 or more carbons, and containing at least one carbon-carbon double bond, formed structurally, for example, by the replacement of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like.

"Alkynyl," as used herein, refers to a straight or branched chain hydrocarbon group containing from 2 to 10 or 20 or more carbon atoms, and containing at least one carbon-carbon triple bond. Representative examples of alkynyl include, but are not limited, to acetylenyl, 1-propynyl, 2-propynyl, 3-butynyl, 2-pentynyl, 1-butynyl and the like.

The term "cycloalkyl," as used herein, refers to a saturated cyclic hydrocarbon group containing from 3 to 8 carbons or more. Representative examples of cycloalkyl include, but are not limited to, cyclopropyl, cyclobutyl, cyclopentyl, cyclohexyl, cycloheptyl, and cyclooctyl. In some embodiments, the rings can be bridged to form a polycyclic ring system.

"Heterocyclo," as used herein, refers to a monocyclic, bicyclic or tricyclic ring system. Monocyclic heterocycle ring systems are exemplified by any 5 or 6 member ring containing 1, 2, 3, or 4 heteroatoms independently selected from the group consisting of: O, N, and S. The 5 member ring has from 0 to 2 double bonds, and the 6 member ring has from 0 to 3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, sulfoxide, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, thiopyranopyridine, and the like.

"Aryl" as used herein refers to a ring system having one or more aromatic rings. Representative examples of aryl include azulenyl, indanyl, indenyl, naphthyl, phenyl, tetrahydronaphthyl, and the like. The aryl groups of this invention can be substituted with 1, 2, 3, 4, or 5 substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, aryloxy, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, sulfonate, —NR'R" (wherein, R' and R" are independently selected from hydrogen, alkyl, alkylcarbonyl, aryl, arylalkyl and formyl), and —C(O)NR'R" (wherein R' and R" are independently selected from hydrogen, alkyl, alkylcarbonyl, aryl, arylalkyl, and formyl).

"Heteroaryl" means a cyclic, aromatic hydrocarbon in which one or more carbon atoms have been replaced with heteroatoms (e.g., N, O or S). If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolyl, quinolyl, phthalazinyl, naphthyridinyl, quinoxalinyl, isothiazolyl, and benzo[b]thienyl. Preferred heteroaryl groups are five and six membered rings and contain from one to three heteroatoms independently selected from the group consisting of: O, N, and S. The heteroaryl group, including each heteroatom, can be unsubstituted or substituted with from 1 to 4 suitable substituents, as chemically feasible. For example, the heteroatom S may be substituted with one or two oxo groups, which may be shown as =O.

"Alkoxy," as used herein, refers to an alkyl group, as defined herein, appended to the parent molecular moiety through an oxy group, as defined herein. Representative examples of alkoxy include, but are not limited to, methoxy, ethoxy, propoxy, 2-propoxy, butoxy, tert-butoxy, pentyloxy, hexyloxy and the like.

An "amine" or "amino" is intended to mean the group —NH$_2$.

An "amide" as used herein refers to an organic functional group having a carbonyl group (C=O) linked to a nitrogen atom (N), or a compound that contains this group, generally depicted as:

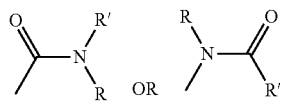

wherein, R and R' can independently be any covalently-linked atom or atoms.

A "thiol" or "mercapto" refers to an —SH group or to its tautomer =S.

A "sulfone" as used herein refers to a sulfonyl functional group, generally depicted as:

wherein, R can be any covalently-linked atom or atoms.

A "sulfoxide" as used herein refers to a sulfinyl functional group, generally depicted as:

wherein, R can be any covalently-linked atom or atoms.

The term "oxo," as used herein, refers to a =O moiety. The term "oxy," as used herein, refers to a —O— moiety.

"Nitro" refers to the organic compound functional group —NO$_2$.

"Carbonyl" is a functional group having a carbon atom double-bonded to an oxygen atom (—C=O). "Carboxy" as used herein refers to a —COOH functional group, also written as —CO$_2$H or —(C=O)—OH.

"Amino acid sidechain" as used herein refers to any of the 20 commonly known groups associated with naturally-occurring amino acids, or any natural or synthetic homologue thereof. An "amino acid" includes the sidechain group and the amino group, alpha-carbon atom, and carboxy groups, as commonly described in the art. Examples of amino acids include glycine, and glycine that is substituted with a suitable substituent as described herein, such as alkyl, alkenyl, alkynyl, cycloalkyl, heterocyclo, aryl, heteroaryl, alkoxy, carbonyl, carboxy, etc., or a pharmaceutically acceptable salt thereof. For example, "Histidine" is one of the 20 most commonly known amino acids found naturally in proteins. It contains an imidazole side chain substituent. Other examples of naturally-occurring amino acids include lysine, arginine, aspartic acid, glutamic acid, asparagine, glutamine, serine, threonine, tyrosine, alanine, valine, leucine, isoleucine, phenylalanine, methionine, tryptophan, and cysteine. Also included in the definitions of "amino acid sidechain" and "amino acid" is proline, which is commonly included in the definition of an amino acid, but is technically an imino acid. As used in this application, both the naturally-occurring L-, and the non-natural D-amino acid enantiomers are included. The single letter code for amino acids is A (Ala), C (Cys), D (Asp), E (Glu), F (Phe), G (Gly), H (His), I (Ile), K (Lys), L (Leu), M (Met), N (Asn), P (Pro), Q (Gln), R (Arg), S (Ser), T (Thr), V (Val), W (Trp), and Y (Tyr). A "peptide" is a linear chain of amino acids covalently linked together, typically through an amide linkage, and contains from 1 or 2 to 10 or 20 or more amino acids, and is also optionally substituted and/or branched.

"Fused ring" as used herein refers to a ring system (e.g., "cycloalkyl," "cycloalkenyl," "heterocyclo," "aryl," or "heteroaryl") that may be formed by two substituents of a formula as provided herein. Each of two substituents may together form part of a ring system, as illustrated below as Fused ring I or Fused ring II for example substituents R$_2$ and R$_3$. Carbons included in the fused rings may be substituted by heteroatoms independently selected from the group consisting of: O, N, and S. The fused ring system, including each heteroatom, when present, can be unsubstituted or substituted with from 1 to 4 suitable substituents, as chemically feasible.

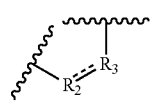

Fused ring I

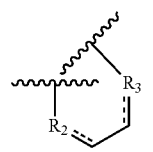

Fused ring II

A "pharmaceutically acceptable salt" is intended to mean a salt that retains the biological effectiveness of the free acids and bases of a specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates.

A "prodrug" is intended to mean a compound that is converted under physiological conditions or by solvolysis or metabolically to a specified compound that is pharmaceutically active. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein in their entireties.

In some embodiments, alkyl groups, alkenyl groups, alkynyl groups, cycloalkyl groups, heterocyclo groups, aryl groups, heteroaryl groups, alkoxy groups, amine groups, amide groups, thiol groups, sulfone groups, sulfoxide groups, carbonyl groups and carboxy groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, nitrile, carbonyl, carboxy, amino acid sidechain, amino acid and peptide etc.

As understood in the art, the term "optionally substituted" indicates that the specified group is either unsubstituted, or substituted by one or more suitable substituents. A "substituent" that is "substituted" is an atom or group which takes the place of a hydrogen atom on the parent organic molecule.

B. Active Compounds

Active compounds of the present invention are provided below. In some of the embodiments provided, active compounds are 2-aminoimidazole-phenyl derivatives. Active compounds as described herein can be prepared as shown below or in accordance with known procedures or variations thereof that will be apparent to those skilled in the art.

As will be appreciated by those of skill in the art, the active compounds of the various formulas disclosed herein may contain chiral centers, e.g. asymmetric carbon atoms. Thus, the present invention is concerned with the synthesis of both: (i) racemic mixtures of the active compounds, and (ii) enantiomeric forms of the active compounds. The resolution of racemates into enantiomeric forms can be done in accordance with known procedures in the art. For example, the racemate may be converted with an optically active reagent into a diastereomeric pair, and the diastereomeric pair subsequently separated into the enantiomeric forms.

Geometric isomers of double bonds and the like may also be present in the compounds disclosed herein, and all such stable isomers are included within the present invention unless otherwise specified. Also included in active compounds of the invention are tautomers (e.g., tautomers of imidazole) and rotamers. All chains defined by the formulas herein which include three or more carbons may be saturated or unsaturated unless otherwise indicated.

Active compounds include compounds of Formula (I):

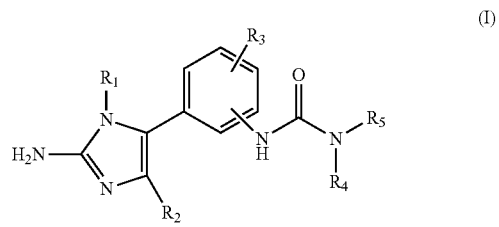

(I)

wherein:

$R_1$ is selected from the group consisting of H and alkyl (e.g., lower alkyl);

$R_2$ is selected from the group consisting of H, alkyl (e.g., lower alkyl), aryl, and heteroaryl;

$R_3$ is selected from the group consisting of H, halo and alkoxy;

or $R_2$ and $R_3$ together form a fused ring; and $R_4$ and $R_5$ are each independently selected from the group consisting of alkyl, aryl, cycloalkyl, heterocyclo, and heteroaryl, or a pharmaceutically acceptable salt or prodrug thereof.

In some embodiments, the compounds are compounds of Formula (I)(a):

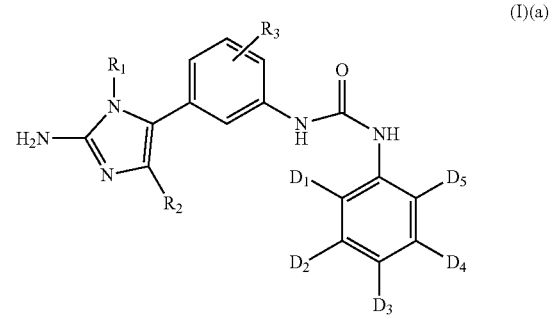

(I)(a)

wherein:

$R_1$, $R_2$ and $R_3$ are as defined above, and $D_1$, $D_2$, $D_3$, $D_4$, and $D_5$ are each independently selected from the group consisting of H, halo, alkyl (e.g., lower alkyl), acyl, alkoxy (e.g., methoxy, and ethoxy), aryl, heteroaryl, amino, amide, nitro, hydroxyl, thiol, sulfone, sulfoxide, nitrile, nitro, and haloalkyl (e.g., fluoroalkyl such as trifluoromethyl (—$CF_3$)), or wherein $D_1$ and $D_2$, $D_2$ and $D_3$, $D_3$ and $D_4$, or $D_4$ and $D_5$ together form a fused ring (e.g., a cyclohexane fused ring), optionally substituted, or a pharmaceutically acceptable salt or prodrug thereof.

In some embodiments, at least one of $D_1$, $D_2$, $D_3$, $D_4$, and $D_5$ is alkyl (e.g., lower alkyl). In some embodiments, $D_3$ is alkyl (e.g., lower alkyl such as n-propyl or n-butyl). In some embodiments, the compounds are compounds of Formula (I)(a)(1):

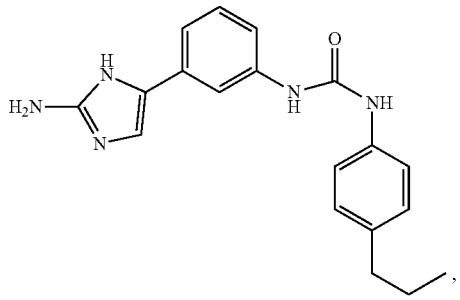

(I)(a)(1)

or a pharmaceutically acceptable salt thereof.

In some embodiments of Formula (I)(a), at least one of $D_1$, $D_2$, $D_3$, $D_4$, and $D_5$ is heteroaryl. In some embodiments, $D_2$ is heteroaryl (e.g., imidazole). In some embodiments, the compound is a compound of Formula (I)(a)(2):

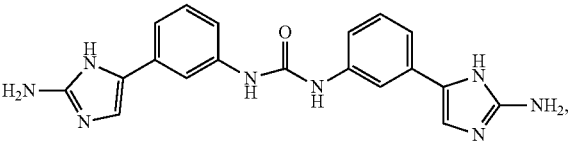

(I)(a)(2)

or a pharmaceutically acceptable salt thereof.

In some embodiments of Formula (I)(a), at least one of $D_1$, $D_2$, $D_3$, $D_4$, and $D_5$ is halo. In some embodiments, $D_2$ and $D_4$ are each halo (e.g., Br). In some embodiments, the compound is a compound of Formula (I)(a)(3):

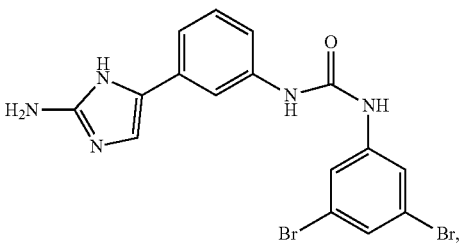

(I)(a)(3)

or a pharmaceutically acceptable salt thereof.

In some embodiments of Formula (I)(a), at least one of $D_1$, $D_2$, $D_3$, $D_4$, and $D_5$ is halo, and at least one of $D_1$, $D_2$, $D_3$, $D_4$, and $D_5$ is haloalkyl. In some embodiments, $D_3$ is fluoro-alkyl (e.g., trifluoromethyl), and $D_4$ is halo (e.g., Cl). In some embodiments, $R_2$ is lower alkyl (e.g, methyl, ethyl, or n-propyl). In some embodiments, the compound is a compound of Formula (I)(a)(4):

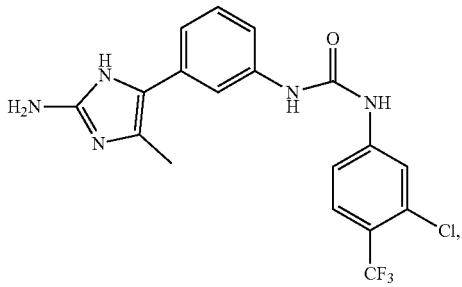

(I)(a)(4)

or a pharmaceutically acceptable salt thereof.

In some embodiments, the compounds are compounds of Formula (I)(b):

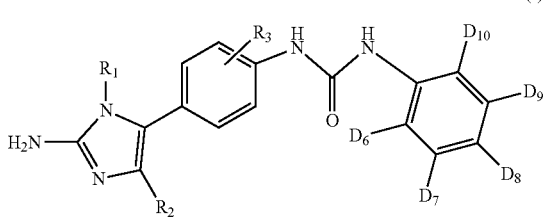

(I)(b)

wherein:

$R_1$, $R_2$ and $R_3$ are as defined above, and $D_6$, $D_7$, $D_8$, $D_9$, and $D_{10}$ are each independently selected from the group consisting of H, halo, alkyl, acyl, alkoxy, aryl, heteroaryl, amino, amide, nitro, hydroxyl, thiol, sulfone, sulfoxide, nitrile, nitro, and haloalkyl (e.g., fluoroalkyl such as trifluoromethyl (—$CF_3$)), or wherein $D_6$ and $D_7$, $D_7$ and $D_8$, $D_8$ and $D_9$, or $D_9$ and $D_{10}$ together form a fused ring, or a pharmaceutically acceptable salt thereof.

In some embodiments of Formula (I)(b), at least one of $D_6$, $D_7$, $D_8$, $D_9$, and $D_{10}$ is heteroaryl. In some embodiments, $D_8$ is heteroaryl (e.g., 2-amino imidazole). In some embodiments, the compound is a compound of Formula (I)(b)(1):

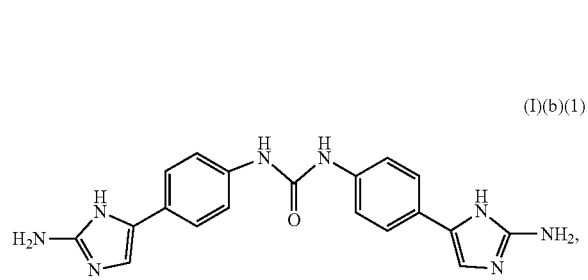 [SMILES: Nc1ncc(-c2ccc(NC(=O)Nc3ccc(-c4cnc(N)[nH]4)cc3)cc2)[nH]1]

(I)(b)(1)

or a pharmaceutically acceptable salt thereof.

In some embodiments, $D_8$ and $D_9$ together form a fused ring (e.g., cyclohexane fused ring), optionally substituted. In some embodiments, the compound is a compound of Formula (I)(b)(2):

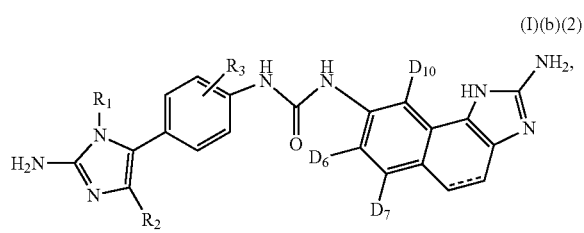

(I)(b)(2)

or a pharmaceutically acceptable salt thereof. In some embodiments, the compound is a compound of Formula (I)(b)(3):

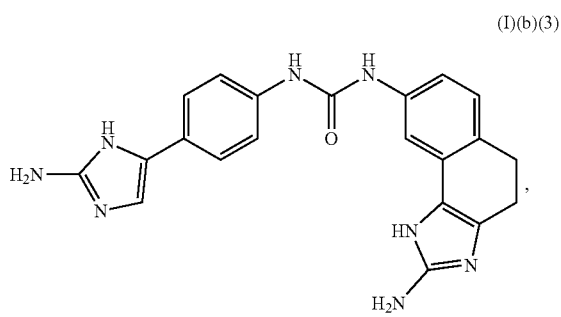 [SMILES: Nc1ncc(-c2ccc(NC(=O)Nc3ccc4c(c3)-c3[nH]c(N)nc3CC4)cc2)[nH]1]

(I)(b)(3)

or a pharmaceutically acceptable salt thereof.

C. Compositions

In some embodiments, compositions are provided, comprising a carrier and an effective amount of active compound. In some embodiments, the effective amount of active compound may enhance the effects of an antibiotic that is administered in combination with the compound.

In some embodiments, biofilm and/or bacterial growth inhibiting compositions are provided, comprising a carrier, optionally an antibiotic, and an effective amount of active compound. "Biofilm" or "biofilms" refer to communities of microorganisms that are attached to a substrate. The microorganisms often excrete a protective and adhesive matrix of polymeric compounds. They often have structural heterogeneity, genetic diversity, and complex community interactions. "Biofilm inhibiting", "biofilm reducing", "biofilm resistant", "biofilm controlling" or "antifouling" refer to inhibition of the establishment or growth of a biofilm, or decrease in the amount of organisms that attach and/or grow upon a substrate. As used herein, a "substrate" can include any living or nonliving structure. For example, biofilms often grow on synthetic materials submerged in an aqueous solution or exposed to humid air, but they also can form as floating mats on a liquid surface, in which case the microorganisms are adhering to each other or to the adhesive matrix characteristic of a biofilm.

"Bacterial growth" inhibiting, reducing or controlling refers to inhibition of the growth and/or reduction in the number of bacteria, whether in a biofilm or planktonic.

In some embodiments, the carrier is a pharmaceutically acceptable carrier. A "pharmaceutically acceptable carrier" as used herein refers to a carrier that, when combined with an active compound of the present invention, facilitates the application or administration of that active compound for its intended purpose to enhance the effects of an antibiotic that is administered in combination with the compound. The active compounds may be formulated for administration in a pharmaceutically acceptable carrier in accordance with known techniques. See, e.g., Remington, *The Science and Practice of Pharmacy* (9$^{th}$ Ed. 1995). The pharmaceutically acceptable carrier must, of course, also be acceptable in the sense of being compatible with any other ingredients in the composition. The carrier may be a solid or a liquid, or both, and is preferably formulated with the compound as a unit-dose composition, for example, a tablet, which may contain from 0.01% or 0.5% to 95% or 99% by weight of the active compound. One or more active compounds may be included in the compositions of the invention, which may be prepared by any of the well-known techniques of pharmacy comprising admixing the components, optionally including one or more accessory ingredients.

In general, compositions may be prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

The compositions of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound that is being used. Routes of parenteral administration include intrathecal injection, intraventricular injection and intracranial injection.

Compositions suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such compositions may be prepared by any suitable method of pharmacy, which includes the step of bringing into association the active compound and a suitable carrier (which may contain one or more accessory ingredients as noted above).

Compositions suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Compositions of the present invention suitable for parenteral administration comprise sterile aqueous and non-aqueous injection solutions of the active compound, which preparations are preferably isotonic with the blood of the intended recipient. These preparations may contain antioxidants, buffers, bacteriostats and solutes that render the composition isotonic with the blood of the intended recipient. Aqueous and non-aqueous sterile suspensions may include suspending agents and thickening agents. The compositions may be presented in unit/dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

For example, in one aspect of the present invention, there is provided an injectable, stable, sterile composition comprising an active compound as described herein, or a salt or prodrug thereof, in a unit dosage form in a sealed container. The compound or salt is provided in the form of a lyophilizate that is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent that is physiologically acceptable may be employed in sufficient quantity to emulsify the compound or salt in an aqueous carrier. One such useful emulsifying agent is phosphatidyl choline.

Compositions suitable for rectal administration are preferably presented as unit dose suppositories. These may be prepared by mixing the active compound with one or more conventional solid carriers, for example, cocoa butter, and then shaping the resulting mixture.

Compositions suitable for topical application to the skin preferably take the form of an ointment, cream, lotion, paste, gel, spray, aerosol, or oil. Carriers that may be used include petroleum jelly, lanoline, polyethylene glycols, alcohols (e.g., ethanol, isopropanol, etc.), transdermal enhancers, and combinations of two or more thereof.

Compositions suitable for transdermal administration may be presented as discrete patches adapted to remain in intimate contact with the epidermis of the recipient for a prolonged period of time. Compositions suitable for transdermal administration may also be delivered by iontophoresis (see, for example, *Pharmaceutical Research* 3 (6):318 (1986)) and typically take the form of an optionally buffered aqueous solution of the active compound.

Also provided in some embodiments are compositions comprising an active compound and a biocide. A "biocide" as used herein refers to a substance with the ability to kill or to inhibit the growth of microorganisms (e.g., bacteria, fungal cells, protozoa, etc.), whether as a disinfectant, an antiseptic, or an antibiotic, which substance is not an active compound; See above in Section B. Common biocides include oxidizing and non-oxidizing chemicals. Examples of oxidizing biocides include chlorine, chlorine dioxide, and ozone. Examples of non-oxidizing biocides include quaternary ammonium compounds, formaldehyde, and anionic and non-anionic surface agents. Chlorine is the most common biocide used in sanitizing water systems. Chlorhexidine (e.g., chorhexidine gluconate) is a biocide commonly used as an antiseptic in oral rinses and skin cleansers. Iodine preparations are also commonly used as disinfectants.

An "antibiotic" as used herein is a type of "biocide." Common antibiotics include aminoglycosides, carbacephems (e.g., loracarbef), carbapenems, cephalosporins, glycopeptides (e.g., teicoplanin and vancomycin), macrolides, monobactams (e.g., aztreonam) penicillins, polypeptides (e.g., bacitracin, colistin, polymyxin B), quinolones, sulfonamides, tetracyclines, etc. Antibiotics treat infections by either killing or preventing the growth of microorganisms. Many act to inhibit cell wall synthesis or other vital protein synthesis of the microorganisms.

Aminoglycosides are commonly used to treat infections caused by Gram-negative bacteria such as *Escherichia coli* and *Klebsiella*, particularly *Pseudomonas aeroginosa*. Examples of aminoglycosides include, but are not limited to amikacin, gentamicin, kanamycin, neomycin, netilmicin, streptomycin, tobramycin, and paromomycin.

Carbapenems are broad-spectrum antibiotics, and include, but are not limited to, ertapenem, doripenem, imipenem/cilstatin, and meropenem.

Cephalosporins include, but are not limited to, cefadroxil, cefazolin, cefalotin (cefalothin), cefalexin, cefaclor, cefamandole, cefoxitin, cefprozil, loracarbef, cefuroxime, cefixime, cefdinir, cefditoren, cefoperazone, cefotaxime, cefpodoxime, ceftazidime, ceftibuten, ceftizoxime, ceftriaxone, cefepime, cefpirome, and ceftobiprole.

Macrolides include, but are not limited to, azithromycin, clarithromycin, dirithromycin, erythromycin, roxithromycin, troleandomycin, telithromycin and spectinomycin.

Penicillins include, but are not limited to, amoxicillin, ampicillin, azlocillin, bacampicillin, carbenicillin, cloxacillin, dicloxacillin, flucloxacillin, mezlocillin, meticillin, nafcillin, oxacillin, penicillin, piperacillin and ticarcillin.

Quinolones include, but are not limited to, ciprofloxacin, enoxacin, gatifloxacin, gemifloxacin, levofloxacin, lomefloxacin, moxifloxacin, norfloxacin, ofloxacin and trovafloxacin.

Sulfonamides include, but are not limited to, mafenide, prontosil, sulfacetamide, sulfamethizole, sulfanilamide, sulfasalazine, sulfisoxazole, trimethoprim, and co-trimoxazole (trimethoprim-sulfamethoxazole).

Tetracyclines include, but are not limited to, demeclocycline, doxycycline, minocycline, oxytetracycline and tetracycline.

Other antibiotics include arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin (rifampicin), tinidazole, etc.

In some embodiments, a dentifrice composition is provided comprising the active compounds. A "dentifrice" is a substance that is used to clean the teeth. It may be in the form of, e.g., a paste or powder. Commonly known dentifrices include toothpaste, mouthwash, chewing gum, dental floss, and dental cream. Other examples of dentifrices include toothpowder, mouth detergent, troches, dental or gingival massage cream, dental strips, dental gels, and gargle tablets. Examples of dentifrice compositions comprising toothpaste and mouthwash are found in U.S. Pat. No. 6,861,048 (Yu et al.); U.S. Pat. No. 6,231,836 (Takhtalian et al.); and U.S. Pat. No. 6,331,291 (Glace et al.); each incorporated by reference herein in their entirety.

A coating composition is also provided. A "coating" as used herein is generally known. Any of a variety of organic and aqueous coating compositions, with or without pigments, may be modified to contain biofilm inhibiting compositions as described herein, including but not limited to those described in U.S. Pat. Nos. 7,109,262, 6,964,989, 6,835,459, 6,677,035, 6,528,580, 6,235,812, etc., each incorporated by reference herein in their entirety.

In general, the coatings comprise a film-forming resin, an aqueous or organic solvent that disperses the resin; and, optionally, at least one pigment. Other ingredients such as colorants, secondary pigments, stabilizers and the like can be included if desired. However, for use in the present invention the compositions further comprise one or more compounds as described herein, which may be carried by or dispersed in the solvent and/or resin, so that the compounds are dispersed or distributed on the substrate an article coated. A resin may carry the compounds through covalent attachment through means well known in the art. The resin may comprise, for example, a polymeric material. A polymeric material is a material that is comprised of large molecules made from associated smaller repeating structural units, often covalently linked. Common examples of polymeric materials are unsaturated polyester resins, and epoxy resins.

Any suitable article can be coated, in whole or in part, with a composition of the invention. Suitable articles include, but are not limited to, automobiles and airplanes (including substrates such as wing and propeller surfaces for aerodynamic testing), boat vessel hulls (including interior and exterior surfaces thereof), pressure vessels (including interior and exterior surfaces thereof) medical implants, windmills, etc. Coating of the article with the composition can be carried out by any suitable means, such as by brushing, spraying, electrostatic deposition, dip coating, doctor blading, etc.

D. Methods of Use

Methods of controlling biofilm formation and/or bacterial growth on a substrate are disclosed, comprising the step of administering an active compound to a substrate in an amount effective to control the biofilm formation and/or bacterial growth, e.g., to enhance the effects of an antibiotic that is administered in combination with the compound, thereby inhibiting biofilm formation and/or bacterial growth. A "substrate" as used herein is a base on which an organism, such as those commonly found in biofilms, may live. The term "substrate," as used herein, refers to any substrate, whether in an industrial or a medical setting, that provides or can provide an interface between an object and a fluid, permitting at least intermittent contact between the object and the fluid. A substrate, as understood herein, further provides a plane whose mechanical structure, without further treatment, is compatible with the adherence of microorganisms. Substrates compatible with biofilm formation may be natural or synthetic, and may be smooth or irregular. Fluids contacting the substrates can be stagnant or flowing, and can flow intermittently or continuously, with laminar or turbulent or mixed flows. A substrate upon which a biofilm forms can be dry at times with sporadic fluid contact, or can have any degree of fluid exposure including total immersion. Fluid contact with the substrate can take place via aerosols or other means for air-borne fluid transmission.

Biofilm formation with health implications can involve those substrates in all health-related environments, including substrates found in medical environments and those substrates in industrial or residential environments that are involved in those functions essential to human well being, for example, nutrition, sanitation and the prevention of disease. Substrates found in medical environments include the inner and outer aspects of various instruments and devices, whether disposable or intended for repeated uses. Examples include the entire spectrum of articles adapted for medical use, including scalpels, needles, scissors and other devices used in invasive surgical, therapeutic or diagnostic procedures; implantable medical devices, including artificial blood vessels, catheters and other devices for the removal or delivery of fluids to patients, artificial hearts, artificial kidneys, orthopedic pins, plates and implants; catheters and other tubes (including urological and biliary tubes, endotracheal tubes, peripherably insertable central venous catheters, dialysis catheters, long term tunneled central venous catheters, peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, heart valves, artificial joints, artificial larynxes, otological implants), vascular catheter ports, wound drain tubes, hydrocephalus shunts, pacemakers and implantable defibrillators, and the like. Other examples will be readily apparent to practitioners in these arts. Substrates found in the medical environment also include the inner and outer aspects of pieces of medical equipment, medical gear worn or carried by personnel in the health care setting. Such substrates can include counter tops and fixtures in areas used for medical procedures or for preparing medical apparatus, tubes and canisters used in respiratory treatments, including the administration of oxygen, of solubilized drugs in nebulizers and of anesthetic agents. Also included are those substrates intended as biological barriers to infectious organisms in medical settings, such as gloves, aprons and faceshields. Commonly used materials for biological barriers may be latex-based or non-latex based. Vinyl is commonly used as a material for non-latex surgical gloves. Other such substrates can include handles and cables for medical or dental equipment not intended to be sterile. Additionally, such substrates can include those non-sterile external substrates of tubes and other apparatus found in areas where blood or body fluids or other hazardous biomaterials are commonly encountered.

Substrates in contact with liquids are particularly prone to biofilm formation. As an example, those reservoirs and tubes used for delivering humidified oxygen to patients can bear biofilms inhabited by infectious agents. Dental unit waterlines similarly can bear biofilms on their substrates, providing a reservoir for continuing contamination of the system of flowing aerosolized water used in dentistry. Sprays, aerosols and nebulizers are highly effective in disseminating biofilm fragments to a potential host or to another environmental site. It is especially important to health to prevent biofilm formation on those substrates from where biofilm fragments can be carried away by sprays, aerosols or nebulizers contacting the substrate.

Other substrates related to health include the inner and outer aspects of those articles involved in water purification, water storage and water delivery, and articles involved in food processing. Substrates related to health can also include the inner and outer aspects of those household articles involved in providing for nutrition, sanitation or disease prevention. Examples can include food processing equipment for home use, materials for infant care, tampons and toilet bowls. "Substrate" as used herein also refers to a living substrate, such as the inner ear of a patient.

Substrates can be smooth or porous, soft or hard. Substrates can include a drainpipe, glaze ceramic, porcelain, glass, metal, wood, chrome, plastic, vinyl, Formica® brand laminate, or any other material that may regularly come in contact with an aqueous solution in which biofilms may form and grow. The substrate can be a substrate commonly found on household items such as shower curtains or liners, upholstery, laundry, and carpeting.

A substrate on which biofilm inhibiting is important is that of a ship hull. Biofilms, such as those of *Halomonas pacifica*, promote the corrosion of the hull of ships and also increase the roughness of the hull, increasing the drag on the ship and thereby increasing fuel costs. The biofilm can also promote the attachment of larger living structures such as barnacles on the ship hull. Fuel can account for half of the cost of marine shipping, and the loss in fuel efficiency due to biofilm formation is substantial.

Substrates on which biofilms can adhere include those of living organisms, as in the case of humans with chronic infections caused by biofilms, as discussed above. Biofilms can also form on the substrates of food contact surfaces, such as those used for processing seafood, and also on food products themselves. Examples of seafood products that may have biofilm contamination include oysters. Human infections caused by the ingestion of raw oysters has been linked to *Vibrio vulnificus* bacterium. *Vibrio* bacteria attach to algae and plankton in the water and transfer to the oysters and fish that feed on these organisms.

Other examples of substrates or devices on which biofilms can adhere can be found in U.S. Pat. Nos. 5,814,668 and 7,087,661; and U.S. Pat. Appln. Publication Nos. 2006/0228384 and 2006/0018945, each of which is incorporated herein by reference in its entirety.

In some embodiments, methods of enhancing the effects of a biocide (e.g., antibiotic) are disclosed, comprising the step of administering an active compound in combination with a biocide, the active compound being administered in an amount effective to enhance the effects of the biocide.

"Administering" or "administration of" an active compound and/or biocide as used herein is inclusive of contacting, applying, etc. (e.g., contacting with an aqueous solution, contacting with a surface (e.g., a hospital surface such as a table, instrumentation, etc.)), in addition to providing to a subject (for example, to a human subject in need of treatment for a microbial infection).

"Enhancing" the effects of a biocide (e.g., antibiotic) by administering an active compound in combination with the biocide refers to increasing the effectiveness of the biocide, such that the microorganism killing and/or growth inhibition is higher at a certain concentration of the biocide administered in combination with the active compound than without. In some embodiments, a bacteria or other microorganism is "sensitized" to the effects of a biocide, such that the bacteria or other microorganism that was resistant to the biocide prior to administering the active compound (e.g., little to none, or less than 20, 10, 5 or 1% are killed upon application) is rendered vulnerable to that biocide upon or after administering the active compound (e.g., greater than 20, 30, 40, 50, 60, 70, 80, 90, or 95% or more are killed). In some embodiments, "enhancing" the effects of an antibiotic by administering an active compound in combination with the antibiotic refers to decreasing a minimal inhibitory concentration (MIC) of the antibiotic.

As used herein, the administration of two or more compounds (inclusive of active compounds and biocides) "in combination" means that the two compounds are administered closely enough in time that the administration of or presence of one alters the biological effects of the other. The two compounds may be administered simultaneously (concurrently) or sequentially.

Simultaneous administration of the compounds may be carried out by mixing the compounds prior to administration, or by administering the compounds at the same point in time but at different anatomic sites or using different routes of administration, or administered at times sufficiently close that the results observed are indistinguishable from those achieved when the compounds are administered at the same point in time.

Sequential administration of the compounds may be carried out by administering, e.g., an active compound at some point in time prior to administration of a biocide, such that the prior administration of active compound enhances the effects of the biocide (e.g., percentage of microorganisms killed and/or slowing the growth of microorganisms). In some embodiments, an active compound is administered at some point in time prior to the initial administration of a biocide. Alternatively, the biocide may be administered at some point in time prior to the administration of an active compound, and optionally, administered again at some point in time after the administration of an active compound.

Also disclosed is a method of controlling biofilm formation wherein the biofilm comprises Gram-negative or Gram-positive bacteria.

"Gram-negative" bacteria are those that do not retain crystal violet dye after an alcohol wash in the Gram staining protocol, while "Gram-positive" bacteria are those that are stained dark blue or violet color after an alcohol wash in the Gram staining protocol. This is due to structural properties in the cell walls of the bacteria. Gram-positive bacteria retain the crystal violet color due to a high amount of peptidoglycan in the cell wall.

Gram-negative bacteria may include, but are not limited to, bacteria of the genera *Acinetobacter, Escherichia, Klebsiella Proteus, Neisseria, Helicobacter, Brucella, Legionella, Campylobacter, Francisella, Pasteurella, Yersinia, Bartonella, Bacteroides, Streptobacillus, Spirillum, Moraxella, Shigella, Salmonella, Vibrio*, and *Helicobacter*.

Gram-positive bacteria may include, but are not limited to, bacteria of the genera *Listeria, Staphylococcus, Streptococcus, Bacillus, Corynebacterium, Enterococcus, Peptostreptococcus*, and *Clostridium*.

Many genera and species of Gram-negative and Gram-positive bacteria are pathogenic. Examples of genera of bacteria affected by active compounds of this invention include, but are not limited to, *Acinetobacter, Escherichia*, and *Klebsiella*. Examples of species of bacteria capable of forming biofilms that are affected by active compounds of the present invention include *Acinetobacter baumannii, Klebsiella pneumoniae*, and *Escherichia coli*.

Additional bacteria genera in which compounds disclosed herein may be useful in controlling biofilms include, but are not limited to, *Actinomyces, Propionibacterium, Nocardia* and *Streptomyces*. *Actinomyces* is a Gram-positive genus that includes opportunistic pathogens in humans and animals, e.g., in the oral cavity, and can cause actinomycosis (cause by, e.g., *Actinomyces israelii*). *Propionibacterium acnes* is a Gram-positive species that can cause acne and chronic blepharitis and endophthalmitis (e.g., after intraocular surgery). *Nocardia* is a Gram-positive genus that includes opportunistic pathogenic species causing, e.g., slowly progressive pneumonia, encephalitis, etc. *Streptomyces* is a Gram-positive genus that occasionally is found in human infections, such as mycetoma (caused by, e.g., *S. somaliensis* and *S. sudanensis*).

A method for treating a chronic bacterial infection in a subject in need thereof is disclosed, comprising administering active compound to said subject, e.g., in an amount effective to enhance the effects of an antibiotic that is administered in combination with the active compound, thereby inhibiting, reducing, or removing a biofilm component of said chronic bacterial infection. "Treating" as used herein refers to any type of activity that imparts a benefit to a patient afflicted with a disease, including improvement in the condition of the patient (e.g., in one or more symptoms), delay in the progression of the disease, delay in onset of the disease, etc. The present invention is primarily concerned with the treatment of human subjects, but the invention may also be carried out on animal subjects, particularly mammalian subjects (e.g., mice, rats, dogs, cats, rabbits, and horses), avian subjects (e.g., parrots, geese, quail, pheasant), livestock (e.g., pigs, sheep, goats, cows, chickens, turkey, duck, ostrich, emu), reptile and amphibian subjects, for veterinary purposes or animal husbandry, and for drug screening and drug development purposes.

A "chronic bacterial infection" is a bacterial infection that is of a long duration or frequent recurrence. For example, a chronic middle ear infection, or otitis media, can occur when the Eustachian tube becomes blocked repeatedly due to allergies, multiple infections, ear trauma, or swelling of the adenoids. The definition of "long duration" will depend upon the particular infection. For example, in the case of a chronic middle ear infection, it may last for weeks to months. Other known chronic bacterial infections include urinary tract infection (most commonly caused by *Escherichia coli* and/or *Staphylococcus saprophyticus*), gastritis (most commonly caused by *Helicobacter pylori*), respiratory infection (such as those commonly afflicting patents with cystic fibrosis, most commonly caused by *Pseudomonas aeuroginosa*), cystitis (most commonly caused by *Escherichia coli*), pyelonephritis (most commonly caused by *Proteus* species, *Escherichia coli* and/or *Pseudomonas* species), osteomyelitis (most commonly caused by *Staphylococcus aureus*, but also by *Escherichia coli*), bacteremia, skin infection, rosacea, acne, chronic wound infection, infectious kidney stones (can be caused by *Proteus mirabilis*), bacterial endocarditis, and sinus infection. A common infection afflicting pigs is atrophic rhinitis (caused by *Bordatella* species, e.g. *Bordatella bronchiseptica, Bordatella rhinitis*, etc.).

Various nosocomial infections that are especially prevalent in intensive care units implicate *Acinetobacter* species such as *Acinetobacter baumannii* and *Acinetobacter lwoffi*. *Acinetobacter baumanni* is a frequent cause of nosocomial pneumonia, and can also cause skin and wound infections and bacteremia. *Acinetobacter lwoffi* causes meningitis. The *Acinetobacter* species are resistant to many classes of antibiotics. The CDC has reported that bloodstream infections implicating *Acinetobacter baumanni* were becoming more prevalent among service members injured during the military action in Iraq and Afghanistan.

Further provided is the use of the compounds described herein, or an agriculturally acceptable salt thereof, in agricultural applications. See, e.g., U.S. Patent Application Publication No. 2009/0143230 to Melander et al., which is incorporated by reference herein in its entirety. For example, an active compound may be applied to a plant or plant part thereof, to control, inhibit or reduce a microbial infection thereon (e.g., a bacterial or fungal infection), e.g., in combination with an antibiotic.

E. Devices

Medical devices comprising a substrate and an effective amount of active compound are also disclosed. "Medical device" as used herein refers to an object that is inserted or implanted in a subject or applied to a surface of a subject. Common examples of medical devices include stents, fasteners, ports, catheters, scaffolds and grafts. A "medical device substrate" can be made of a variety of biocompatible materials, including, but not limited to, metals, ceramics, polymers, gels, and fluids not normally found within the human body. Examples of polymers useful in fabricating medical devices include such polymers as silicones, rubbers, latex, plastics, polyanhydrides, polyesters, polyorthoesters, polyamides, polyacrylonitrile, polyurethanes, polyethylene, polytetrafluoroethylene, polyethylenetetraphthalate, etc.

Medical devices can also be fabricated using naturally-occurring materials or treated with naturally-occurring materials. Medical devices can include any combination of artificial materials, e.g., combinations selected because of the particular characteristics of the components. Medical devices can be intended for short-term or long-term residence where they are positioned. A hip implant is intended for several decades of use, for example. By contrast, a tissue expander may only be needed for a few months, and is removed thereafter.

Some examples of medical devices are found in U.S. Pat. No. 7,081,133 (Chinn et al.); U.S. Pat. No. 6,562,295 (Neuberger); and U.S. Pat. No. 6,387,363 (Gruskin); each incorporated by reference herein in its entirety.

F. Covalent Coupling of Active Compounds

In some embodiments, active compounds as described herein are covalently coupled to substrates. Examples of substrates include solid supports and polymers. The polymers, typically organic polymers, may be in solid form, liquid form, dispersed or solubilized in a solvent (e.g., to form a coating composition as described above), etc. The solid support may include the substrate examples as described above to be coated with or treated with active compounds of the invention.

Covalent coupling can be carried out by any suitable technique. Active compounds of the present invention may be appended to a substrate via aldehyde condensation, amine bond, amide or peptide bond, carbon-carbon bond, or any suitable technique commonly used in the art. See also U.S. Patent Application Publication No. 2008/0181923 to Melander et al., which is incorporated by reference herein. A preferred method according to some embodiments is amine or amide bond formation. Further examples and explanations of these types of reactions can be found in U.S. Pat. No. 6,136,157 (Lindeberg et al.) and U.S. Pat. No. 7,115,653 (Baxter et al.), which are hereby incorporated by reference in their entireties.

Various coupling reactions can be used to covalently link active compounds of the present invention to a substrate. Examples of coupling reactions that can be used include, but are not limited to, Hiyama, Suzuki, Sonogashira, Heck, Stille, Negishi, Kumada, Wurtz, Ullmann, Cadiot-Chodkiewicz, Buchwald-Hartwig, and Grignard reactions. For example, an active compound that is substituted with a halide (e.g., bromo or chloro) can be coupled to a substrate via a Heck reaction.

Some aspects of the present invention are described in more detail in the following non-limiting examples.

Example 1: Synthesis of Compounds

For synthesis of the following compounds, the typical starting material was a 2-bromo-(3'-nitro)-acetophenone, which may be commercially available, or prepared from a ketone using any of a number of common brominating agents, such as bromine or N-bromosuccinimide (Scheme 1).

Scheme 1

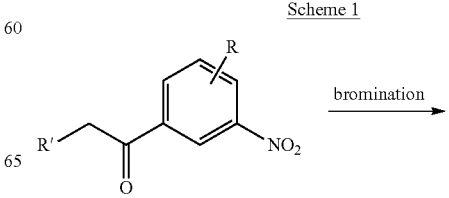

Formation of key intermediates (X) was accomplished by treatment of the starting bromoacetophenone with a suitable guanidine or guanidine equivalent. Condensation with Boc-guanidine provides a monoprotected 2-aminoimidazole which was further protected by treatment with Boc-anhydride and DMAP. Reduction of the nitro group using catalytic hydrogenation conditions provided the desired compounds (Scheme 2).

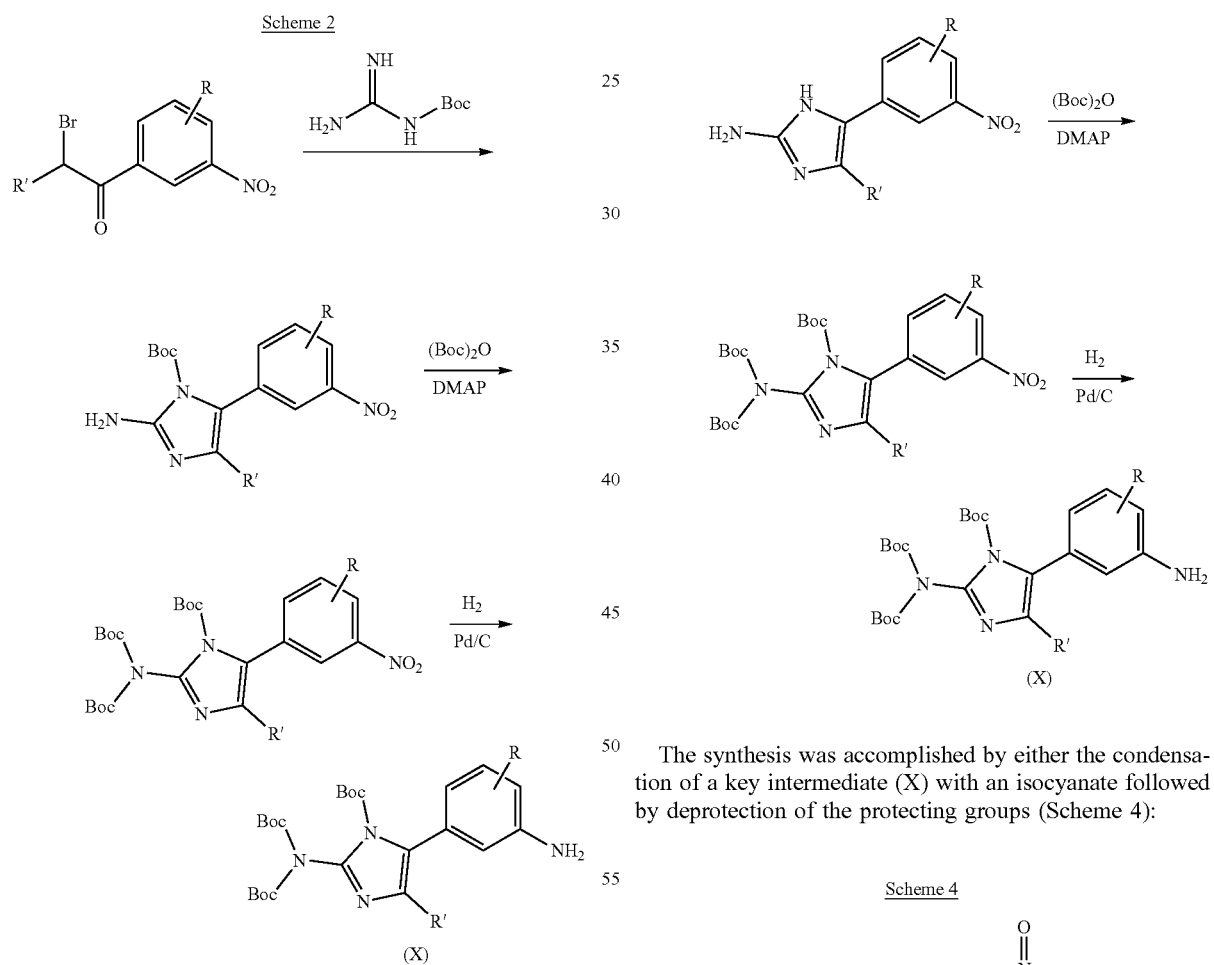

Alternatively, the bromoacetophenones can be condensed with 2-aminopyrimidine to provide the imidazo[1,2-a]pyrimidines. Hydrazinolysis of this compound results in the desired 2-aminoimidazole derivatives which were fully protected with Boc-anhydride and then the nitro group was reduced under catalytic hydrogenation conditions to give the desired compounds (Scheme 3).

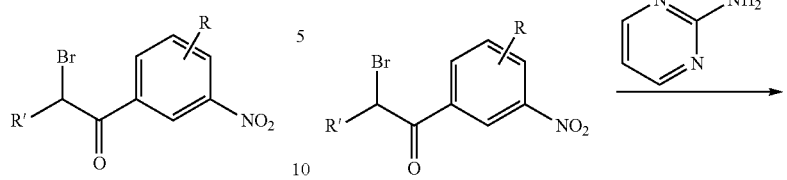

The synthesis was accomplished by either the condensation of a key intermediate (X) with an isocyanate followed by deprotection of the protecting groups (Scheme 4):

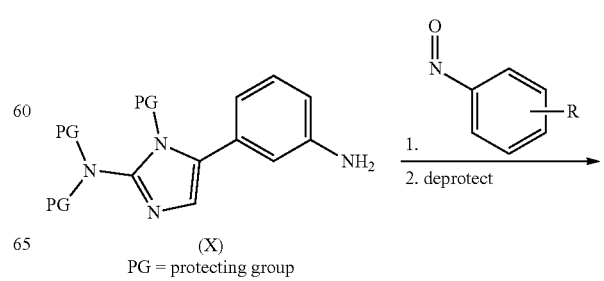

-continued

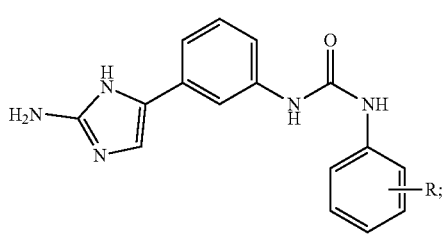

or by in-situ generation of the isocyanate of a key intermediate (X) with a reagent such as triphosgene followed by reaction with an aniline and deprotection of the protecting groups (Scheme 5).

Scheme 5

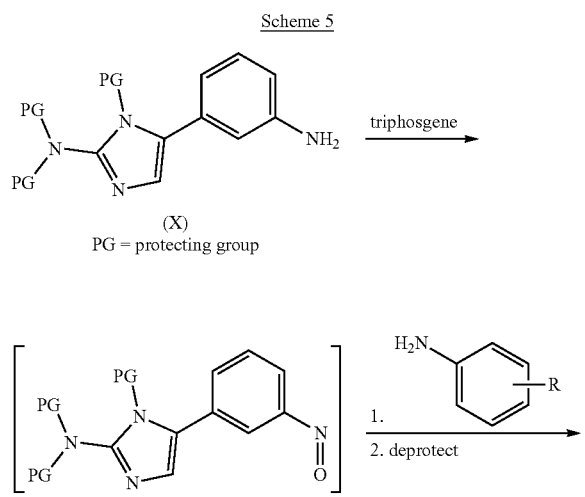

PG = protecting group

Synthesis of Key Intermediate A: 5-(3-aminophenyl)-2-(N,N-bis-tert-butoxycarbonylamino)-1H-imidazole-1-tert-butoxycarbonyl

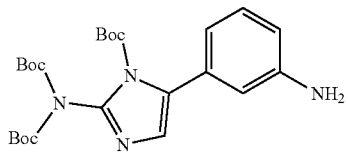 [SMILES: CC(C)(C)OC(=O)N(C(=O)OC(C)(C)C)c1ncc(-c2cccc(N)c2)n1C(=O)OC(C)(C)C]

Step 1: Synthesis of Tert-butyl-2-amino-5-(3-nitrophenyl)-1H-imidazole-1-carboxylate

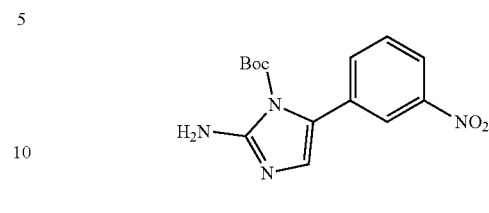

In THF was dissolved 2-bromo-3'-nitroacetophenone (50 g, 1 eq). To this was added Boc-guanidine (65.2 g, 2 eq) and the reaction was stirred at 56 C until starting material was consumed (about 2 hr). The reaction was cooled to OC and stirred for 1 hr. The solids were collected on a filter, washed with THF then washed twice with diethyl ether and dried to provide the desired material as a bright yellow powder.

Step 2: Synthesis of 5-(3-nitrophenyl)-2-(N,N-bis-tert-butoxycarbonylamino)-1H-imidazole-1-tert-butoxycarbonyl

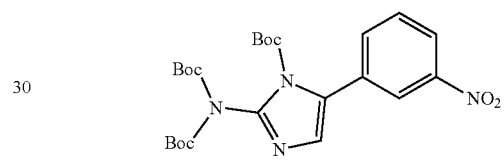

The product from Step 1 (26.2 g, 1 eq) was taken up in THF and treated with (Boc)$_2$O (56.3 g, 3 eq). The mixture was then treated with DMAP (2.1 g, 0.2 eq) and stirred overnight at 40 C. The resulting homogeneous solution was concentrated to an oil. The oil was dissolved in diethyl ether and reconcentrated using heat to sublime excess Boc-anhydride. The residue was taken up in diethyl ether which resulted in a precipitate. The solids were taken up in diethyl ether and broken up with sonication and a spatula. The solids were collected on filter, washed with diethyl ether and air-dried to obtain an off-white powder. This powder was purified by silica gel chromatography to obtain an off-white solid which was triturated in diethyl ether. Collected the solids on a filter and air-dried to obtain the desired material as a white powder.

Step 3: Synthesis of 5-(3-aminophenyl)-2-(N,N-bis-tert-butoxycarbonylamino)-1H-imidazole-1-tert-butoxycarbonyl

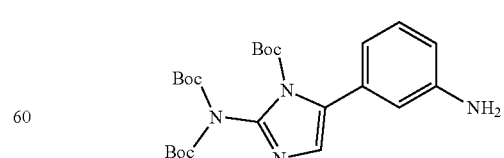

The product from Step 2 (1 mass) was dissolved in MeOH and placed under a nitrogen atmosphere. To this was added 10% Pd/C (0.1 mass) and the nitrogen atmosphere was replaced with a hydrogen atmosphere. The reaction was stirred at r.t. until the starting material was consumed (about 2 hr). The reaction was diluted with an equal volume of EtOAc; stirred for 10 min., then filtered through Celite. The filtrate was concentrated to dryness and dissolved in diethyl ether. Precipitation was induced by partially concentrating the solution without external heat. The mixture was allowed to stir at r.t. for 1 hr, then sonicated and the solids were collected on filter. Washed the solids with diethyl ether and air-dried to obtain the desired product as an off-white solid.

Synthesis of Key Intermediate B: 4-(3-aminophenyl)-5-methyl-2-(N,N-bis-tert-butoxycarbonylamino)-1H-imidazole-3-tert-butoxycarbonyl

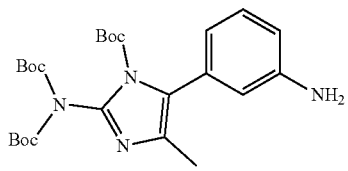 [SMILES: Cc1nc(N(C(=O)OC(C)(C)C)C(=O)OC(C)(C)C)n(C(=O)OC(C)(C)C)c1-c1cccc(N)c1]

Step 1: 2-bromo-1-(3-nitrophenyl)-propan-1-one

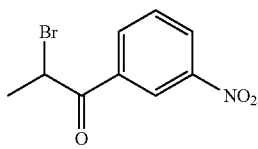

Dissolved 1-(3-nitrophenyl)-propan-1-one (1 eq) in THF and added bromine (1.1 eq) in a dropwise fashion. Stirred at r.t. until starting material was consumed by TLC. Diluted the reaction with ether and washed the organics with a dilute solution of sodium bicarbonate. Dried the organics over sodium sulfate; removed the drying salts by filtration and concentrated the filtrate to dryness to obtain the title compound.

Step 2: 3-methyl-2-(3-nitrophenyl)imidazo[1,2-a]pyrimidine Hydrobromide Salt

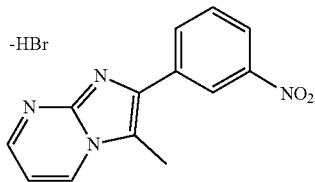 [SMILES: Cc1c(-c2cccc([N+](=O)[O-])c2)nc2ncccn12 ; "-HBr"]

In THF was dissolved 2-bromo-1-(3-nitrophenyl)-propan-1-one (1.1 eq). To this was added 2-aminopyrimidine (2 eq) and the reaction was heated to 65 C for five days. Cooled to rt; collected the solids on filter; washed the solids with THF and air-dried to obtain the title compound as a tan powder.

Step 3: 4-(3-nitrophenyl)-5-methyl-1H-imidazol-2-amine

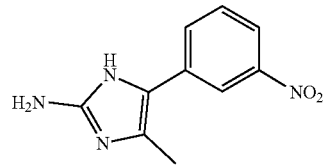 [SMILES: Cc1nc(N)[nH]c1-c1cccc([N+](=O)[O-])c1]

Took up 3-methyl-2-(3-nitrophenyl)imidazo[1,2-a]pyridine hydrobromide salt (1 eq) in EtOH and added hydrazine monohydrate (7 eq). Heated the reaction to a mild reflux for 2 hr. Concentrated to remove EtOH; took up the residue in a dilute sodium bicarbonate solution and extracted with a EtOAc. Dried the organic extracts over sodium sulfate; removed the drying salts by filtration and concentrated the filtrate to dryness. Triturated the residue in DCM; collected the solids on filter and air-dried to obtain the title compound.

Step 4: 4-(3-nitrophenyl)-5-methyl-2-(N,N-bis-tert-butoxycarbonylamino)-1H-imidazole-3-tert-butoxycarbonyl

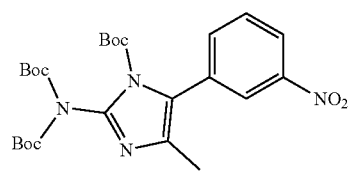

Dissolved 4-(3-nitrophenyl)-5-methyl-1H-imidazol-2-amine (1 eq) in THF and added Boc-anhydride (4 eq) and DMAP (0.1 eq). The reaction was stirred overnight at rt. Concentrated the reaction in a hot water bath to remove solvent and some of the excess Boc-anhydride. Dissolved the residue in DCM and loaded onto a silica gel pad. Eluted the desired product with 20% EtOAc in hexanes. Concentrated the desired fractions to dryness to obtain the title compound.

Step 5: 4-(3-aminophenyl)-5-methyl-2-(N,N-bis-tert-butoxycarbonylamino)-1H-imidazole-3-tert-butoxycarbonyl

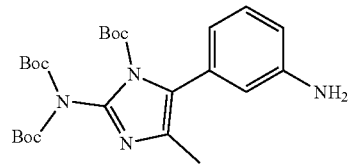 [SMILES: Cc1nc(N(C(=O)OC(C)(C)C)C(=O)OC(C)(C)C)n(C(=O)OC(C)(C)C)c1-c1cccc(N)c1]

Dissolved 4-(3-nitrophenyl)-5-methyl-2-(N,N-bis-tert-butoxycarbonylamino)-1H-imidazole-3-tert-butoxycarbonyl (1 mass) in THF and placed under a nitrogen atmosphere. To this was added 10% Pd/C (10 mass %) and the nitrogen atmosphere was replaced with a hydrogen atmosphere. The reaction was stirred at r.t. until the starting material was consumed. The reaction was filtered through Celite. The filtrate was concentrated to dryness and purified by silica gel chromatography. The desired fractions were concentrated to a yellow oil which was triturated with a mixture of diethyl ether and hexanes. The resulting solids were collected on filter and air-dried to provide the title compound as a white powder.

Synthesis of Key Intermediate C: 5-(3-amino-4-fluorophenyl)-2-(N,N-bis-tert-butoxycarbonylamino)-1H-imidazole-1-tert-butoxycarbonyl

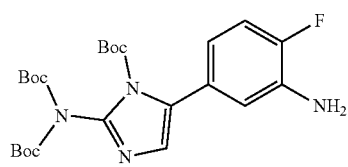 [SMILES: CC(C)(C)OC(=O)N(C(=O)OC(C)(C)C)c1ncc(-c2ccc(F)c(N)c2)n1C(=O)OC(C)(C)C]

Step 1: 2-bromo-1-(3-nitro-4-fluorophenyl)-ethan-1-one

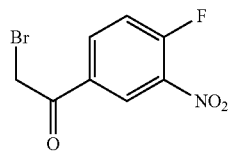 [SMILES: O=C(CBr)c1ccc(F)c([N+](=O)[O-])c1]

Dissolved 1-(3-nitro-4-fluorophenyl)-ethan-1-one (1 eq) in THF and added bromine (1.1 eq) in a dropwise fashion. Stirred at r.t. until starting material was consumed by TLC (about 2 hr). Diluted the reaction with ether and washed the organics with a dilute solution of sodium bicarbonate. Dried the organics over sodium sulfate; removed the drying salts by filtration and concentrated the filtrate to dryness to obtain the title compound as a yellow oil.

Step 2: Synthesis of Tert-butyl-2-amino-5-(3-nitro-4-fluorophenyl)-1H-imidazole-1-carboxylate

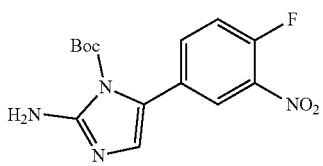 [SMILES: CC(C)(C)OC(=O)n1c(-c2ccc(F)c([N+](=O)[O-])c2)cnc1N]

In THF was dissolved 2-bromo-3'-nitro-4-fluoroacetophenone (1 eq). To this was added Boc-guanidine (2 eq) and the reaction was stirred at 56 C until starting material was consumed (about 2 hr). The reaction was diluted with diethyl ether and water. The organic layer was collected; dried over sodium sulfate and the drying salts were removed by filtration. The filtrate was concentrated to dryness and the residue triturated in ethyl acetate. The solids were collected on a filter, washed with diethyl ether and dried to provide the desired material as a yellow-orange powder.

Step 3: Synthesis of 5-(3-nitro-4-fluorophenyl)-2-(N,N-bis-tert-butoxycarbonylamino)-1H-imidazole-1-tert-butoxycarbonyl

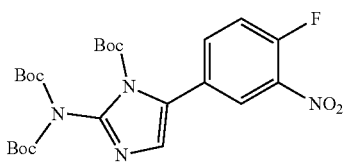 [SMILES: CC(C)(C)OC(=O)N(C(=O)OC(C)(C)C)c1ncc(-c2ccc(F)c(N)c2)n1C(=O)OC(C)(C)C]

Dissolved tert-butyl-2-amino-5-(3-nitro-4-fluorophenyl)-1H-imidazole-1-carboxylate (1 eq) in THF and treated with $(Boc)_2O$ (56.3 g, 3 eq). The mixture was then treated with DMAP (2.1 g, 0.2 eq) and stirred overnight at r.t. Concentrated the reaction to dryness and purified the residue by silica gel chromatography to obtain the desired product as a yellow oil.

Step 4: Synthesis of 5-(3-amino-4-fluorophenyl)-2-(N,N-bis-tert-butoxycarbonylamino)-1H-imidazole-1-tert-butoxycarbonyl

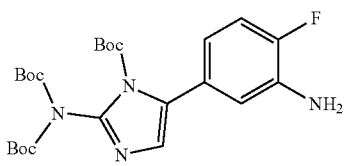

Dissolved 5-(3-nitro-4-fluorophenyl)-2-(N,N-bis-tert-butoxycarbonylamino)-1H-imidazole-1-tert-butoxycarbonyl in ethyl acetate and placed under a nitrogen atmosphere. To this was added 10% Pd/C (0.1 mass) and the nitrogen atmosphere was replaced with a hydrogen atmosphere. The reaction was stirred at r.t. until the starting material was consumed (about 2 hr). The reaction was filtered through Celite and the filtrate was concentrated to dryness; dissolved in diethyl ether and reconcentrated. The residue was dissolved in minimal diethyl ether and allowed to sit overnight. The resulting crystals were collected on filter to provide the desired product as an off-white solid.

Synthesis of Key Intermediate D: 4-(3-amino-4-methoxyphenyl)-2-(N,N-bis-tert-butoxycarbonylamino)-1H-imidazole-3-tert-butoxycarbonyl

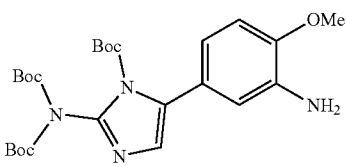

Step 1: 2-bromo-1-(3-nitro-4-methoxyphenyl)-ethan-1-one

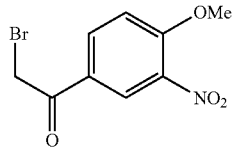 [SMILES: COc1ccc(C(=O)CBr)cc1[N+](=O)[O-]]

Dissolved 1-(3-nitro-4-methoxyphenyl)-ethan-1-one (1 eq) in THF and added bromine (1.1 eq) in a dropwise fashion. Stirred at r.t. until starting material was consumed by TLC (about 2 hr). Diluted the reaction with ether and washed the organics with a dilute solution of sodium bicarbonate. Dried the organics over sodium sulfate; removed the drying salts by filtration and concentrated the filtrate to dryness to obtain the title compound as a yellow oil.

Step 2: 2-(3-nitro-4-methoxyphenyl)imidazo[1,2-a]pyrimidine Hydrobromide Salt

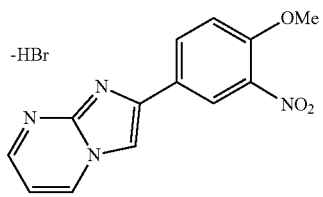 [SMILES: COc1ccc(-c2cn3cccnc3n2)cc1[N+](=O)[O-] ; "-HBr"]

In THF was dissolved 2-bromo-1-(3-nitro-4-methoxyphenyl)-ethan-1-one (1.1 eq). To this was added 2-aminopyrimidine (2 eq) and the reaction was heated in a microwave at 150 C for 1 hr. Collected the resulting solids on filter; washed the solids with THF and air-dried to obtain the title compound as a tan powder.

Step 3: 4-(3-nitro-4-methoxyphenyl)-2-(N,N-bis-tert-butoxycarbonylamino)-1H-imidazole-3-tert-butoxycarbonyl

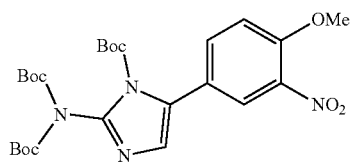 [SMILES: COc1ccc(-c2cnc(N(C(=O)OC(C)(C)C)C(=O)OC(C)(C)C)n2C(=O)OC(C)(C)C)cc1[N+](=O)[O-]]

Took up starting material (1 eq) in EtOH and added hydrazine monohydrate (7 eq). Heated the reaction to a mild reflux for 2 hr. Concentrated the reaction to remove solvents and took up the residue in water. Extracted the aqueous layer with ethyl acetate. Dried the extracts over sodium sulfate; removed the drying salts by filtration and concentrated the filtrate to dryness. Dissolved the residue in THF and added Boc-anhydride (4 eq) and DMAP (0.1 eq). Stirred the reaction overnight at rt. Concentrated the reaction to dryness. Purified the residue by silica gel chromatography to obtain the desired compound.

Step 4: 4-(3-amino-4-methoxyphenyl)-2-(N,N-bis-tert-butoxycarbonylamino)-1H-imidazole-3-tert-butoxycarbonyl

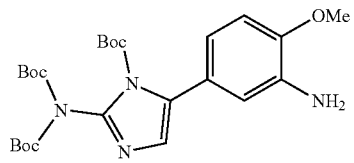

Dissolved 4-(3-nitro-4-methoxyphenyl)-2-(N,N-bis-tert-butoxycarbonylamino)-1H-imidazole-3-tert-butoxycarbonyl (1 mass) in THF and placed under a nitrogen atmosphere. To this was added 10% Pd/C (10 mass %) and the nitrogen atmosphere was replaced with a hydrogen atmosphere. The reaction was stirred at r.t. until the starting material was consumed. The reaction was filtered through Celite. The filtrate was concentrated to dryness and purified by silica gel chromatography to provide the title compound.

Synthesis of Key Intermediate E: 4-(3-aminophenyl)-5-phenyl-2-(N,N-bis-tert-butoxycarbonylamino)-1H-imidazole-3-tert-butoxycarbonyl

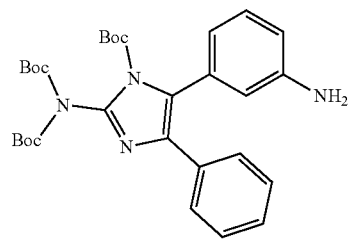 [SMILES: CC(C)(C)OC(=O)N(C(=O)OC(C)(C)C)c1nc(-c2ccccc2)c(-c2cccc(N)c2)n1C(=O)OC(C)(C)C]

Step 1: 4-(3-nitrophenyl)-5-bromo-2-(N,N-bis-tert-butoxycarbonylamino)-1H-imidazole-3-tert-butoxycarbonyl

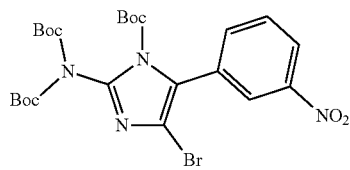 [SMILES: CC(C)(C)OC(=O)N(C(=O)OC(C)(C)C)c1nc(Br)c(-c2cccc([N+](=O)[O-])c2)n1C(=O)OC(C)(C)C]

Dissolved 5-(3-nitrophenyl)-2-(N,N-bis-tert-butoxycarbonylamino)-1H-imidazole-1-tert-butoxycarbonyl (1 eq, preparation described earlier) in THF and added solid sodium carbonate (2 eq) and N-bromosuccinimide (2 eq). Heated the reaction at 65 C overnight. Cooled to r.t., diluted the reaction with water and stirred vigorously for 5 min. Diluted the mixture with diethyl ether and collected the organic layer. Dried the organics over sodium sulfate; removed the drying agent by filtration and concentrated the filtrate to dryness to obtain the desired compound as a yellow liquid that solidified upon standing.

Step 2: 4-(3-nitrophenyl)-5-phenyl-2-(N,N-bis-tert-butoxycarbonylamino)-1H-imidazole-3-tert-butoxycarbonyl

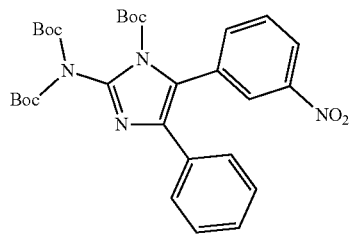 [SMILES: CC(C)(C)OC(=O)N(C(=O)OC(C)(C)C)c1nc(-c2ccccc2)c(-c2cccc([N+](=O)[O-])c2)n1C(=O)OC(C)(C)C]

In a microwave vial was combined 4-(3-nitrophenyl)-5-bromo-2-(N,N-bis-tert-butoxycarbonylamino)-1H-imidazole-3-tert-butoxycarbonyl (1 eq), phenyl boronic acid (1.5 eq), potassium carbonate (4 eq) and PdCl2(dppf)2 dichloromethane complex (0.2 eq) in dioxane. Added 10% water by volume and sonicated the mixture for 1 min. Heated the reaction in a microwave reactor at 140 C for 10 min. Diluted the reaction with water and extracted the aqueous layer with ethyl acetate. Filtered the mixture through Celite; collected the organic layer and dried over sodium sulfate. Removed the drying salts by filtration and concentrated the filtrate to dryness. Dissolved the crude material in THF and added Boc-anhydride (5 eq) and DMAP (0.5 eq). Stirred the reaction at r.t. overnight; concentrated the reaction to dryness and purified the residue by silica gel chromatography. Concentrated the desired fractions to obtain the title compound as a yellow oil.

Step 3: 4-(3-aminophenyl)-5-phenyl-2-(N,N-bis-tert-butoxycarbonylamino)-1H-imidazole-3-tert-butoxycarbonyl

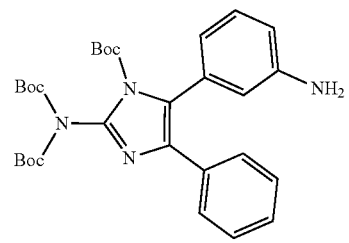 [SMILES: CC(C)(C)OC(=O)N(C(=O)OC(C)(C)C)c1nc(-c2ccccc2)c(-c2cccc(N)c2)n1C(=O)OC(C)(C)C]

Dissolved 4-(3-nitrophenyl)-5-phenyl-2-(N,N-bis-tert-butoxycarbonylamino)-1H-imidazole-3-tert-butoxycarbonyl (1 mass) in ethyl acetate and placed under a nitrogen atmosphere. Added 20 mass % of 10% Pd/C. Replaced the nitrogen atmosphere with hydrogen and heated the reaction to 45 C for 4 hr. Displaced the hydrogen atmosphere with nitrogen then filtered through Celite; washed the filter with ethyl acetate and concentrated the filtrate to dryness. Reconcentrated from diethyl ether to obtain the desired compound as a yellow foam.

Synthesis of Key Intermediate F: 5-(4-aminophenyl)-2-(N,N-bis-tert-butoxycarbonylamino)-1H-imidazole-1-tert-butoxycarbonyl

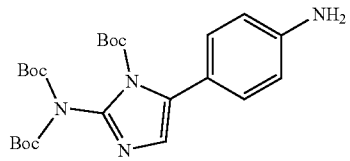 [SMILES: CC(C)(C)OC(=O)N(C(=O)OC(C)(C)C)c1ncc(-c2ccc(N)cc2)n1C(=O)OC(C)(C)C]

Step 1: 2-(4-nitrophenyl)imidazo[1,2-a]pyrimidine Hydrobromide Salt

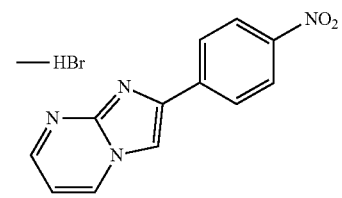

In CH$_3$CN was dissolved 2-bromo-4'-nitroacetophenone (1.1 eq). To this was added 2-aminopyrimidine (1 eq) and the reaction was stirred at rt until homogeneous. Added DMAP (0.1 eq) and heated to a mild reflux for 5 hr. Cooled to rt; collected the solids on filter; washed the solids with CH3CN and air-dried to obtain the title compound as a tan powder.

Step 2: 5-(4-nitrophenyl)-1H-imidazol-2-amine

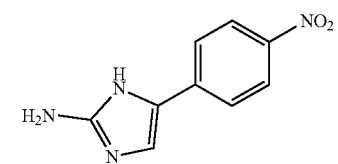 [SMILES: Nc1ncc(-c2ccc([N+](=O)[O-])cc2)[nH]1]

Took up starting material (1 eq) in EtOH and added hydrazine monohydrate (7 eq). Heated the reaction to a mild reflux for 6 hr. Cooled to rt and collected the solids on filter. Concentrated the filtrate to dryness; took up the residue in a dilute sodium bicarbonate solution and extracted with a 5% MeOH in ethyl acetate solution. Dried the organic extracts over sodium sulfate; removed the drying salts by filtration and concentrated the filtrate to dryness. Triturated in diethyl ether; collected the solids on filter and combined them with the solids collected earlier to provide the desired material.

Step 3: 5-(4-nitrophenyl)-2-(N,N-bis-tert-butoxycarbonylamino)-1H-imidazole-1-tert-butoxycarbonyl

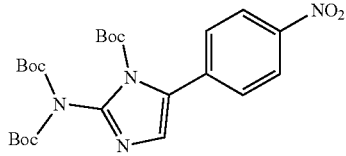 [SMILES: CC(C)(C)OC(=O)N(C(=O)OC(C)(C)C)c1ncc(-c2ccc([N+](=O)[O-])cc2)n1C(=O)OC(C)(C)C]

Dissolved 5-(4-nitrophenyl)-1H-imidazol-2-amine (1 eq) in THF and added Boc-anhydride (4 eq) and DMAP (0.1 eq). The reaction was stirred overnight at rt. Concentrated the reaction in a hot water bath to remove solvent and some of the excess Boc-anhydride. Allowed the residue to sit overnight at rt, upon which time solids formed. Triturated the residue in a 6% THF in hexanes solution. Collected the solids on filter and air-dried to obtain the title compound as a tan powder.

Step 4: 5-(4-aminophenyl)-2-(N,N-bis-tert-butoxycarbonylamino)-1H-imidazole-1-tert-butoxycarbonyl

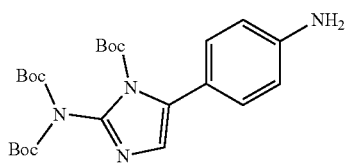

Dissolved 5-(4-nitrophenyl)-2-(N,N-bis-tert-butoxycarbonylamino)-1H-imidazole-1-tert-butoxycarbonyl (1 mass) in THF and placed under a nitrogen atmosphere. To this was added 10% Pd/C (10 mass %) and the nitrogen atmosphere was replaced with a hydrogen atmosphere. The reaction was stirred at r.t. until the starting material was consumed. The reaction was filtered through Celite. The filtrate was concentrated to dryness and dissolved in diethyl ether. Precipitation was induced by partially concentrating the solution without external heat. The mixture was allowed to stir at r.t. for 1 hr, then sonicated and the solids were collected on filter. Washed the solids with diethyl ether and air-dried to obtain the desired product as an off-white solid.

Synthesis of Key Intermediates G and H

Key Intermediate G: 8-amino-2-(N,N-bis-tert-butoxycarbonylamino)-4,5-dihydro-1H-naphtho[1,2-d]imidazole-1-tert-butoxycarbonyl

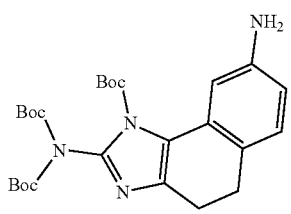

Key Intermediate H: 8-amino-2-(N,N-bis-tert-butoxycarbonylamino)-1H-naphtho[1,2-d]imidazole-1-tert-butoxycarbonyl

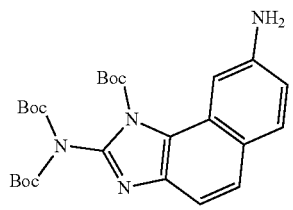 [SMILES: CC(C)(C)OC(=O)N(C(=O)OC(C)(C)C)c1nc2ccc3ccc(N)cc3c2n1C(=O)OC(C)(C)C]

Step 1: 2-bromo-7-nitro-1-tetralone

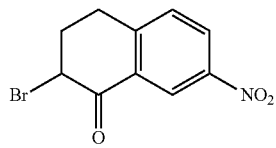 [SMILES: O=C1c2cc([N+](=O)[O-])ccc2CCC1Br]

Dissolved 7-nitro-1-tetralone (1 eq) in THF and added bromine (1.1 eq). Stirred at r.t. for about 2 hr. Diluted with diethyl ether and washed with a dilute solution of sodium bicarbonate. Collected the organics and dried over sodium sulfate; removed the drying agent by filtration and concentrated the filtrate to dryness. Purified the residue by silica gel chromatography to obtain the desired material as a tan powder.

Step 2: 2-nitro-5,6-dihydronaphtho[1',2':4,5]imidazo[1,2-a]pyrimidine Hydrobromide Salt

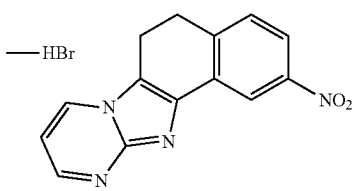

Dissolved 2-bromo-7-nitro-1-tetralone (1 g, 3.7 mmol) and 2-aminopyrimidine (1 wt) in CH$_3$CN. Heated in a microwave at 145 C for 7 hr. Sonicated, then stirred at r.t. for 1 hr. Collected solids on filter and washed with CH$_3$CN. Air-dried to obtain the title compound as a dark yellow powder.

Step 3: 8-nitro-2-(N,N-bis-tert-butoxycarbo-
nylamino)-4,5-dihydro-1H-naphtho[1,2-d]imidazole-
1-tert-butoxycarbonyl

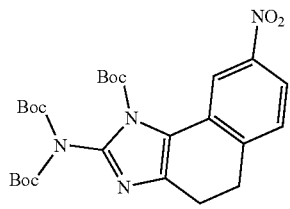 [SMILES: CC(C)(C)OC(=O)N(C(=O)OC(C)(C)C)c1nc2c(n1C(=O)OC(C)(C)C)-c1cc([N+](=O)[O-])ccc1CC2]

Took up 2-nitro-5,6-dihydronaphtho[1',2':4,5]imidazo[1,2-a]pyrimidine hydrobromide salt (1 eq) in EtOH. Added hydrazine monohydrate (7 eq) and heated in microwave at 100 C for 30 min. Conc. to remove EtOH and took up the residue in water. Extracted with EtOAc. Dried extracts over sodium sulfate; removed drying salts by filtration and concentrated the filtrate to dryness. Dissolved the residue in THF and added Boc2O (4 eq) and DMAP (1 eq). Stirred at rt overnight. Concentrated to dryness and took up residue in DCM and purified by silica gel chromatography. Concentrated the desired fractions to dryness and triturated the residue in diethyl ether. Collected solids on filter to obtain the title compound as a yellow powder.

Step 4: 8-amino-2-(N,N-bis-tert-butoxycarbo-
nylamino)-4,5-dihydro-1H-naphtho[1,2-d]imidazole-
1-tert-butoxycarbonyl And 8-amino-2-(N,N-bis-tert-butoxycarbonylamino)-1H-
naphtho[1,2-d]imidazole-1-tert-butoxycarbonyl

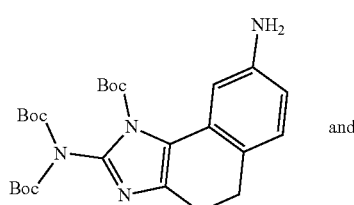

and

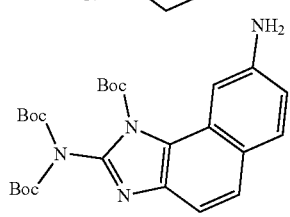

Took up 8-nitro-2-(N,N-bis-tert-butoxycarbonylamino)-4,5-dihydro-1H-naphtho[1,2-d]imidazole-1-tert-butoxycarbonyl in 1:1 EtOAc/MeOH (used heat and sonication to effect dissolution). Placed the solution under a nitrogen atmosphere and added 10% Pd/C (1 mass). Replaced the nitrogen atmosphere with hydrogen and stirred at r.t. for 1 hr. Filtered to remove Pd and concentrated the filtrate to dryness. This resulted in a bright blue less polar spot and a darker more polar spot. The darker spot is Key Intermediate G. The less polar light blue spot is Key Intermediate H.

Purified the residue by silica gel chromatography to separate the compounds which were isolated as regioisomeric mixtures of Boc-protected imidazole nitrogens.

Synthesis of Key Intermediate J: 6-amino-2-(N,N-
bis-tert-butoxycarbonylamino)-4,5-dihydro-1H-
naphtho[1,2-d]imidazole-1-tert-butoxycarbonyl

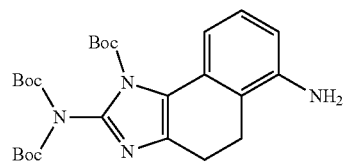 [SMILES: CC(C)(C)OC(=O)N(C(=O)OC(C)(C)C)c1nc2c(n1C(=O)OC(C)(C)C)-c1cccc(N)c1CC2]

Step 1: 2-bromo-5-nitro-1-tetralone

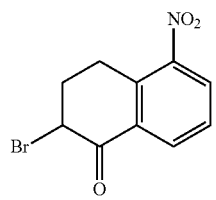 [SMILES: O=C1c2cccc([N+](=O)[O-])c2CCC1Br]

Dissolved 5-nitro-1-tetralone (1 eq) in THF and added bromine (1.1 eq). Stirred at r.t. for about 2 hr. Diluted with diethyl ether and washed with a dilute solution of sodium bicarbonate. Collected the organics and dried over sodium sulfate; removed the drying agent by filtration and concentrated the filtrate to dryness. Allowed the residue to sit overnight to solidify. Covered the solids in diethyl ether and crushed the solids with a glass rod. Collected the resulting powder on filter to obtain the desired product as a tan powder.

Step 2: 4-nitro-5,6-dihydronaphtho[1',2':4,5]imidazo
[1,2-a]pyrimidine Hydrobromide Salt

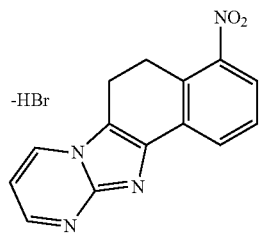

Dissolved 2-bromo-5-nitro-3,4-dihydronaphthalen-1(2H)-one (1 g, 3.7 mmol) and 2-aminopyrimidine (5 eq) in acetonitrile. Heated in a microwave at 150 C for 3 hr. Diluted the reaction with ethyl acetate and stirred at r.t. overnight. Collected solids on filter and washed with ethyl acetate. Air-dried to obtain the title compound as a tan powder.

Step 3: 6-nitro-2-(N,N-bis-tert-butoxycarbonylamino)-4,5-dihydro-1H-naphtho[1,2-d]imidazole-1-tert-butoxycarbonyl

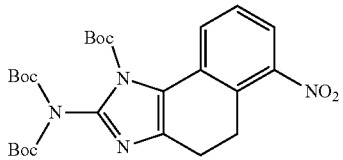 [SMILES: CC(C)(C)OC(=O)N(C(=O)OC(C)(C)C)c1nc2c(n1C(=O)OC(C)(C)C)-c1cccc([N+](=O)[O-])c1CC2]

Took up 4-nitro-5,6-dihydronaphtho[1',2':4,5]imidazo[1,2-a]pyrimidine hydrobromide salt (1 eq) in EtOH. Added hydrazine monohydrate (7 eq) and heated in microwave at 100 C for 10 min. Conc. to remove EtOH and took up the residue in water. Extracted with EtOAc. Dried extracts over sodium sulfate; removed drying salts by filtration and concentrated the filtrate to dryness. Dissolved the residue in THF and added Boc2O (4 eq) and DMAP (1 eq). Stirred at rt overnight. Concentrated to dryness and took up residue in DCM and purified by silica gel chromatography. Concentrated the desired fractions to dryness and triturated the residue in diethyl ether. Collected solids on filter to obtain the title compound as a yellow powder.

Step 4: 6-amino-2-(N,N-bis-tert-butoxycarbonylamino)-4,5-dihydro-1H-naphtho[1,2-d]imidazole-1-tert-butoxycarbonyl

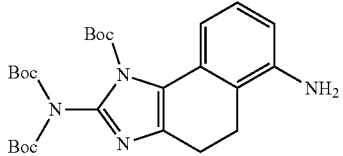

Took up 6-nitro-2-(N,N-bis-tert-butoxycarbonylamino)-4,5-dihydro-1H-naphtho[1,2-d]imidazole-1-tert-butoxycarbonyl in 1:1 EtOAc/MeOH (used heat and sonication to effect dissolution). Placed the solution under a nitrogen atmosphere and added 10% Pd/C (1 mass). Replaced the nitrogen atmosphere with hydrogen and stirred at r.t. for 1 hr. Filtered to remove Pd and concentrated the filtrate to dryness. Purified the residue by chromatography and concentrated the desired fractions to obtain the title compound as an off-white powder.

General Procedure for the Preparation of 1-(3-(2-amino-1H-imidazol-5-yl)phenyl)-3-phenylureas

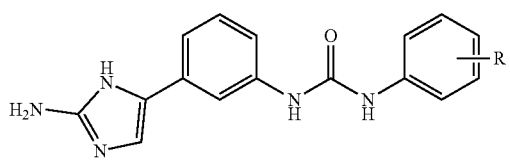

Method A: From a Key Intermediate and a Phenylisocyanate

Dissolved the Key Intermediate (1 eq) in THF and added a THF solution of the phenylisocyanate (1.2 eq). Stirred at r.t. until the Key Intermediate had been consumed. Concentrated the reaction to remove THF and took up the residue in DCM. Added an equal volume of TFA and stirred at r.t. for 3 hr. Concentrated to dryness and reconcentrated from DCM/MeOH. Triturated the residue in an appropriate solvent and collected the solids on filter to obtain the desired product as a TFA salt. If trituration did not produce a solid, then the residue was purified by silica gel chromatography using a mixture of DCM/MeOH/NH$_3$ to elute the product, providing the desired material as a free base.

The following compounds were prepared from Key Intermediate A and the appropriate isocyanate:

Compound 13: 1-(3-(2-amino-1H-imidazol-5-yl)phenyl)-3-(3-chloro-4-fluorophenyl)urea: $^1$H NMR (d$_6$-DMSO): 12.65 ppm (br s, 1H), 12.17 ppm (br s, 1H), 9.24 ppm (s, 1H), 9.10 ppm (s, 1H), 7.89-7.77 ppm (m, 2H), 7.50 ppm (s, 2H), 7.42-7.22 ppm (m, 5H)

Compound 30: 1-(3-(2-amino-1H-imidazol-5-yl)phenyl)-3-(4-chlorophenyl)urea: $^1$H NMR (d$_6$-DMSO): 12.72 ppm (br s, 1H), 12.16 ppm (br s, 1H), 9.16 ppm (s, 1H), 9.03 ppm (s, 1H), 7.79 ppm (s, 1H), 7.51 ppm (t, J=6 Hz, 4H), 7.40-7.20 ppm (m, 6H)

Compound 89: 1-(3-(2-amino-1H-imidazol-5-yl)phenyl)-3-hexylurea: $^1$H NMR (d$_6$-DMSO): 12.44 ppm (br s, 1H), 8.56 ppm (s, 1H), 7.72 ppm (s, 1H), 7.50 ppm (s, 2H), 7.34-7.09 ppm (m, 4H), 6.32 ppm (t, J=6 Hz, 1H), 3.08 ppm (dd, J=6, 12 Hz, 2H), 1.46-1.22 ppm (m, 8H), 0.87 ppm (t, J=6 Hz, 3H)

Compound 1: 1-(3-(2-amino-1H-imidazol-5-yl)phenyl)-3-(4-butylphenyl)urea: $^1$H NMR (d$_6$-DMSO): 12.67 ppm (br s, 1H), 12.10 ppm (br s, 1H), 8.80 ppm (s, 1H), 8.77 ppm (s, 1H), 7.71 ppm (s, 1H), 7.44 ppm (s, 2H), 7.34-7.19 ppm (m, 5H), 7.14 ppm (d, J=6 Hz, 1H), 7.02 ppm (d, J=9 Hz, 2H), 2.48-2.39 ppm (m, 2H), 1.53-1.36 ppm (m, 2H), 1.30-1.13 ppm (m, 2H), 0.83 ppm (t, J=9 Hz, 3H)

Compound 3: 1-(3-(2-amino-1H-imidazol-5-yl)phenyl)-3-(3,4-dichlorophenyl)urea: $^1$H NMR (d$_6$-DMSO): 12.60 ppm (br s, 1H), 12.15 ppm (br s, 1H), 9.37 ppm (s, 1H), 9.15 ppm (s, 1H), 7.87 ppm (d, J=3 Hz, 1H), 7.75 ppm (s, 1H), 7.45 ppm (m, 3H), 7.35-7.13 ppm (m, 5H)

Compound 42: 1-(3-(2-amino-1H-imidazol-5-yl)phenyl)-3-(4-(tert-butyl)phenyl)urea: $^1$H NMR (d$_6$-DMSO): 9.22 ppm (s, 1H), 9.18 ppm (s, 1H), 7.66 ppm (s, 1H), 7.34-7.10 ppm (m, 12H), 1.18 ppm (s, 9H)

Compound 4: 1-(3-(2-amino-1H-imidazol-5-yl)phenyl)-3-(4-chloro-3-(trifluoromethyl)phenyl)urea: $^1$H NMR (d$_6$-DMSO): 12.64 ppm (br s, 1H), 12.07 ppm (br s, 1H), 9.47 ppm (s, 1H), 9.13 ppm (s, 1H), 8.10 ppm (s, 1H), 7.74 ppm (s, 1H), 7.55 ppm (s, 2H), 7.41 ppm (s, 2H), 7.41-7.18 pmm (m, 4H)

Compound 47: 1-(3-(2-amino-1H-imidazol-5-yl)phenyl)-3-(4-chloro-3-nitrophenyl)urea: $^1$H NMR (d$_6$-DMSO): 12.20 ppm (br s, 2H), 9.65 ppm (s, 1H), 9.25 ppm (s, 1H), 8.305 ppm (d, J=3 Hz, 1H), 7.76 ppm (s, 1H), 7.65-7.50 ppm (m, 2H), 7.42 ppm (s, 2H), 7.35-7.15 ppm (m, 5H)

Compound 48: 1-(3-(2-amino-1H-imidazol-5-yl)phenyl)-3-(4-chloro-3-methylphenyl)urea: $^1$H NMR (d$_6$-DMSO): 12.37 ppm (br s, 1H), 8.995 ppm (d, J=2 Hz, 2H), 7.74 ppm (t, J=3 Hz, 1H), 7.665 ppm (d, J=3 Hz, 2H), 7.41 ppm (s, 2H), 7.33-7.06 ppm (m, 6H), 2.18 ppm (s, 3H)

Compound 52: 1-(3-(2-amino-1H-imidazol-5-yl)phenyl)-3-(3,4-dimethoxyphenyl)urea: $^1$H NMR (d$_6$-DMSO): 12.69 ppm (br s, 1H), 12.11 ppm (br s, 1H), 8.76 ppm (s, 1H), 8.71 ppm (s, 1H), 7.70 ppm (s, 1H), 7.44 ppm (s, 2H), 7.34-7.10 ppm (m, 5H), 6.81 ppm (d, J=3 Hz, 2H), 3.66 ppm (s, 3H), 3.62 ppm (s, 3H)

Compound 41: 1-(3-(2-amino-1H-imidazol-5-yl)phenyl)-3-(3,4-dimethylphenyl)urea: $^1$H NMR ($d_6$-DMSO): 12.63 ppm (br s, 1H), 12.11 ppm (br s, 1H), 8.72 ppm (d, J=36 Hz, 2H), 7.72 ppm (s, 1H), 7.43 ppm (s, 2H), 7.32-7.05 ppm (m, 6H), 6.945 ppm (d, J=9 Hz, 1H), 2.12 ppm (s, 3H), 2.08 ppm (s, 3H)

Compound 53: 1-(3-(2-amino-1H-imidazol-5-yl)phenyl)-3-(benzo[d][1,3]dioxol-5-yl)urea: $^1$H NMR ($d_6$-DMSO): 12.57 ppm (br s, 1H), 12.11 ppm (br s, 1H), 8.80 ppm (s, 1H), 8.76 ppm (s, 1H), 7.69 ppm (s, 1H), 7.42 ppm (s, 2H), 7.32-7.07 ppm (m, 5H), 6.80-6.65 ppm (m, 2H), 5.89 ppm (s, 2H)

Compound 54: 1-(3-(2-amino-1H-imidazol-5-yl)phenyl)-3-(2,3-dihydrobenzo[b][1,4]dioxin-6-yl)urea: $^1$H NMR ($d_6$-DMSO): 13.03-11.40 ppm (br s, 2H), 8.73 ppm (s, 1H), 8.64 ppm (s, 1H), 7.69 ppm (s, 1H), 7.40 ppm (br s, 2H), 7.31-7.08 ppm (m, 4H), 7.02 ppm (s, 1H), 6.80-6.63 ppm (m, 2H), 4.12 ppm (m, 4H)

Compound 33: 1-(3-(2-amino-1H-imidazol-5-yl)phenyl)-3-(3,5-dichlorophenyl)urea: $^1$H NMR ($d_6$-DMSO): 12.36 ppm (br s, 2H), 9.46 ppm (s, 1H), 9.25 ppm (s, 1H), 7.76 ppm (s, 1H), 7.50 ppm (t, J=3 Hz, 2H), 7.43 ppm (s, 2H), 7.35-7.15 ppm (m, 4H), 7.11-7.07 ppm (m, 1H)

Compound 34: 1-(3-(2-amino-1H-imidazol-5-yl)phenyl)-3-(3,4-dibromophenyl)urea: $^1$H NMR ($d_6$-DMSO): 12.62 ppm (br s, 1H), 12.11 ppm (br s, 1H), 9.30 ppm (s, 1H), 9.11 (s, 1H), 8.02 ppm (d, J=3 Hz, 1H), 7.75 ppm (s, 1H), 7.56 ppm (d, J=9 Hz, 1H), 7.42 ppm (br s, 2H), 7.33-7.14 ppm (br s, 5H)

Compound 35: 1-(3-(2-amino-1H-imidazol-5-yl)phenyl)-3-(3-chloro-4-methylphenyl)urea: $^1$H NMR ($d_6$-DMSO): 12.66 ppm (br s, 1H), 12.10 ppm (br s, 1H), 9.05 ppm (s, 1H), 8.97 ppm (s, 1H), 7.74 ppm (s, 1H), 7.67 ppm (d, J=3 Hz, 1H), 7.43 ppm (br s, 2H), 7.31-7.09 ppm (m, 6H), 2.18 ppm (s, 3H)

Compound 36: 1-(3-(2-amino-1H-imidazol-5-yl)phenyl)-3-(4-methyl-3-(trifluoromethyl)phenyl)urea: $^1$H NMR ($d_6$-DMSO): 12.37 ppm (br s, 2H), 9.22 ppm (s, 1H), 9.03 ppm (s, 1H), 7.91 ppm (s, 1H), 7.75 ppm (s, 1H), 7.44 ppm (s, 3H), 7.31-7.11 ppm (m, 5H), 2.31 ppm (s, 3H)

Compound 39: 1-(3-(2-amino-1H-imidazol-5-yl)phenyl)-3-(4-ethylphenyl)urea: $^1$H NMR ($d_6$-DMSO): 12.47 ppm (br s, 1H), 9.44 ppm (s, 1H), 9.38 ppm (s, 1H), 7.66 ppm (s, 1H), 7.38-7.09 ppm (m, 7H), 7.025 ppm (d, J=9 Hz, 3H), 2.48 ppm (q, J=6 Hz, 2H), 1.08 ppm (t, J=6, 3H)

Compound 40: 1-(3-(2-amino-1H-imidazol-5-yl)phenyl)-3-(4-benzylphenyl)urea: $^1$H NMR ($d_6$-DMSO): 12.67 ppm (br s, 1H), 12.16 ppm (br s, 1H), 8.80 ppm (d, J=6 Hz, 2H), 7.70 ppm (s, 1H), 7.43 ppm (s, 2H), 7.35-7.02 ppm (m, 13H), 3.80 ppm (s, 2H)

Compound 43: 1-(3-(2-amino-1H-imidazol-5-yl)phenyl)-3-(2,4-dimethylphenyl)urea: $^1$H NMR ($d_6$-DMSO): 12.70 ppm (br s, 1H), 12.10 ppm (br s, 1H), 9.02 ppm (s, 1H), 7.92 ppm (s, 1H), 7.72 ppm (s, 1H), 7.57 ppm (d, J=9 Hz, 1H), 7.45 ppm (br s, 2H), 7.32-7.11 ppm (m, 4H), 6.89 ppm (t, J=9 Hz, 2H), 2.16 ppm (s, 3H), 2.12 ppm (s, 3H)

Compound 44: 1-(3-(2-amino-1H-imidazol-5-yl)phenyl)-3-mesitylurea: $^1$H NMR ($d_6$-DMSO): 12.65 ppm (br s, 1H), 12.13 ppm (br s, 1H), 8.78 ppm (br s, 1H), 7.75 ppm (s, 1H), 7.67 ppm (s, 1H), 7.42 ppm (br s, 2H), 7.30-7.06 ppm (m, 4H), 6.81 ppm (br s, 2H), 2.15 ppm (s, 3H), 2.09 ppm (s, 6H)

Compound 45: 1-(3-(2-amino-1H-imidazol-5-yl)phenyl)-3-(3-fluoro-4-methylphenyl)urea: $^1$H NMR ($d_6$-DMSO): 12.63 ppm (br s, 1H), 12.09 ppm (br s, 1H), 9.03 ppm (s, 1H), 8.92 ppm (s, 1H), 7.71 ppm (s, 1H), 7.55-6.80 ppm (m, 9H), 2.14 ppm (s, 3H)

Compound 46: 1-(3-(2-amino-1H-imidazol-5-yl)phenyl)-3-(3,4,5-trifluorophenyl)urea: $^1$H NMR ($d_6$-DMSO): 12.69 ppm (s, 1H), 12.10 ppm (s, 1H), 9.42 ppm (s, 1H), 9.20 ppm (s, 1H), 7.71 ppm (s, 1H), 7.45 ppm (s, 1H), 7.42-7.14 ppm (m, 7H)

Compound 25: 1-(3-(2-amino-1H-imidazol-5-yl)phenyl)-3-(4-butyl-2-methylphenyl)urea: $^1$H NMR ($d_6$-DMSO): 12.68 ppm (br s, 1H), 12.08 ppm (br s, 1H), 9.02 ppm (s, 1H), 7.91 ppm (s, 1H), 7.71 ppm (s, 1H), 7.57 ppm (d, J=6 Hz, 1H), 7.44 ppm (br s, 2H), 7.32-7.10 ppm (m, 4H), 6.98-6.82 ppm (m, 2H), 5.27 ppm (br s, 2H), 2.44 ppm (t, J=9 Hz, 2H), 2.13 ppm (s, 3H), 1.45 ppm (m, 2H), 1.22 ppm (m, 2H), 0.81 ppm (t, J=9 Hz, 3H)

Compound 2: 1-(3-(2-amino-1H-imidazol-5-yl)phenyl)-3-(4-propylphenyl)urea: $^1$H NMR ($d_6$-DMSO): 12.65 ppm (br s, 1H), 12.07 ppm (br s, 1H), 8.78 ppm (s, 1H), 8.73 ppm (s, 1H), 7.71 ppm (s, 1H), 7.42 ppm (s, 2H), 7.34-7.19 ppm (m, 5H), 7.14 ppm (d, J=6 Hz, 1H), 7.02 ppm (d, J=9 Hz, 2H), 2.42 ppm (t, J=9 Hz, 2H), 1.48 ppm (m, 2H), 0.81 ppm (t, J=9 Hz, 3H)

Compound 38: 1-(3-(2-amino-1H-imidazol-5-yl)phenyl)-3-(p-tolyl)urea: $^1$H NMR ($d_6$-DMSO): 12.68 ppm (s, 1H), 12.10 ppm (s, 1H), 8.79 ppm (d, J=18 Hz, 2H), 7.71 ppm (s, 1H), 7.44 ppm (s, 2H), 7.34-6.96 ppm (m, 8H), 2.17 ppm (s, 3H)

Compound 7: 1-(3-(2-amino-1H-imidazol-5-yl)phenyl)-3-(3,5-dibromophenyl)urea: $^1$H NMR ($d_6$-DMSO): 12.55 ppm (br s, 1H), 12.11 ppm (br s, 1H), 9.33 ppm (s, 1H), 9.16 ppm (s, 1H), 7.76 ppm (s, 1H), 7.67 ppm (d, J=1 Hz, 2H), 7.40 ppm (s, 2H), 7.35-7.23 ppm (m, 3H), 7.19 ppm (d, J=9 Hz, 2H)

Compound 90: 1-(3-(2-amino-1H-imidazol-5-yl)phenyl)-3-cyclohexylurea: $^1$H NMR ($d_6$-DMSO): 12.62 ppm (s, 1H), 12.06 ppm (s, 1H), 8.36 ppm (s, 1H), 7.63 ppm (s, 1H), 7.41 ppm (s, 2H), 7.32-7.02 ppm (m, 4H), 6.18 ppm (d, J=9 Hz, 1H), 1.78-0.96 ppm (m, 11H)

Compound 15: 1-(3-(2-amino-1H-imidazol-5-yl)phenyl)-3-(4-bromo-3,5-dichlorophenyl)urea: $^1$H NMR ($d_6$-DMSO): 12.66 ppm (br s, 1H), 12.09 ppm (br s, 1H), 9.54 ppm (s, 1H), 9.31 ppm (s, 1H), 7.76 ppm (s, 1H), 7.70 ppm (s, 1H), 7.41 ppm (d, J=15 Hz, 2H), 7.34-7.15 ppm (m, 5H)

Compound 91: (This compound was prepared from an isothiocyanate under the same conditions) 1-(3-(2-amino-1H-imidazol-5-yl)phenyl)-3-(3,4-dichlorophenyl)thiourea: $^1$H NMR ($d_6$-DMSO): 12.67 ppm (br s, 1H), 12.11 ppm (br s, 1H), 10.10 ppm (s, 2H), 7.83 ppm (s, 1H), 7.65 (s, 1H), 7.56-7.45 ppm (m, 3H), 7.44-7.28 ppm (m, 4H), 7.23 ppm (dd, J=3, 9 Hz, 1H)

Compound 32: 1-(3-(2-amino-1H-imidazol-5-yl)phenyl)-3-(3,5-bis(trifluoromethyl)phenyl)urea: $^1$H NMR ($d_6$-DMSO): 12.60 ppm (s, 1H), 12.05 ppm (s, 1H), 9.67 ppm (s, 1H), 9.23 ppm (s, 1H), 8.09 ppm (s, 2H), 7.77 ppm (d, J=3 Hz, 1H), 7.57 ppm (s, 1H), 7.39 ppm (s, 2H), 7.34-7.17 ppm (m, 4H)

Compound 50: 1-(3-(2-amino-1H-imidazol-5-yl)phenyl)-3-(3-cyanophenyl)urea: $^1$H NMR ($d_6$-DMSO): 12.62 ppm (br s, 1H), 12.08 ppm (br s, 1H), 9.32 ppm (s, 1H), 9.11 ppm (s, 1H), 7.95 ppm (d, J=3 Hz, 1H), 7.75 ppm (d, J=3 Hz, 1H), 7.59 ppm (dd, J=3, 9 Hz, 1H), 7.53-7.11 ppm (m, 7H), 1.30 ppm (d, J=3 Hz, 1H)

Compound 51: 1-(3-(2-amino-1H-imidazol-5-yl)phenyl)-3-(4-cyanophenyl)urea: $^1$H NMR ($d_6$-DMSO): 12.67 ppm (br s, 1H), 12.08 ppm (br s, 1H), 9.62 ppm (s, 1H), 9.51 ppm (s, 1H), 9.16 ppm (s, 1H), 7.72 ppm (s, 1H), 7.70-7.52 ppm (m, 4H), 7.43 ppm (br s, 2H), 7.35-7.15 ppm (m, 3H)

Compound 23: 1-(3-(2-amino-1H-imidazol-5-yl)phenyl)-3-(4-(trifluoromethyl)phenyl)urea: $^1$H NMR (d$_6$-DMSO): 12.66 ppm (br s, 1H), 12.08 ppm (br s, 1H), 9.37 ppm (s, 1H), 9.06 ppm (s, 1H), 7.74 ppm (s, 1H), 7.59 ppm (q, J=6, 9 Hz, 4H), 7.43 ppm (s, 2H), 7.34-7.15 ppm (m, 4H)

Compound 24: 1-(3-(2-amino-1H-imidazol-5-yl)phenyl)-3-(3-(trifluoromethyl)phenyl)urea: $^1$H NMR (d$_6$-DMSO): 12.65 ppm (br s, 1H), 12.08 ppm (br s, 1H), 9.32 ppm (s, 1H), 9.05 ppm (s, 1H), 8.01 ppm (s, 1H), 7.77 ppm (s, 1H), 7.53-7.36 ppm (m, 4H), 7.34-7.14 ppm (m, 5H)

Compound 59: 1-(3-(2-amino-1H-imidazol-5-yl)phenyl)-3-(5-methyl-2-(trifluoromethyl)furan-3-yl)urea: $^1$H NMR (d$_6$-DMSO): 12.49 ppm (br s, 2H), 9.20 ppm (s, 1H), 8.43 ppm (s, 1H), 7.66 ppm (s, 1H), 7.45 ppm (br s, 2H), 7.36-7.12 ppm (m, 4H), 6.81 ppm (s, 1H), 2.23 ppm (s, 3H)

Compound 60: 1-(3-(2-amino-1H-imidazol-5-yl)phenyl)-3-(2,6-dichloropyridin-4-yl)urea: $^1$H NMR (d$_6$-DMSO): 12.33 ppm (br s, 2H), 10.03 ppm (s, 1H), 9.55 ppm (s, 1H), 7.74 ppm (s, 1H), 7.50 ppm (s, 2H), 7.40 ppm (s, 2H), 7.34-7.14 ppm (m, 4H)

Compound 49: methyl-4-(3-(3-(2-amino-1H-imidazol-5-yl)phenyl)ureido)benzoate: $^1$H NMR (d$_6$-DMSO): 12.67 ppm (s, 1H), 12.10 ppm (s, 1H), 9.39 ppm (s, 1H), 9.09 ppm (s, 1H), 7.82 ppm (d, J=6 Hz, 2H), 7.75 ppm (s, 1H), 7.55 ppm (d, J=12 Hz, 2H), 7.43 ppm (s, 2H), 7.34-7.13 ppm (m, 4H), 3.74 ppm (s, 3H)

Compound 55: 1-(3-(2-amino-1H-imidazol-5-yl)phenyl)-3-(benzo[b]thiophen-5-yl)urea: $^1$H NMR (d$_6$-DMSO): 12.69 ppm, (s, 1H), 12.10 ppm (s, 1H), 9.00 ppm (s, 1H), 8.92 ppm (s, 1H), 8.06 ppm (d, J=3 Hz, 1H), 7.79 ppm (t, J=9 Hz, 2H), 7.66 ppm (d, J=6 Hz, 1H) 7.44 ppm (br s, 2H), 7.34-7.20 ppm (m, 5H), 7.16 ppm (d, J=6 Hz, 1H)

Compound 29: 1-(3-(2-amino-1H-imidazol-5-yl)phenyl)-3-(2,3-dihydro-1H-inden-5-yl)urea: $^1$H NMR (d$_6$-DMSO): 12.43 ppm (br s, 2H), 8.78 ppm (s, 1H), 8.70 ppm (s, 1H), 7.72 ppm (s, 1H), 7.41 ppm (s, 2H), 7.33 ppm (s, 1H), 7.31-7.00 ppm (m, 6H), 2.87-2.56 ppm (m, 4H), 2.00-1.82 ppm (m, 2H)

Compound 31: 1-(3-(2-amino-1H-imidazol-5-yl)phenyl)-3-phenylurea: $^1$H NMR (d$_6$-DMSO): 12.66 ppm (br s, 1H), 12.12 ppm (br s, 1H), 8.88 ppm (d, J=3 Hz, 2H), 7.72 ppm (s, 1H), 7.55-7.12 ppm (m, 10H), 6.90 ppm (t, J=9 Hz, 1H)

The following compounds were prepared from Key Intermediate B and the appropriate isocyanate:

Compound 61: 1-(3-(2-amino-4-methyl-1H-imidazol-5-yl)phenyl)-3-(3,4-dichlorophenyl)urea: $^1$H NMR (d$_6$-DMSO): 12.26 ppm (br s, 1H), 12.11 ppm (s, 1H), 9.29 ppm (s, 1H), 9.18 ppm (s, 1H), 7.82 ppm (d, J=3 Hz, 1H), 7.64 ppm (s, 1H), 7.45 ppm (s, 1H), 7.42 ppm (s, 1H), 7.39-7.19 ppm (m, 4H), 6.99 ppm (d, J=9 Hz, 1H), 2.17 ppm (s, 3H)

Compound 62: 1-(3-(2-amino-4-methyl-1H-imidazol-5-yl)phenyl)-3-(4-chlorophenyl)urea: $^1$H NMR (d$_6$-DMSO): 12.30 ppm (s, 1H), 12.18 ppm (s, 1H), 9.10 ppm (d, J=3 Hz, 2H), 7.64 ppm (s, 1H), 7.53-7.21 ppm (m, 8H), 6.98 ppm (dd, J=3, 12.0 Hz, 1H), 2.16 ppm (s, 3H)

Compound 63: 1-(3-(2-amino-4-methyl-1H-imidazol-5-yl)phenyl)-3-(2-chloro-4-(trifluoromethyl)phenyl)urea: $^1$H NMR (d$_6$-DMSO): 12.38 ppm (s, 1H), 12.19 ppm (s, 1H), 9.71 ppm (s, 1H), 8.62 ppm (s, 1H), 8.38 ppm (d, J=9.7 Hz, 1H), 7.79 ppm (d, J=2.4 Hz, 1H), 7.62 ppm (t, J=7.3 Hz, 2H), 7.45-7.29 ppm (m, 4H), 7.25 ppm (d, J=7.3 Hz, 1H), 7.03 ppm (d, J=7.3 Hz, 1H), 2.17 ppm (s, 3H)

Compound 64: 1-(3-(2-amino-4-methyl-1H-imidazol-5-yl)phenyl)-3-(3-chloro-4-fluorophenyl)urea: $^1$H NMR (d$_6$-DMSO): 12.31 ppm (br s, 1H), 12.16 ppm (br s, 1H), 9.28 ppm (s, 1H), 9.19 ppm (s, 1H), 7.73 ppm (d, J=7.0 Hz, 1H), 7.64 ppm (s, 1H), 7.42-7.19 ppm (m, 6H), 6.98 ppm (d, J=7.0 Hz, 1H), 2.17 ppm (s, 3H)

Compound 65: 1-(3-(2-amino-4-methyl-1H-imidazol-5-yl)phenyl)-3-(3,5-dichlorophenyl)urea: $^1$H NMR (d$_6$-DMSO): 12.29 ppm (s, 1H), 12.17 ppm (s, 1H), 9.43 ppm (s, 1H), 9.38 ppm (s, 1H), 7.64 ppm (s, 1H), 7.47 ppm (d, J=2.3 Hz, 2H); 7.41-7.22 ppm (m, 3H), 7.07 ppm (t, J=2.3 Hz, 1H), 7.00 ppm (dd, J=2.3, 7.7 Hz, 1H), 2.17 ppm (s, 3H)

The following compounds were prepared from Key Intermediate C and the appropriate isocyanate:

Compound 79: 1-(5-(2-amino-1H-imidazol-5-yl)-2-fluorophenyl)-3-(3,4-dichlorophenyl)urea: $^1$H NMR (d$_6$-DMSO): 12.61 ppm (br s, 1H), 12.11 ppm (br s, 1H), 9.42 ppm (br s, 1H), 8.67 ppm (s, 1H), 8.21 ppm (dd, J=3.9 Hz, 1H), 7.89 ppm (d, J=3 Hz, 1H), 7.56-7.38 ppm (m, 3H), 7.34-7.15 ppm (m, 4H)

Compound 80: 1-(5-(2-amino-1H-imidazol-5-yl)-2-fluorophenyl)-3-(4-butylphenyl)urea: $^1$H NMR (d$_6$-DMSO): 12.65 ppm (br s, 1H), 12.10 ppm (br s, 1H), 8.99 ppm (s, 1H), 8.58 ppm (s, 1H), 8.28 ppm (d, J=6 Hz, 1H), 7.43 ppm (br s, 2H), 7.33-7.11 ppm (m, 5H), 7.03 ppm (d, J=6 Hz, 2H), 2.40 ppm (t, J=6 Hz, 2H), 1.45 ppm (m, 2H), 1.22 ppm (m, 2H), 0.81 ppm (t, J=6 Hz, 3H)

The following compound was prepared from Key Intermediate D and the appropriate isocyanate:

Compound 81: 1-(5-(2-amino-1H-imidazol-5-yl)-2-methoxyphenyl)-3-(3,4-dichlorophenyl)urea: $^1$H NMR (d$_6$-DMSO): 12.29 ppm (br s, 1H), 10.29 ppm (s, 1H), 8.53 ppm (s, 1H), 8.22 ppm (d, J=3 Hz, 1H), 7.89 ppm (d, J=3 Hz, 1H), 7.50-6.95 ppm (m, 7H), 3.80 ppm (s, 3H)

The following compounds were prepared from Key Intermediate E and the appropriate isocyanate:

Compound 72: 1-(3-(2-amino-4-phenyl-1H-imidazol-5-yl)phenyl)-3-(3,4-dichlorophenyl)urea: $^1$H NMR (d$_6$-DMSO): $^1$H NMR (d$_6$-DMSO): 12.69 ppm (br s, 2H), 9.29 ppm (s, 1H), 9.18 ppm (s, 1H), 7.81 ppm (s, 1H), 7.51-7.15 ppm (m, 12H), 6.90 ppm (d, J=9 Hz, 1H)

Compound 73: 1-(3-(2-amino-4-phenyl-1H-imidazol-5-yl)phenyl)-3-(3-chloro-4-(trifluoromethyl)phenyl)urea: $^1$H NMR (d$_6$-DMSO): 12.69 ppm (br s, 2H), 9.55 ppm (s, 1H), 9.23 ppm (s, 1H), 8.98 ppm (s, 1H), 7.84 ppm (s, 1H), 7.66 ppm (d, J=9 Hz, 1H), 7.56 ppm (s, 1H), 7.50-7.18 ppm (m, 8H), 6.92 ppm (d, J=9 Hz, 2H)

The following compound was prepared from Key Intermediate G and the appropriate isocyanate:

Compound 69: 1-(2-amino-4,5-dihydro-1H-naphtho[1,2-d]imidazol-8-yl)-3-(3,4-dichlorophenyl)urea: $^1$H NMR (d$_6$-DMSO): 12.67 ppm (s, 1H), 12.20 ppm (s, 1H), 9.23 ppm (s, 1H), 8.95 ppm (s, 1H), 7.88 ppm (t, J=3 Hz, 1H), 7.58 ppm (s, 1H), 7.51 ppm (s, 1H), 7.44 ppm (dd, J=3, 9 Hz, 2H), 7.28-7.20 ppm (m, 1H), 7.06 ppm (d, J=6 Hz, 1H), 6.97 ppm (d, J=6 Hz, 1H), 2.85 ppm (t, J=9 Hz, 2H), 2.62 ppm (t, J=9 Hz, 2H)

The following compound was prepared from Key Intermediate J and the appropriate isocyanate:

Compound 74: 1-(2-amino-4,5-dihydro-1H-naphtho[1,2-d]imidazol-6-yl)-3-(3,4-dichlorophenyl)urea: $^1$H NMR (d$_6$-DMSO): 12.72 ppm (br s, 1H), 12.22 ppm (br s, 1H), 9.29 ppm (s, 1H), 8.32 ppm (s, 1H), 7.82 ppm (d, J=3 Hz, 1H), 7.62 ppm (br s, 2H), 7.43 ppm (d, J=9 Hz, 1H), 7.37 ppm (dd, J=3, 9 Hz, 1H), 7.24 ppm (dd, J=3, 9 Hz, 1H), 7.17 ppm (s, 1H), 7.13 ppm (t, J=6 Hz, 1H), 2.86 ppm (t, J=9 Hz, 2H) 2.67 ppm (t, J=9 Hz, 2H)

Method B: From a Key Intermediate and an Aniline

Dissolved the Key Intermediate (1 eq) in DCM and added an equal volume of an aqueous solution of sodium carbonate (1.3 eq). Initiated vigorous stirring then added a DCM solution of triphosgene (0.3 eq) and continued stirring at r.t. for 2 hr. Dissolved the aniline (1.1 eq) in DCM and added to the reaction mixture; slowed the stirring so that there was distinction between the organic and aqueous layer and stirred at r.t. for another 2 hr or overnight if needed. Collected the organic layer and dried over sodium sulfate. Removed the drying agent by filtration and concentrated the filtrate to dryness. Dissolved the residue in DCM and added an equal volume of TFA. Stirred at r.t. until deprotection was complete. Concentrated to dryness then reconcentrated from DCM/MeOH. Reconcentrated from DCM several times then triturated the residue in an appropriate solvent to obtain the desired product as a TFA salt. If trituration did not produce a solid, then the residue was purified by silica gel chromatography using a mixture of DCM/MeOH/NH$_3$ to elute the product, providing the desired material as a free base.

The following compounds were prepared from Key Intermediate A and the appropriate aniline:

Compound 56: 1-(3-(2-amino-1H-imidazol-5-yl)phenyl)-3-(5-chloropyridin-2-yl)urea: $^1$H NMR (d$_6$-DMSO): 12.73 ppm (br s, 1H), 12.12 ppm (br s, 1H), 9.92 ppm (s, 1H), 9.55 ppm (s, 1H), 8.25 ppm (d, J=3 Hz, 1H), 7.80 ppm (dd, J=3, 9 Hz, 1H), 7.63 ppm (t, J=9 Hz, 2H), 7.47 ppm (br s, 2H), 7.40-7.13 ppm (m, 4H)

Compound 18: 1-(3-(2-amino-1H-imidazol-5-yl)phenyl)-3-(4-ethoxy-3-(trifluoromethyl)phenyl)urea: $^1$H NMR (d$_6$-DMSO): 12.69 ppm (br s, 1H), 12.11 ppm (br s, 1H), 9.07 ppm (s, 1H), 8.97 ppm (s, 1H), 7.82 ppm (d, J=3 Hz, 1H), 7.74 ppm (s, 1H), 7.51-7.40 ppm (m, 3H), 7.36-7.07 ppm (m, 5H), 4.04 ppm (q, J=6 Hz, 2H), (t, J=6 Hz, 3H)

Compound 19: 1-(3-(2-amino-1H-imidazol-5-yl)phenyl)-3-(3-bromo-4-propylphenyl)urea: $^1$H NMR (d$_6$-DMSO): 12.64 ppm (br s, 1H), 12.09 ppm (br s, 1H), 9.02 ppm (s, 1H), 8.95 ppm (s, 1H), 7.84 ppm (s, 1H), 7.75 ppm (s, 1H), 7.43 ppm (s, 2H), 7.34-7.10 ppm (m, 6H), 2.52 ppm (t, J=6 Hz, 2H), 1.48 ppm (m, 2H), 0.84 ppm (t, J=6 Hz, 3H)

Compound 20: 1-(3-(2-amino-1H-imidazol-5-yl)phenyl)-3-(3-chloro-4-ethoxyphenyl)urea: $^1$H NMR (d$_6$-DMSO): 12.64 ppm (br s, 1H), 12.09 ppm (br s, 1H), 8.89 ppm (d, J=3 Hz, 2H), 7.73 ppm (d, J=3 Hz, 1H), 7.64 ppm (d, J=3 Hz, 1H), 7.42 ppm (br s, 2H), 7.32-7.12 ppm (m, 5H), 7.04-6.95 ppm (m, 1H), 4.05-3.91 ppm (q, J=6 Hz, 2H), 1.26 ppm (t, J=6 Hz, 3H)

Compound 21: 1-(3-(2-amino-1H-imidazol-5-yl)phenyl)-3-(3-chloro-4-propoxyphenyl)urea: $^1$H NMR (d$_6$-DMSO): 12.62 ppm (br s, 1H), 12.08 ppm (br s, 1H), 8.87 ppm (br s, 1H), 7.74 ppm (d, J=3 Hz, 1H), 7.63 ppm (d, J=3 Hz, 1H), 7.41 ppm (br s, 2H), 7.34-7.11 ppm (m, 6H), 7.00 ppm (d, J=9 Hz, 1H), 3.88 ppm (t, J=9 Hz, 2H), 1.66 ppm (m, 2H), 0.92 ppm (t, J=9 ppm, 3H)

Compound 14: 1-(3-(2-amino-1H-imidazol-5-yl)phenyl)-3-(4-bromo-3-chlorophenyl)urea: $^1$H NMR (d$_6$-DMSO): 12.61 ppm (s, 1H), 12.06 ppm (s, 1H), 9.26 ppm (s, 1H), 9.05 ppm (s, 1H), 7.87 ppm (s, 1H), 7.75 ppm (s, 1H), 7.57 ppm (d, J=9 Hz, 1H), 7.41 ppm (s, 2H), 7.33-7.10 ppm (m, 5H)

Compound 8: 1-(3-(2-amino-1H-imidazol-5-yl)phenyl)-3-(3-chloro-4-(trifluoromethyl)phenyl)urea: $^1$H NMR (d$_6$-DMSO): 12.65 ppm (s, 1H), 12.09 ppm (s, 1H), 9.64 ppm (s, 1H), 9.24 ppm (s, 1H), 7.91 ppm (s, 1H), 7.76 ppm (s, 1H), 7.68 ppm (d, J=12 Hz, 1H), 7.43 ppm (s, 2H), 7.37-7.16 ppm (m, 5H)

Compound 17: 1-(3-(2-amino-1H-imidazol-5-yl)phenyl)-3-(4-ethoxyphenyl)urea: $^1$H NMR (d$_6$-DMSO): 12.63 ppm (br s, 1H), 12.06 ppm (br s, 1H), 8.74 ppm (s, 1H), 8.63 ppm (s, 1H), 7.70 ppm (s, 1H), 7.42 ppm (s, 2H), 7.32-7.08 ppm (m, 6H), 6.78 ppm (d, J=6 Hz, 2H), 3.89 ppm (q, J=6 Hz, 2H), 1.20 ppm (t, J=6 Hz, 3H)

Compound 16: 1-(3-(2-amino-1H-imidazol-5-yl)phenyl)-3-(3,4,5-trichlorophenyl)urea: $^1$H NMR (d$_6$-DMSO): 12.63 ppm (br s, 1H), 12.08 ppm (br s, 1H), 9.50 ppm (d, J=9 Hz, 1H), 9.28 ppm (d, J=9 Hz, 1H), 7.75 ppm (s, 1H), 7.71 ppm (d, J=3 Hz, 2H), 7.42 ppm (br s, 2H), 7.34-7.12 ppm (m, 4H)

Compound 10: 1-(3-(2-amino-1H-imidazol-5-yl)phenyl)-3-(3-fluoro-4-(trifluoromethyl)phenyl)urea: $^1$H NMR (d$_6$-DMSO): 12.75 ppm (s, 1H), 12.10 ppm (s, 1H), 9.72 ppm (s, 1H), 9.28 ppm (s, 1H), 7.80-7.65 ppm (m, 2H), 7.60-7.10 ppm (t, J=4 Hz, 1H), 7.45 ppm (s, 2H), 7.37-7.15 ppm (m, 5H)

Compound 11: 1-(3-(2-amino-1H-imidazol-5-yl)phenyl)-3-(3-bromo-4-(trifluoromethyl)phenyl)urea: $^1$H NMR (d$_6$-DMSO): 12.65 ppm (s, 1H), 12.05 ppm (s, 1H), 9.58 ppm (s, 1H), 9.18 ppm (s, 1H), 8.10 ppm (s, 1H), 7.78 ppm (s, 1H), ), 7.68 ppm (d, J=8 Hz, 1H), 7.50-7.35 ppm (m, 3H), 7.35-7.15 ppm (m, 4H)

Compound 9: 1-(3-(2-amino-1H-imidazol-5-yl)phenyl)-3-(3,4-bis(trifluoromethyl)phenyl)urea: $^1$H NMR (d$_6$-DMSO): 12.25 ppm (br s, 2H), 9.84 ppm (s, 1H), 9.28 ppm (s, 1H), 8.26 ppm (s, 1H), 7.88 ppm (d, J=4 Hz, 1H), 7.75 ppm (s, 2H), 7.40 ppm (s, 2H), 7.35-7.15 ppm (m, 4H)

Compound 12: 1-(3-(2-amino-1H-imidazol-5-yl)phenyl)-3-(2,6-difluoro-4-(trifluoromethyl)phenyl)urea: $^1$H NMR (d$_6$-DMSO): 12.65 ppm (br s, 1H), 12.05 ppm (s, 1H), 9.88 ppm (s, 1H), 9.38 ppm (s, 1H), 7.73 ppm (s, 1H), 7.55-7.15 ppm (m, 8H)

Compound 57: 1-(3-(2-amino-1H-imidazol-5-yl)phenyl)-3-(6-(trifluoromethyl)pyridin-3-yl)urea: $^1$H NMR (d$_6$-DMSO): 12.67 ppm (br s, 1H), 12.08 ppm (br s, 1H), 9.61 ppm (s, 1H), 9.23 ppm (s, 1H), 8.70 ppm (d, J=2.4 Hz, 1H), 8.12 ppm (dd, J=2.4, 9 Hz, 1H), 7.76 ppm (d, J=9 Hz, 2H), 7.43 ppm (br s, 2H), 7.36-7.14 ppm (m, 4H)

Compound 58: 1-(3-(2-amino-1H-imidazol-5-yl)phenyl)-3-(5,6-dichloropyridin-3-yl)urea: $^1$H NMR (d$_6$-DMSO): 12.41 ppm (br s, 1H), 10.33 ppm (s, 1H), 9.65 ppm (s, 1H), 8.32 ppm (d, J=2.4 Hz, 1H), 8.23 ppm (d, J=2.4 Hz, 2H), 7.64 ppm (s, 1H), 7.52-6.91 ppm (m, 5H)

Compound 84: 3-(3-(2-amino-1H-imidazol-5-yl)phenyl)-1-(3,4-dichlorophenyl)-1-methylurea: $^1$H NMR (d$_6$-DMSO): 12.65 ppm (br s, 1H), 12.13 ppm (br s, 1H), 8.45 ppm (s, 1H), 7.65 ppm (s, 1H), 7.59 ppm (t, J=3 Hz, 1H), 7.55 ppm (s, 1H), 7.44 ppm (s, 2H), 7.31-7.14 ppm (m, 5H), 3.22 ppm (s, 3H)

Compound 28: 1-(3-(2-amino-1H-imidazol-5-yl)phenyl)-3-(5,6,7,8-tetrahydronaphthalen-2-yl)urea: $^1$H NMR (d$_6$-DMSO): 12.32 ppm (br s, 2H), 8.75 ppm (s, 1H), 8.63 ppm (s, 1H), 7.73 ppm (s, 1H), 7.39 ppm (br s, 2H), 7.30-7.09 ppm (m, 4H), 7.05 ppm (dd, J=3, 6 Hz, 2H), 6.87 ppm (d, J=9 Hz, 1H), 2.59 ppm (m, 4H), 1.64 ppm (m, 4H)

Compound 85: 3-(3-(2-amino-1H-imidazol-5-yl)phenyl)-1-(3,4-dimethylphenyl)-1-phenylurea: $^1$H NMR (d$_6$-DMSO): 12.70 ppm (br s, 1H), 12.11 ppm (br s, 1H), 8.18 ppm (s, 1H), 7.66 (d, J=18 Hz, 2H), 7.47 (d, J=18 Hz, 2H), 7.40-7.05 ppm (m, 9H), 6.97 ppm (s, 1H), 6.91 (dd, J=3, 9 Hz, 1H), 2.15 ppm (s, 3H), 2.12 ppm (s, 3H)

Compound 26: 1-(3-(2-amino-1H-imidazol-5-yl)phenyl)-3-(3-chloro-4-morpholinophenyl)urea: $^1$H NMR (d$_6$-DMSO): 12.36 ppm (s, 2H), 8.93 ppm (s, 1H), 8.88 ppm (s, 1H), 7.73 ppm (s, 1H), 7.65 ppm (d, J=2.4 Hz, 1H), 7.39 ppm (s, 2H), 7.33-7.01 ppm (m, 6H), 3.65 ppm (m, 4H), 2.83 ppm (m, 4H)

Compound 27: 1-(3-(2-amino-1H-imidazol-5-yl)phenyl)-3-(3-chloro-4-hydroxyphenyl)urea: $^1$H NMR (d$_6$-DMSO): 12.65 ppm (br s, 1H), 12.09 ppm (br s, 1H), 9.71 ppm (s, 1H), 8.83 ppm (s, 1H), 8.74 ppm (s, 1H), 7.72 ppm (s, 1H), 7.55 ppm (d, J=3 Hz, 1H), 7.42 ppm (br s, 2H), 7.36-7.09 ppm (m, 4H), 7.00 ppm (dd, J=3, 9 Hz, 1H), 6.81 ppm (d, J=6 Hz, 1H)

Compound 22: 1-(3-(2-amino-1H-imidazol-5-yl)phenyl)-3-(3-bromo-4-methylphenyl)urea:
H NMR (d$_6$-DMSO): 12.64 ppm (br s, 1H), 12.08 ppm (br s, 1H), 9.01 ppm (s, 1H), 8.95 ppm (s, 1H), 7.85 ppm (s, 1H), 7.75 ppm (s, 1H), 7.42 ppm (br s, 2H), 7.32-7.10 ppm (m, 6H), 2.20 ppm (s, 3H)

Compound 5: 1-(3-(2-amino-1H-imidazol-5-yl)phenyl)-3-(4-propyl-3-(trifluoromethyl)phenyl)urea: $^1$H NMR (d$_6$-DMSO): 12.65 ppm (br s, 1H), 12.04 ppm (br s, 1H), 9.18 ppm (s, 1H), 8.98 ppm (s, 1H), 7.90 ppm (s, 1H), 7.75 ppm (s, 1H), 7.36-7.48 ppm (m, 3H), 7.14-7.33 ppm (m, 5H), 2.56 ppm (t, J=7 hz, 2H), 1.48 ppm (pent, J=7 Hz, 2H), 0.86 ppm (t, J=7 Hz, 3H)

Compound 6: 1-(4-allyl-3-(trifluoromethyl)phenyl)-3-(3-(2-amino-1H-imidazol-5-yl)phenyl)urea: $^1$H NMR (d$_6$-DMSO): 12.62 ppm (br s, 1H), 12.06 ppm (br s, 1H), 9.23 ppm (s, 1H), 8.99 ppm (s, 1H), 7.94 ppm (s, 1H), 7.74 ppm (s, 1H), 7.38-7.50 ppm (m, 3H), 7.14-7.30 ppm (m, 5H), 5.85 ppm (m, 1H), 4.97 ppm (m, 2H), 3.37 ppm (m, 2H)

Compound 92: 1,3-bis(3-(2-amino-1H-imidazol-5-yl)phenyl)urea: $^1$H NMR (d$_6$-DMSO): 12.76 ppm (s, 2H), 12.10 ppm (s, 2H), 9.58 ppm (s, 2H), 7.65 ppm (s, 2H), 7.40-7.12 ppm (m, 12H)

The following compounds were prepared from Key Intermediate B and the appropriate aniline:

Compound 66: 1-(3-(2-amino-4-methyl-1H-imidazol-5-yl)phenyl)-3-(4-propylphenyl)urea: $^1$H NMR (d$_6$-DMSO): 12.30 (br s, 1H), 12.14 ppm (br s, 1H), 8.91 ppm (s, 1H), 8.76 ppm (s, 1H), 7.65 ppm (s, 1H), 7.41-7.17 ppm (m, 6H), 7.06-6.92 ppm (m, 3H), 3.29 ppm (t, J=9 Hz, 2H), 2.18 ppm (s, 3H), 1.58-1.37 ppm (m, 2H), 0.80 ppm (t, J=9 Hz, 3H)

Compound 67: 1-(3-(2-amino-4-methyl-1H-imidazol-5-yl)phenyl)-3-(3,5-dibromophenyl)urea: $^1$H NMR (d$_6$-DMSO): 12.26 ppm (br s, 1H), 12.13 ppm (br s, 1H), 9.37 ppm (s, 1H), 9.30 ppm (s, 1H), 7.65 ppm (t, J=3 Hz, 3H), 7.44-7.22 ppm (m, 5H), 7.01 ppm (dd, J=3, 9 Hz, 1H), 2.18 ppm (s, 3H)

Compound 68: 1-(3-(2-amino-4-methyl-1H-imidazol-5-yl)phenyl)-3-(3-chloro-4-(trifluoromethyl)phenyl)urea: $^1$H NMR (d$_6$-DMSO): 12.28 ppm (br s, 1H), 12.15 ppm (br s, 1H), 9.77 ppm (s, 1H), 9.39 ppm (s, 1H), 7.87 ppm (d, J=1.8 Hz, 1H), 7.68 ppm (d, J=9 Hz, 2H), 7.46-7.24 ppm (m, 5H), 7.02 ppm (d, J=7.3 Hz, 1H), 2.18 ppm (s, 3H)

Compound 75: 1-(3-(2-amino-4-methyl-1H-imidazol-5-yl)phenyl)-3-(3,4-bis(trifluoromethyl)phenyl)urea: $^1$H NMR (d$_6$-DMSO): 12.31 ppm (br s, 1H), 12.15 ppm (br s, 1H), 9.90 ppm (s, 1H), 9.45 ppm (s, 1H), 8.19 ppm (s, 1H), 7.87 ppm (dd, J=3, 9 Hz, 2H), 7.66 ppm (s, 1H), 7.45-7.26 ppm (m, 4H), 7.03 ppm (dd, J=3 Hz, 6 Hz, 1H), 2.19 ppm (d, J=3 Hz, 3H)

Compound 94: 1,3-bis(3-(2-amino-4-methyl-1H-imidazol-5-yl)phenyl)urea: $^1$H NMR (d$_6$-DMSO): 12.36 ppm (br s, 2H), 12.20 ppm (br s, 2H), 9.66 ppm (s, 2H), 7.58 ppm (s, 2H), 7.40-7.17 ppm (m, 8H), 7.07-6.96 ppm (m, 2H), 2.18 ppm (s, 6H)

The following compound was prepared from Key Intermediate C and the appropriate aniline:

Compound 82: 1-(5-(2-amino-1H-imidazol-5-yl)-2-fluorophenyl)-3-(3-chloro-4-(trifluoromethyl)phenyl)urea: $^1$H NMR (d$_6$-DMSO): 12.22 ppm (br s, 1H), 10.59 ppm (s, 1H), 9.14 ppm (s, 1H), 8.22 ppm (d, J=6 Hz, 1H), 7.91 ppm (s, 1H), 7.68 ppm (d, J=9 Hz, 1H), 7.41 (d, J=9 Hz, 1H), 7.37-7.08 ppm (m, 6H)

The following compounds were prepared from Key Intermediate G and the appropriate aniline:

Compound 70: 1-(2-amino-4,5-dihydro-1H-naphtho[1,2-d]imidazol-8-yl)-3-(3-chloro-4-(trifluoromethyl)phenyl)urea: $^1$H NMR (d$_6$-DMSO): 12.44 ppm (br s, 2H), 9.50 ppm (s, 1H), 9.04 ppm (s, 1H), 7.92 ppm (s, 1H), 7.67 ppm (d, J=9 Hz, 1H), 7.60 ppm (s, 1H), 7.49 ppm (br s, 2H), 7.40 ppm (d, J=9 Hz, 1H), 7.09 ppm (d, J=9 Hz, 1H), 6.99 ppm (d, J=9 Hz, 1H), 2.86 ppm (t, J=6 Hz, 2H), 2.62 ppm (t, J=6 Hz, 2H)

Compound 71: 1-(2-amino-4,5-dihydro-1H-naphtho[1,2-d]imidazol-8-yl)-3-(3,5-dibromophenyl)urea: $^1$H NMR (d$_6$-DMSO): 12.66 ppm (s, 1H), 12.19 ppm (s, 1H), 9.26 ppm (s, 1H), 9.02 ppm (s, 1H), 7.66 ppm (t, J=3 Hz, 2H), 7.60 ppm (s, 1H), 5.51 ppm (br s, 2H), 7.35-7.27 ppm (m, 1H), 7.07 ppm (d, J=3, 9 Hz, 1H), 6.99-6.92 ppm (m, 1H), 2.85 ppm (t, J=9 Hz, 2H), 2.62 ppm (t, J=9 Hz, 2H)

The following compound was prepared from Key Intermediate F:

Compound 93: 1,3-bis(4-(2-amino-1H-imidazol-5-yl)phenyl)urea: $^1$H NMR (d$_6$-DMSO): 12.69 ppm (s, 2H), 11.95 ppm (s, 2H), 9.56 ppm (s, 2H), 7.47 ppm (dd, J=6, 18 Hz, 10H), 7.32 ppm (s, 2H), 7.19 ppm (s, 2H)

The following compound was prepared from Key Intermediate A and Key Intermediate F:

Compound 95: 1-(3-(2-amino-1H-imidazol-5-yl)phenyl)-3-(4-(2-amino-1H-imidazol-5-yl)phenyl)urea: $^1$H NMR (d$_6$-DMSO): 12.71 ppm (s, 2H), 12.01 ppm (d, J=30 Hz, 2H), 9.65 ppm (s, 1H), 9.43 ppm (s, 1H), 7.68-7.00 ppm (m, 14H)

The following compound was prepared from Key Intermediate A and Key Intermediate G:

Compound 96: 1-(3-(2-amino-1H-imidazol-5-yl)phenyl)-3-(2-amino-4,5-dihydro-1H-naphtho[1,2-d]imidazol-8-yl)urea: $^1$H NMR (d$_6$-DMSO): 12.76 ppm (s, 2H), 12.21 ppm (d, J=36 Hz, 2H), 8.92 ppm (d, J=24 Hz, 2H), 7.68-7.43 ppm (m, 6H), 7.37-7.02 ppm (m, 6H), 2.85 ppm (t, J=9 Hz, 2H), 2.62 ppm (t, J=9 Hz, 2H)

The following compound was prepared from Key Intermediate F and Key Intermediate G:

Compound 97: 1-(4-(2-amino-1H-imidazol-5-yl)phenyl)-3-(2-amino-4,5-dihydro-1H-naphtho[1,2-d]imidazol-8-yl)urea: $^1$H NMR (d$_6$-DMSO): 12.75 ppm (s, 2H), 12.25 ppm (s, 1H), 12.02 ppm (s, 1H), 9.06 ppm (s, 1H), 8.88 ppm (s, 1H), 7.59-7.41 ppm (m, 10H), 7.18 ppm (s, 1H), 7.06 ppm (s, 1H), 2.85 ppm (t, J=9 Hz, 2H), 2.62 ppm (t, J=9 Hz, 2H)

The following compound was prepared from Key Intermediate F and Key Intermediate H:

Compound 98: 1-(4-(2-amino-1H-imidazol-5-yl)phenyl)-3-(2-amino-1H-naphtho[1,2-d]63midazole-8-yl)urea: $^1$H NMR (d$_6$-DMSO): 13.58 ppm (br s, 1H), 12.80 ppm (br s, 1H), 12.78 ppm (br s, 1H), 12.02 ppm (br s, 1H), 9.32 ppm (s, 1H), 9.25 ppm (s, 1H), 8.39 ppm (s, 1H), 8.15 ppm (br s, 2H), 7.88 ppm (d, J=9 Hz, 1H), 7.63 ppm (d, J=9 Hz, 1H), 7.45-7.56 ppm (m, 5H), 7.36-7.40 ppm (m, 3H), 7.20 ppm (s, 1H)

Example 2: Testing of Compounds

The minimal inhibitory concentration (MIC) values of imipenem (I); meropenem (M) and doripenem (D) in the presence and absence of 2-aminoimidazole compounds are provided in Table 1. The concentration of each compound used in μM in the MIC assay is shown in parentheses.

TABLE 1

Minimal inhibitory concentration (MIC) values upon addition of compound

| Compound | Structure | A. baumannii ATCC BAA-1605 | | | A. baumannii AB5075 | | | K. pneumoniae ATCC BAA-2146 | | | K pneumoniae ATCC BAA-1705 | | |
|---|---|---|---|---|---|---|---|---|---|---|---|---|---|
| | | I | M | D | I | M | D | I | M | D | I | M | D |
| None | | 32 | 32 | 32 | 32 | 32 | 32 | 128 | 256 | 256 | 64 | 64 | 64 |

The following compounds are 2-amino-4-phenyl imidazole derivatives with a urea functionality on the 3-position of the phenyl ring. These compounds contain a phenyl substituent on the distal nitrogen of the urea. The activity of these compounds may be dependent upon the substitution pattern on the terminal phenyl ring, as demonstrated below.

| 1 | (structure) | 2 (60) 8 (15) 16 (10) | 2 (60) 6 (15) 16 (10) | 1 (60) 8 (15) 8 (10) | 4 (60) 4 (30) 8 (15) | 1 (60) 2 (30) 8 (15) | 0.5 (60) 2 (30) 8 (15) | 128 (60) | 128 (60) | 64 (60) | | | |
| 2 | (structure) | 1 (30) 4 (15) 32 (5) | 2 (30) 4 (15) 32 (5) | 1 (30) 4 (15) 32 (5) | 1 (60) 2 (30) 16 (15) | 0.5 (60) 2 (30) 6 (15) | 0.5 (60) 1 (30) 8 (15) | 128 (60) | 128 (60) | 128 (60) | 64 (60) | 16 (60) | 64 (60) |
| 3 | (structure) | 8 (15) 16 (10) | 4 (15) 16 (10) | 6 (15) 8 (10) | 4 (30) 8 (15) | 2 (30) 4 (15) | 1 (30) 6 (15) | 128 (15) | 256 (15) | 256 (15) | | | |
| 4 | (structure) | 4 (7) 32 (4) | 4 (7) 16 (4) | 16 (7) 32 (4) | 8 (7) 32 (4) | 8 (7) | 8 (7) | 128 (7) | 256 (7) | 256 (7) | | | |

TABLE 1-continued

Minimal inhibitory concentration (MIC) values upon addition of compound

| Compound | Structure | A. baumannii ATCC BAA-1605 | | | A. baumannii AB5075 | | | K. pneumoniae ATCC BAA-2146 | | | K pneumoniae ATCC BAA-1705 | | |
|---|---|---|---|---|---|---|---|---|---|---|---|---|---|
| | | I | M | D | I | M | D | I | M | D | I | M | D |
| None | | 32 | 32 | 32 | 32 | 32 | 32 | 128 | 256 | 256 | 64 | 64 | 64 |
| 5 | (2-aminoimidazole-phenyl-urea-phenyl-CF₃-propyl) | 16 (7) | 16 (7) | 16 (7) | 16 (7) | 16 (7) | 16 (7) | 64 (15) | 64 (15) | 32 (15) | 64 (15) | 32 (15) | 64 (15) |
| 6 | (2-aminoimidazole-phenyl-urea-phenyl-CF₃-allyl) | 32 (7) | 16 (7) | 16 (7) | 16 (7) | 16 (7) | 8 (7) | 256 (7) | 256 (7) | 256 (7) | 64 (7) | 64 (7) | 64 (7) |
| 7 | (2-aminoimidazole-phenyl-urea-3,5-dibromophenyl) | 2 (30)<br>8 (10) | 2 (30)<br>8 (10) | 4 (10) | 2 (30)<br>4 (15)<br>4 (10)<br>16 (5) | 1 (30)<br>2 (15)<br>4 (10)<br>16 (5) | 1 (30)<br>2 (15)<br>4 (10)<br>8 (5) | 32 (15) | 32 (15) | 32 (15) | 32 (15) | 16 (15) | 24 (15) |
| 8 | (2-aminoimidazole-phenyl-urea-phenyl-Cl-CF₃) | 3 (7)<br>8 (5) | 6 (7)<br>16 (5) | 4 (7)<br>16 (5) | 12 (7)<br>16 (5) | 8 (7)<br>12 (5) | 6 (7)<br>16 (5) | 64 (7)<br>128 (5) | 96 (7)<br>256 (5) | 128 (7)<br>256 (5) | 32 (7)<br>64 (5) | 24 (7)<br>64 (5) | 64 (7)<br>64 (5) |
| 9 | (2-aminoimidazole-phenyl-urea-phenyl-3,4-bis-CF₃) | 4 (7)<br>16 (5) | 4 (7)<br>16 (5) | 4 (7)<br>16 (5) | 4 (10)<br>32 (7) | 4 (10)<br>16 (7) | 4 (10)<br>16 (7) | 128 (10)<br>128 (7) | 128 (10)<br>128 (7) | 256 (10)<br>256 (7) | 64 (10) | 32 (10)<br>64 (7) | 32 (10) |

TABLE 1-continued
Minimal inhibitory concentration (MIC) values upon addition of compound
| | | MIC (μg/mL) (μM of 2-AI Compound Used) | | | | | | | | | | | |
|---|---|---|---|---|---|---|---|---|---|---|---|---|---|
| | | *A. baumannii* ATCC BAA-1605 | | | *A. baumannii* AB5075 | | | *K. pneumoniae* ATCC BAA-2146 | | | *K. pneumoniae* ATCC BAA-1705 | | |
| Compound None | Structure | I 32 | M 32 | D 32 | I 32 | M 32 | D 32 | I 128 | M 256 | D 256 | I 64 | M 64 | D 64 |
| 10 | 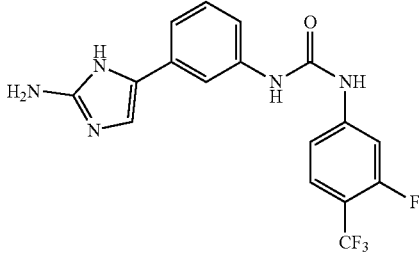 [SMILES: Nc1ncc(-c2cccc(NC(=O)Nc3ccc(C(F)(F)F)c(F)c3)c2)[nH]1] | 16 (7) | 8 (7) | 8 (7) | 16 (10) 16 (7) | 8 (10) 16 (7) | 8 (10) 16 (7) | 128 (10) 128 (7) | 256 (10) 256 (7) | 256 (10) 256 (7) | 64 (10) | 64 (10) 64 (7) | 64 (10) |
| 11 | 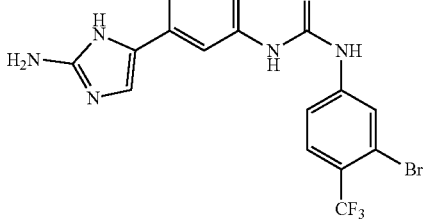 | 16 (4) | 16 (4) | 8 (4) | 8 (7) | 4 (7) | 8 (7) | 32 (7) | 64 (7) | 128 (7) | 32 (7) | 16 (7) | 16 (7) |
| 12 | 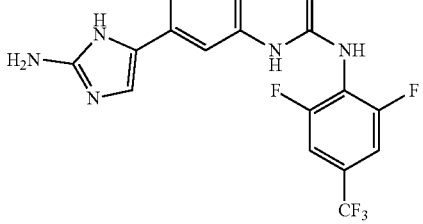 | 8 (7) | 8 (7) | 8 (7) | 4 (10) 32 (5) | 4 (10) 32 (5) | 4 (10) 32 (5) | 128 (10) | 256 (10) | 256 (10) | 64 (10) | 64 (10) 64 (7) | 64 (10) |
| 13 | 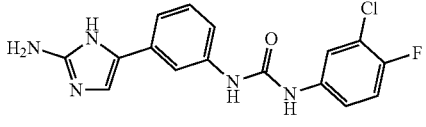 [SMILES: Nc1ncc(-c2cccc(NC(=O)Nc3ccc(F)c(Cl)c3)c2)[nH]1] | 4 (30) 12 (15) | 8 (30) 8 (15) | 8 (30) 8 (15) | 4 (60) 8 (30) 16 (15) | 3 (60) 8 (30) | 2 (60) 8 (15) | 128 (30) | 256 (30) | 256 (30) | | 64 (30) | |
| 14 | 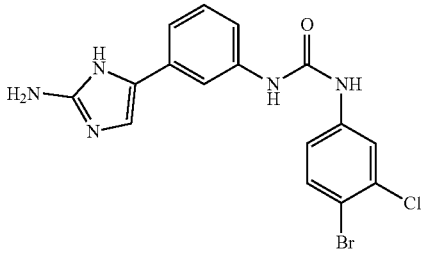 [SMILES: Nc1ncc(-c2cccc(NC(=O)Nc3ccc(Br)c(Cl)c3)c2)[nH]1] | 4 (15) | 8 (15) | 12 (15) | 16 (15) | 8 (15) | 6 (15) | | | | 64 (7) | 32 (7) | 64 (7) |

TABLE 1-continued

Minimal inhibitory concentration (MIC) values upon addition of compound

| Compound | Structure | A. baumannii ATCC BAA-1605 | | | A. baumannii AB5075 | | | K. pneumoniae ATCC BAA-2146 | | | K pneumoniae ATCC BAA-1705 | | |
|---|---|---|---|---|---|---|---|---|---|---|---|---|---|
| | | I | M | D | I | M | D | I | M | D | I | M | D |
| None | Structure | 32 | 32 | 32 | 32 | 32 | 32 | 128 | 256 | 256 | 64 | 64 | 64 |
| 15 | [structure: 2-aminoimidazole-phenyl-urea-NH-(3,5-dichloro-4-bromophenyl)] | 16 (30) 16 (15) | 8 (60) 8 (30) 32 (15) | 16 (30) 16 (15) | 4 (60) 4 (30) 16 (15) | 2 (60) 4 (30) 16 (15) | 2 (60) 2 (30) 16 (15) | 8 (60) 128 (30) | 16 (60) 256 (30) | 32 (60) 256 (30) | 32 (60) | 16 (60) | 16 (60) |
| 16 | [structure: 2-aminoimidazole-phenyl-urea-NH-(3,4,5-trichlorophenyl)] | 32 (60) 16 (30) | 16 (60) | 12 (60) | 16 (60) 16 (30) | 16 (60) | 16 (60) | 128 (60) | 128 (60) | 128 (60) | 64 (60) | 64 (60) | 64 (60) |
| 17 | [structure: 2-aminoimidazole-phenyl-urea-NH-(4-ethoxyphenyl)] | 8 (60) 16 (30) | 8 (60) 16 (30) | 4 (60) 16 (30) | 16 (60) 32 (30) | 8 (60) 32 (30) | 8 (60) 32 (30) | | | | 64 (60) | 64 (60) | 64 (60) |
| 18 | [structure: 2-aminoimidazole-phenyl-urea-NH-(4-ethoxy-3-trifluoromethylphenyl)] | 8 (30) 16 (15) | 8 (30) 16 (15) | 6 (30) 16 (15) | 8 (30) 16 (15) | 8 (30) 12 (15) | 8 (30) 16 (15) | 128 (25) | 256 (25) | 256 (25) | 24 (60) | 24 (60) | 24 (60) |

TABLE 1-continued

Minimal inhibitory concentration (MIC) values upon addition of compound

| | | MIC (μg/mL) (μM of 2-AI Compound Used) | | | | | | | | | | | |
|---|---|---|---|---|---|---|---|---|---|---|---|---|
| | | *A. baumannii* ATCC BAA-1605 | | | *A. baumannii* AB5075 | | | *K. pneumoniae* ATCC BAA-2146 | | | *K pneumoniae* ATCC BAA-1705 | | |
| Compound None | Structure | I 32 | M 32 | D 32 | I 32 | M 32 | D 32 | I 128 | M 256 | D 256 | I 64 | M 64 | D 64 |
| 19 | | 4 (30) | 8 (30) | 6 (30) | 8 (60) 12 (30) | 6 (60) 16 (30) | 8 (60) 16 (30) | 64 (60) | 64 (60) | 64 (60) | 64 (30) | 64 (30) | 64 (30) |
| 20 | | 6 (60) | 4 (60) | 3 (60) | 8 (60) | 4 (60) | 6 (60) | 128 (60) | 64 (60) | 64 (60) | 64 (60) | 32 (60) | 64 (60) |
| 21 | | 6 (30) | 8 (30) | 4 (30) | 3 (60) 12 (30) | 1 (60) 8 (30) | 2 (60) 8 (30) | | | | 64 (30) | 64 (30) | 64 (30) |
| 22 | | | 4 (60) | | | 2 (60) | | | 64 (60) | | | 16 (60) | |

TABLE 1-continued

Minimal inhibitory concentration (MIC) values upon addition of compound

| Compound None | Structure | \multicolumn{3}{c}{A. baumannii ATCC BAA-1605} | | | \multicolumn{3}{c}{A. baumannii AB5075} | | | \multicolumn{3}{c}{K. pneumoniae ATCC BAA-2146} | | | \multicolumn{3}{c}{K pneumoniae ATCC BAA-1705} | | |
|---|---|---|---|---|---|---|---|---|---|---|---|---|---|---|---|---|
| | | I 32 | M 32 | D 32 | I 32 | M 32 | D 32 | I 128 | M 256 | D 256 | I 64 | M 64 | D 64 |
| 23 | (structure) | 16 (15) | 8 (15) | 8 (15) | 16 (15) | 8 (15) | 8 (15) | 128 (30) | 256 (30) | 256 (30) | 64 (30) | 32 (30) | 64 (30) |
| 24 | (structure) | 8 (15) | 8 (15) | 8 (15) | 4 (30) | 4 (30) | 4 (30) | 128 (60) | 256 (60) | 256 (60) | 64 (30) | 64 (30) | 64 (30) |
| 25 | (structure) | 4 (30) | 4 (30) | 8 (30) | 2 (60) / 4 (30) / 8 (15) | 2 (60) / 4 (30) / 16 (15) | 2 (60) / 4 (30) / 16 (15) | 32 (60) / 128 (30) | 32 (60) / 128 (30) | 32 (60) / 128 (30) | 32 (60) | 24 (60) | 24 (60) |
| 26 | (structure) | 16 (15) | 8 (15) | 8 (15) | 16 (15) | 8 (15) | 8 (15) | 128 (30) | 256 (30) | 256 (30) | 64 (30) | 64 (30) | 64 (30) |
| 27 | (structure) | 16 (60) | 16 (60) | 16 (60) | 8 (60) | 8 (60) | 8 (60) | 128 (60) | 256 (60) | 256 (60) | 64 (60) | 64 (60) | 64 (60) |

TABLE 1-continued

Minimal inhibitory concentration (MIC) values upon addition of compound

| Compound None | Structure | \multicolumn{3}{c}{A. baumannii ATCC BAA-1605} | \multicolumn{3}{c}{A. baumannii AB5075} | \multicolumn{3}{c}{K. pneumoniae ATCC BAA-2146} | \multicolumn{3}{c}{K pneumoniae ATCC BAA-1705} |
|---|---|---|---|---|---|---|---|---|---|---|---|---|---|
| | | I 32 | M 32 | D 32 | I 32 | M 32 | D 32 | I 128 | M 256 | D 256 | I 64 | M 64 | D 64 |
| 28 | (structure) | 16 (7) | 16 (7) | 16 (7) | 8 (15) 32 (7) | 4 (15) 16 (7) | 4 (15) 8 (7) | 128 (30) | 64 (30) | 128 (30) | 64 (7) | 64 (7) | 64 (7) |
| 29 | (structure) | 16 (15) | 8 (15) | 8 (15) | 4 (30) 16 (15) | 2 (30) 8 (15) | 4 (30) 8 (15) | 128 (30) | 256 (30) | 256 (30) | 64 (30) | 64 (30) | 64 (30) |
| 30 | (structure) | 16 (30) | 16 (30) | 16 (30) | 16 (30) | 8 (30) | 4 (30) | 128 (60) | 128 (60) | 256 (60) | | | |
| 31 | (structure) | 32 (30) | 32 (30) | 32 (30) | 8 (60) | 16 (60) | 8 (60) | 128 (60) | 256 (60) | 256 (60) | 64 (60) | 64 (60) | 64 (60) |
| 32 | (structure) | 16 (4) | 32 (4) | 32 (4) | 32 (4) | 32 (4) | 16 (4) | 64 (7) | 128 (7) | 256 (7) | 64 (7) | 32 (7) | 64 (7) |
| 33 | (structure) | 4 (60) 4 (30) 8 (10) | 4 (60) 4 (30) 8 (10) | 2 (60) 4 (30) 8 (10) | 4 (60) 4 (30) 4 (15) 8 (10) | 4 (60) 4 (30) 4 (15) 8 (10) | 2 (60) 4 (30) 4 (15) 8 (10) | 128 (15) 128 (7) | 128 (15) 256 (7) | 128 (15) 256 (7) | | | |

TABLE 1-continued

Minimal inhibitory concentration (MIC) values upon addition of compound

| Compound None | Structure | MIC (µg/mL) (µM of 2-AI Compound Used) | | | | | | | | | | | |
|---|---|---|---|---|---|---|---|---|---|---|---|---|---|
| | | *A. baumannii* ATCC BAA-1605 | | | *A. baumannii* AB5075 | | | *K. pneumoniae* ATCC BAA-2146 | | | *K pneumoniae* ATCC BAA-1705 | | |
| | | I 32 | M 32 | D 32 | I 32 | M 32 | D 32 | I 128 | M 256 | D 256 | I 64 | M 64 | D 64 |
| 34 | [2-amino-imidazole-phenyl-urea-3,4-dibromophenyl] | 4 (15) 4 (10) | 4 (15) 4 (10) | 2 (15) 8 (10) | 4 (15) 4 (10) 16 (7) | 4 (15) 4 (10) 16 (7) | 2 (15) 4 (10) 8 (7) | 128 (15) | 256 (15) | 256 (15) | | | |
| 35 | [2-amino-imidazole-phenyl-urea-3-chloro-4-methylphenyl] | 4 (60) 4 (30) 8 (15) | 4 (60) 4 (30) 16 (15) | 4 (60) 4 (30) 16 (15) | 2 (60) 8 (30) 16 (15) | 2 (60) 4 (30) 12 (15) | 1 (60) 4 (30) 12 (15) | 128 (60) | 256 (60) | 256 (60) | | | |
| 36 | [2-amino-imidazole-phenyl-urea-4-methyl-3-trifluoromethylphenyl] | 3 (15) 4 (10) 16 (5) | 2 (15) 4 (10) 16 (5) | 2 (15) 8 (10) 16 (5) | 4 (15) 16 (10) | 4 (15) 12 (10) | 2 (15) 6 (10) | 128 (15) | 256 (15) | 256 (15) | | | |
| 37 | [2-amino-imidazole-phenyl-urea-5-bromo-2-fluorophenyl] | 4 (60) 8 (30) | 2 (60) | 4 (60) | 4 (60) | 4 (60) | 2 (60) | 128 (30) | 256 (30) | 256 (30) | 64 (30) | | |
| 38 | [2-amino-imidazole-phenyl-urea-4-methylphenyl] | | | | 8 (60) | 8 (60) | 8 (60) | 128 (60) | 256 (60) | 256 (60) | | | |

TABLE 1-continued

Minimal inhibitory concentration (MIC) values upon addition of compound

| Compound None | Structure | A. baumannii ATCC BAA-1605 (µM of 2-AI Compound Used) | | | A. baumannii AB5075 | | | K. pneumoniae ATCC BAA-2146 | | | K pneumoniae ATCC BAA-1705 | | |
|---|---|---|---|---|---|---|---|---|---|---|---|---|---|
| | | I 32 | M 32 | D 32 | I 32 | M 32 | D 32 | I 128 | M 256 | D 256 | I 64 | M 64 | D 64 |
| 39 | 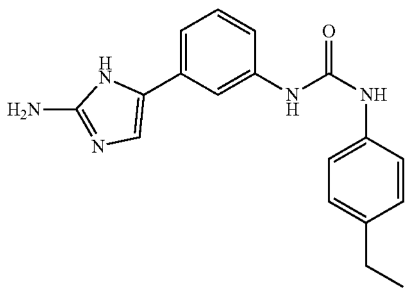 [SMILES: CCc1ccc(NC(=O)Nc2cccc(-c3cnc(N)[nH]3)c2)cc1] | 16 (30) | | | 8 (60) | 8 (60) | 4 (60) | 128 (60) | 256 (60) | 256 (60) | | | |
| 40 | 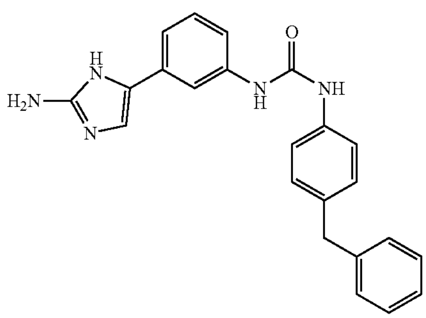 [SMILES: Nc1ncc(-c2cccc(NC(=O)Nc3ccc(Cc4ccccc4)cc3)c2)[nH]1] | 16 (15) | 12 (15) | 16 (15) | 4 (60) 8 (30) | 2 (60) 4 (30) | 2 (60) 4 (30) | 128 (60) | 256 (60) | 256 (60) | | | |
| 41 | 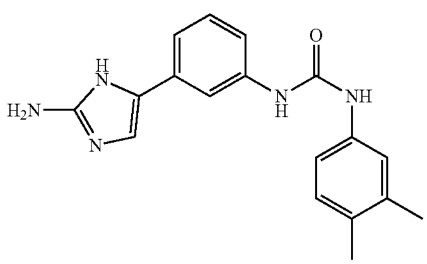 [SMILES: Cc1ccc(NC(=O)Nc2cccc(-c3cnc(N)[nH]3)c2)cc1C] | 2 (60) 8 (30) | 1 (60) 8 (30) | 1 (60) 4 (30) | 2 (60) 8 (30) 32 (15) | 2 (60) 8 (30) 32 (15 | 1 (60) 8 (30) 16 (15) | 128 (30) | 256 (30) | 256 (30) | | | |
| 42 | 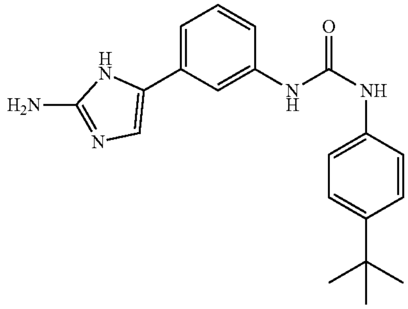 [SMILES: CC(C)(C)c1ccc(NC(=O)Nc2cccc(-c3cnc(N)[nH]3)c2)cc1] | 8 (15) | | | 16 (15) | 16 (15) | 8 (15) | 128 (30) | 256 (30) | 256 (30) | | | |

TABLE 1-continued

Minimal inhibitory concentration (MIC) values upon addition of compound

| Compound None | Structure | A. baumannii ATCC BAA-1605 (μM of 2-AI Compound Used) | | | A. baumannii AB5075 | | | K. pneumoniae ATCC BAA-2146 | | | K pneumoniae ATCC BAA-1705 | | |
|---|---|---|---|---|---|---|---|---|---|---|---|---|---|
| | | I 32 | M 32 | D 32 | I 32 | M 32 | D 32 | I 128 | M 256 | D 256 | I 64 | M 64 | D 64 |
| 43 | [structure] | | | | 8 (60) | 16 (60) 16 (30) | 8 (60) | 128 (60) | 256 (60) | 256 (60) | | | |
| 44 | [structure] | | | | 32 (60) | 32 (60) | 32 (60) | 128 (60) | 256 (60) | 256 (60) | | | |
| 45 | [structure] | 16 (30) | 8 (30) | 8 (30) | 4 (60) 8 (30) | 4 (60) 8 (30) | 2 (60) 8 (30) | 128 (60) | 256 (60) | 256 (60) | | | |
| 46 | [structure] | | 16 (15) | | 8 (15) | 16 (15) | 8 (15) | 128 (15) | 256 (15) | 256 (15) | | | |
| 47 | [structure] | 4 (60) 12 (15) | 4 (60) 8 (15) | 4 (60) 16 (15) | 2 (60) 8 (30) 16 (15) | 2 (60) 8 (30) 16 (15) | 2 (60) 4 (30) 16 (15) | 128 (60) | 128 (60) | 128 (60) | 64 (60) | 64 (60) | 64 (60) |

TABLE 1-continued

Minimal inhibitory concentration (MIC) values upon addition of compound

| Compound None | Structure | A. baumannii ATCC BAA-1605 MIC (µg/mL) (µM of 2-AI Compound Used) | | | A. baumannii AB5075 | | | K. pneumoniae ATCC BAA-2146 | | | K pneumoniae ATCC BAA-1705 | | |
|---|---|---|---|---|---|---|---|---|---|---|---|---|---|
| | | I 32 | M 32 | D 32 | I 32 | M 32 | D 32 | I 128 | M 256 | D 256 | I 64 | M 64 | D 64 |
| 48 | 2-amino-1H-imidazol-5-yl-phenyl urea with 4-chloro-3-methylphenyl | 4 (60) | 4 (60) | 2 (60) | 4 (60) 4 (30) 16 (15) | 4 (60) 4 (30) 32 (15) | 2 (60) 4 (30) 16 (15) | 128 (60) | 128 (60) | 64 (60) | 64 (60) | 64 (60) | 64 (60) |
| 49 | 2-amino-1H-imidazol-5-yl-phenyl urea with 4-(methoxycarbonyl)phenyl | 32 (60) | 32 (60) | 32 (60) | | | | 128 (60) | 256 (60) | 256 (60) | 64 (60) | 64 (60) | 64 (60) |
| 50 | 2-amino-1H-imidazol-5-yl-phenyl urea with 3-cyanophenyl | 16 (60) | 16 (60) | 32 (60) | 32 (60) | 32 (60) | 32 (60) | 128 (60) | 256 (60) | 256 (60) | 64 (60) | 64 (60) | 64 (60) |
| 51 | 2-amino-1H-imidazol-5-yl-phenyl urea with 4-cyanophenyl | 32 (60) | 16 (60) | 32 (60) | 32 (60) | 32 (60) | 32 (60) | 128 (60) | 256 (60) | 256 (60) | 64 (60) | 64 (60) | 64 (60) |
| 52 | 2-amino-1H-imidazol-5-yl-phenyl urea with 3,4-dimethoxyphenyl | | | | 32 (60) | 32 (60) | 32 (60) | 128 (60) | 256 (60) | 256 (60) | | | |

TABLE 1-continued

Minimal inhibitory concentration (MIC) values upon addition of compound

| | | MIC (μg/mL) (μM of 2-AI Compound Used) | | | | | | | | | | |
|---|---|---|---|---|---|---|---|---|---|---|---|---|
| | | *A. baumannii* ATCC BAA-1605 | | | *A. baumannii* AB5075 | | | *K. pneumoniae* ATCC BAA-2146 | | | *K pneumoniae* ATCC BAA-1705 | | |
| Compound | Structure | I | M | D | I | M | D | I | M | D | I | M | D |
| None | | 32 | 32 | 32 | 32 | 32 | 32 | 128 | 256 | 256 | 64 | 64 | 64 |
| 53 | | | | | 32 (60) | 32 (60) | 32 (60) | 128 (60) | 256 (60) | 256 (60) | | | |
| 54 | | | | | 16 (60) | 32 (60) | 32 (60) | 128 (60) | 256 (60) | 256 (60) | | | |

The following compounds are 2-amino-4-phenyl imidazole derivatives with a urea functionality on the 3-position of the phenyl ring. These compounds contain a heterocycle on the distal nitrogen of the urea. In some embodiments, this type of substitution may be detrimental to activity.

| Compound | Structure | I | M | D | I | M | D | I | M | D | I | M | D |
|---|---|---|---|---|---|---|---|---|---|---|---|---|---|
| 55 | 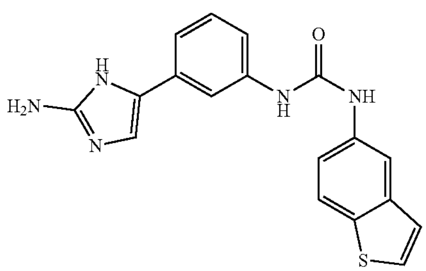 [SMILES: Nc1ncc(-c2cccc(NC(=O)Nc3ccc4sccc4c3)c2)[nH]1] | 2 (60) 8 (30) | 2 (60) 4 (30) | 2 (60) 4 (30) | 4 (60) 8 (30) | 2 (60) 8 (30) | 2 (60) 4 (30) | 128 (60) | 256 (60) | 256 (60) | 64 (60) | 64 (60) | 32 (60) |
| 56 | 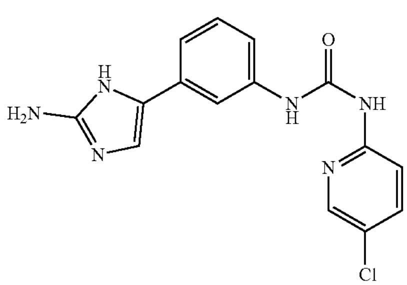 [SMILES: Nc1ncc(-c2cccc(NC(=O)Nc3ccc(Cl)cn3)c2)[nH]1] | 8 (60) 8 (30) | 8 (60) 8 (30) | 8 (30) | 8 (30) | 6 (30) | 4 (30) | 128 (60) | 256 (60) | 128 (60) | | | |

TABLE 1-continued

Minimal inhibitory concentration (MIC) values upon addition of compound

| | | A. baumannii ATCC BAA-1605 | | | A. baumannii AB5075 | | | K. pneumoniae ATCC BAA-2146 | | | K pneumoniae ATCC BAA-1705 | | |
|---|---|---|---|---|---|---|---|---|---|---|---|---|---|
| Compound None | Structure | I 32 | M 32 | D 32 | I 32 | M 32 | D 32 | I 128 | M 256 | D 256 | I 64 | M 64 | D 64 |
| 57 | 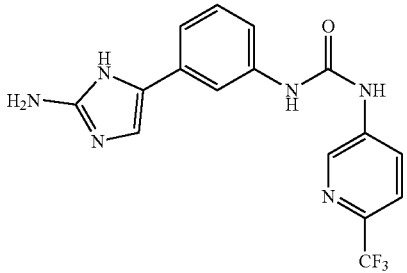 [SMILES: Nc1ncc(-c2cccc(NC(=O)Nc3ccc(C(F)(F)F)nc3)c2)[nH]1] | 4 (60) 8 (30) | 4 (60) 8 (30) | 2 (60) 8 (30) | 4 (60) 16 (30) | 2 (60) 16 (30) | 2 (60) 16 (30) | 128 (30) | 256 (30) | 256 (30) | 64 (60) | | |
| 58 | 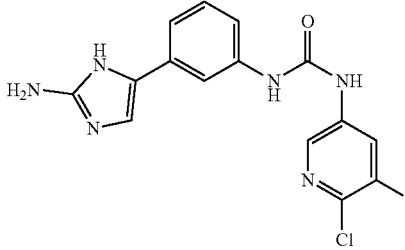 | 4 (60) 8 (30) | 4 (60) 8 (30) | 4 (60) 16 (30) | 8 (60) 8 (30) | 4 (60) 8 (30) | 4 (60) 16 (30) | 128 (60) | 256 (60) | 256 (60) | 64 (60) | 64 (60) | 64 (60) |
| 59 | 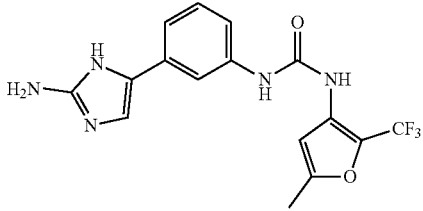 [SMILES: Cc1cc(NC(=O)Nc2cccc(-c3cnc(N)[nH]3)c2)c(C(F)(F)F)o1] | 8 (60) | 8 (60) | 8 (60) | 16 (60) | 8 (60) | 8 (60) | 128 (60) | 256 (60) | 256 (60) | 64 (60) | 64 (60) | 64 (60) |
| 60 | 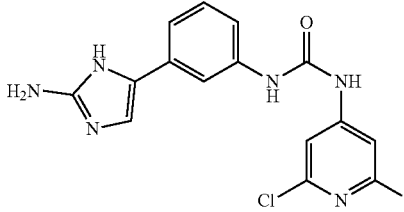 | 16 (60) | 8 (60) | 16 (60) | 16 (60) | 16 (60) | 16 (60) | 128 (60) | 256 (60) | 256 (60) | 64 (60) | 64 (60) | 64 (60) |

The following compounds are 2-amino-4-phenyl-5-substituted imidazole derivatives with a urea functionality on the 3-position of the 4-phenyl ring. In some embodiments, the C-5 substituent may be methyl, phenyl or an ethyl bridged to the C-4 phenyl ring. In some embodiments, this ethyl bridge may be attached to the 6-position of the C-4 phenyl ring, and the compounds are typically active. In some embodiments, when the ethyl bridge is attached to the 2-position of the 4-phenyl ring, the compounds may not be as active.

| 61 | 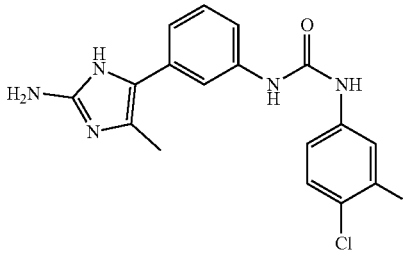 | 8 (7) | 8 (7) | 4 (7) | 8 (7) | 16 (7) | 8 (7) | 128 (7) | 128 (7) | 128 (7) | 32 (7) | 64 (7) | 64 (7) |

TABLE 1-continued

Minimal inhibitory concentration (MIC) values upon addition of compound

| Compound None | Structure | MIC (µg/mL) (µM of 2-AI Compound Used) | | | | | | | | | | | |
|---|---|---|---|---|---|---|---|---|---|---|---|---|---|
| | | *A. baumannii* ATCC BAA-1605 | | | *A. baumannii* AB5075 | | | *K. pneumoniae* ATCC BAA-2146 | | | *K pneumoniae* ATCC BAA-1705 | | |
| | | I 32 | M 32 | D 32 | I 32 | M 32 | D 32 | I 128 | M 256 | D 256 | I 64 | M 64 | D 64 |
| 62 | 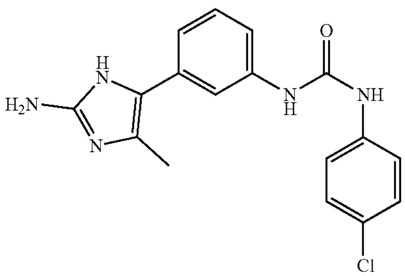 [SMILES: Cc1nc(N)[nH]c1-c1cccc(NC(=O)Nc2ccc(Cl)cc2)c1] | 8 (30) 16 (15) | 4 (30) 32 (15) | 4 (30) 32 (15) | 8 (30) 16 (15) | 4 (30) 8 (15) | 4 (30) 8 (15) | 128 (60) | 256 (60) | 256 (60) | | | |
| 63 | 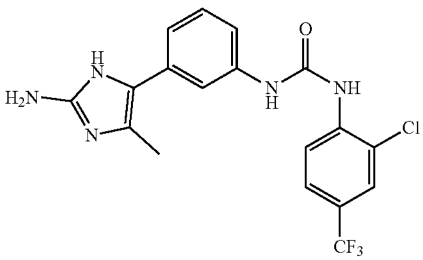 [SMILES: Cc1nc(N)[nH]c1-c1cccc(NC(=O)Nc2ccc(C(F)(F)F)cc2Cl)c1] | 4 (30) 16 (15) | 4 (30) 32 (15) | 16 (15) | 8 (30) 16 (15) | 16 (30) 16 (15) | 8 (15) | 128 (30) | 128 (30) | 128 (30) | | | |
| 64 | 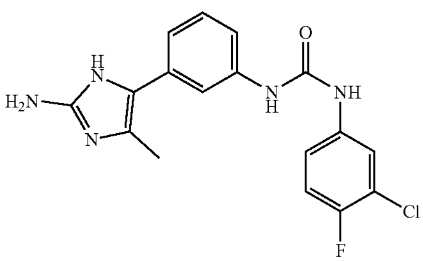 [SMILES: Cc1nc(N)[nH]c1-c1cccc(NC(=O)Nc2ccc(F)c(Cl)c2)c1] | 8 (15) | 8 (15) | 8 (15) | 8 (15) | 8 (15) | 8 (15) | 128 (30) | 256 (30) | 256 (30) | 64 (30) | 64 (30) | 64 (30) |
| 65 | 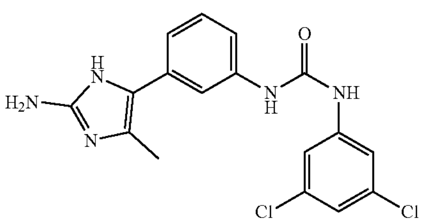 | 8 (30) | 8 (30) | 8 (30) | 16 (30) | 8 (30) | 8 (30) | 128 (30) | 64 (30) | 64 (30) | 8 (30) | 8 (30) | 8 (30) |
| 66 | 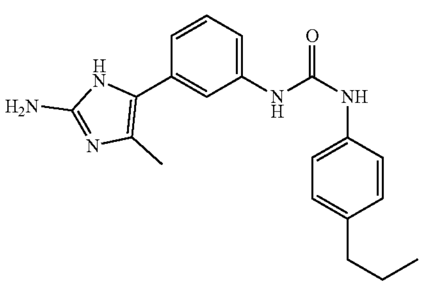 [SMILES: CCCc1ccc(NC(=O)Nc2cccc(-c3[nH]c(N)nc3C)c2)cc1] | 16 (7) | 16 (7) | 16 (7) | 8 (7) | 8 (7) | 4 (7) | 32 (30) | 128 (30) | 128 (30) | 8 (30) | 8 (30) | 16 (30) |

TABLE 1-continued

Minimal inhibitory concentration (MIC) values upon addition of compound

| Compound None | Structure | A. baumannii ATCC BAA-1605 | | | A. baumannii AB5075 | | | K. pneumoniae ATCC BAA-2146 | | | K pneumoniae ATCC BAA-1705 | | |
|---|---|---|---|---|---|---|---|---|---|---|---|---|---|
| | | I 32 | M 32 | D 32 | I 32 | M 32 | D 32 | I 128 | M 256 | D 256 | I 64 | M 64 | D 64 |
| 67 | [2-amino-5-methyl-1H-imidazol-4-yl-phenyl urea with 3,5-dibromophenyl] | 8 (15) 16 (7) | 4 (15) 16 (7) | 4 (15) 16 (7) | 4 (30) 8 (7) | 2 (30) 4 (7) | 4 (30) 4 (7) | 64 (7) | 128 (7) | 256 (7) | 32 (7) | 32 (7) | 64 (7) |
| 68 | [2-amino-5-methyl-1H-imidazol-4-yl-phenyl urea with 3-Cl-4-CF3-phenyl] | 4 (4) 32 (2) | 4 (4) 32 (2) | 4 (4) 32 (2) | 8 (4) 16 (2) | 4 (4) 32 (2) | 4 (4) 16 (2) | 32 (4) 128 (2) | 16 (4) 128 (2) | 64 (4) 256 (2) | 16 (4) 32 (2) | 16 (4) 32 (2) | 16 (4) 64 (2) |
| 69 | [2-amino-4,5-dihydro-naphthoimidazole urea with 3,4-dichlorophenyl] | 4 (15) | 4 (15) | 4 (15) | 8 (15) | 8 (15) | 8 (15) | 32 (15) | 32 (15) | 32 (15) | 16 (15) | 16 (15) | 32 (15) |
| 70 | [2-amino-4,5-dihydro-naphthoimidazole urea with 3-Cl-4-CF3-phenyl] | 8 (4) | 8 (4) | 8 (4) | 8 (4) | 8 (4) | 16 (4) | 128 (7) | 128 (7) | 128 (7) | 32 (7) | 32 (7) | 64 (7) |
| 71 | [2-amino-4,5-dihydro-naphthoimidazole urea with 3,5-dibromophenyl] | 8 (30) | 16 (30) | 16 (30) | 4 (30) | 4 (30) | 8 (30) | 16 (60) | 32 (60) | 32 (60) | 16 (15) | 8 (15) | 16 (15) |

TABLE 1-continued

Minimal inhibitory concentration (MIC) values upon addition of compound

| Compound None | Structure | MIC (μg/mL) (μM of 2-AI Compound Used) | | | | | | | | | | | |
|---|---|---|---|---|---|---|---|---|---|---|---|---|---|
| | | *A. baumannii* ATCC BAA-1605 | | | *A. baumannii* AB5075 | | | *K. pneumoniae* ATCC BAA-2146 | | | *K. pneumoniae* ATCC BAA-1705 | | |
| | | I | M | D | I | M | D | I | M | D | I | M | D |
| None | Structure | 32 | 32 | 32 | 32 | 32 | 32 | 128 | 256 | 256 | 64 | 64 | 64 |
| 72 | | 16 (7) | 8 (7) | 8 (7) | 4 (7) | 8 (7) | 4 (7) | 16 (60) | 32 (60) | 32 (60) | 16 (60) | 16 (60) | 16 (60) |
| 73 | | 16 (7) | 8 (7) | 8 (7) | 16 (7) | 8 (7) | 8 (7) | 64 (15) | 256 (15) | 128 (15) | 64 (15) | 64 (15) | 64 (15) |
| 74 | | 16 (60) | 16 (60) | 16 (60) | 16 (60) | 16 (60) | 16 (60) | 128 (60) | 256 (60) | 256 (60) | 64 (60) | 64 (60) | 64 (60) |
| 75 | | 8 (7) | 8 (7) | 8 (7) | 8 (7) | 8 (7) | 8 (7) | 16 (7) | 16 (7) | 16 (7) | 16 (7) | 8 (7) | 16 (7) |

TABLE 1-continued

Minimal inhibitory concentration (MIC) values upon addition of compound

| | | MIC (μg/mL) (μM of 2-AI Compound Used) | | | | | | | | | | |
|---|---|---|---|---|---|---|---|---|---|---|---|---|
| | | *A. baumannii* ATCC BAA-1605 | | | *A. baumannii* AB5075 | | | *K. pneumoniae* ATCC BAA-2146 | | | *K pneumoniae* ATCC BAA-1705 | | |
| Compound | Structure | I | M | D | I | M | D | I | M | D | I | M | D |
| None | | 32 | 32 | 32 | 32 | 32 | 32 | 128 | 256 | 256 | 64 | 64 | 64 |

The following compounds are 2-amino-4-phenyl imidazole derivatives with substitution on the N-1 nitrogen and a urea functionality on the 3-position of the phenyl ring.

| 76 | [structure] | 32 (60) | 32 (60) | 32 (60) | | | | 128 (60) | 256 (60) | 256 (60) | | | |

The following compounds are 2-amino-4-phenyl imidazole derivatives with a urea functionality on the 3-position of the phenyl ring and additional substitution on the amino group in the 2-position. Neither of these compounds showed activity.

| 77 | [structure] | 32 (60) | 32 (60) | 32 (60) | 32 (60) | 32 (60) | 32 (60) | 128 (60) | 256 (60) | 256 (60) | 64 (60) | 64 (60) | 64 (60) |
| 78 | [structure] | 32 (60) | 16 (60) | 32 (60) | 32 (60) | 32 (60) | 32 (60) | 128 (60) | 256 (60) | 256 (60) | 64 (60) | 64 (60) | 64 (60) |

The following compounds are 2-amino-4-phenyl imidazole derivatives with a urea functionality in the 3-position of the phenyl ring and an additional substituent in the 4-position of the phenyl ring.

| 79 | [structure] | 16 (7) | 16 (7) | 16 (7) | 8 (7) | 16 (7) | 8 (7) | 128 (7) | 256 (7) | 128 (7) | | | |

TABLE 1-continued

Minimal inhibitory concentration (MIC) values upon addition of compound

| | | MIC (µg/mL) (µM of 2-AI Compound Used) | | | | | | | | | | | |
|---|---|---|---|---|---|---|---|---|---|---|---|---|---|
| | | *A. baumannii* ATCC BAA-1605 | | | *A. baumannii* AB5075 | | | *K. pneumoniae* ATCC BAA-2146 | | | *K pneumoniae* ATCC BAA-1705 | | |
| Compound | Structure | I | M | D | I | M | D | I | M | D | I | M | D |
| None | | 32 | 32 | 32 | 32 | 32 | 32 | 128 | 256 | 256 | 64 | 64 | 64 |
| 80 | 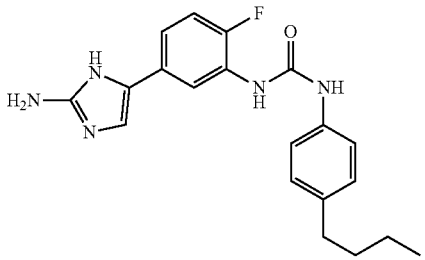 [SMILES: CCCCc1ccc(NC(=O)Nc2cc(-c3cnc(N)[nH]3)ccc2F)cc1] | 4 (7) 16 (4) | 4 (7) 16 (4) | 8 (7) 16 (4) | 8 (7) 8 (4) | 8 (7) 8 (4) | 4 (7) 8 (4) | 64 (15) | 128 (15) | 128 (15) | 64 (15) | 32 (15) | 64 (15) |
| 81 | 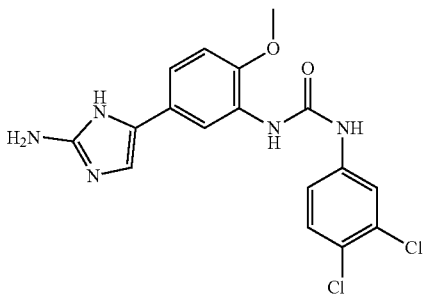 [SMILES: COc1ccc(-c2cnc(N)[nH]2)cc1NC(=O)Nc1ccc(Cl)c(Cl)c1] | 4 (60) 32 (15) | 4 (60) 32 (15) | 4 (60) 16 (15) | 4 (60) 16 (15) | 4 (60) 16 (15) | 4 (60) 16 (15) | 64 (60) | 256 (60) | 256 (60) | 64 (60) | 64 (60) | 64 (60) |
| 82 | 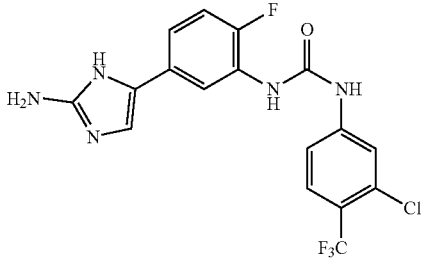 [SMILES: Nc1ncc(-c2ccc(F)c(NC(=O)Nc3ccc(C(F)(F)F)c(Cl)c3)c2)[nH]1] | 8 (15) | 8 (15) | 8 (15) | 4 (15) | 8 (15) | 2 (15) | 128 (15) | 256 (15) | 256 (15) | 64 (7) | 64 (7) | 64 (7) |

The following compound is a 2-amino-4-phenyl imidazole derivative with a urea functionality on the 3-position of the phenyl ring. The distal nitrogen of the urea has a phenyl ring on it and the proximal nitrogen of the urea contains a benzyl substituent. This additional substituent on the proximal nitrogen of the urea may be detrimental to activity.

| 83 | 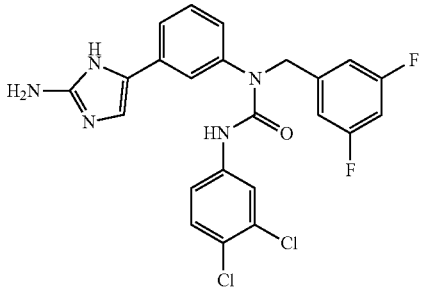 [SMILES: Nc1ncc(-c2cccc(N(Cc3cc(F)cc(F)c3)C(=O)Nc3ccc(Cl)c(Cl)c3)c2)[nH]1] | 16 (60) | 32 (60) | 16 (60) | 128 (60) | 256 (60) | 256 (60) | | | | | | |

TABLE 1-continued

Minimal inhibitory concentration (MIC) values upon addition of compound

| Compound | Structure | A. baumannii ATCC BAA-1605 MIC (µg/mL) (µM of 2-AI Compound Used) | | | A. baumannii AB5075 | | | K. pneumoniae ATCC BAA-2146 | | | K pneumoniae ATCC BAA-1705 | | |
|---|---|---|---|---|---|---|---|---|---|---|---|---|---|
| | | I | M | D | I | M | D | I | M | D | I | M | D |
| None | Structure | 32 | 32 | 32 | 32 | 32 | 32 | 128 | 256 | 256 | 64 | 64 | 64 |

The following compounds are 2-amino-4-phenyl imidazole derivatives with a urea functionality on the 3-position of the phenyl ring. The distal nitrogen of these ureas is di-substituted.

| 84 | [structure] | 8 (60) | 8 (60) | 8 (60) | 8 (60) | 4 (60) | 4 (60) | 128 (60) | 256 (60) | 256 (60) | | | |
| 85 | [structure] | 32 (7) | 32 (7) | 32 (7) | 8 (15) 32 (7) | 8 (15) 16 (7) | 4 (15) 32 (7) | 128 (15) | 256 (15) | 256 (15) | 64 (15) | 64 (15) | 64 (15) |

The following compounds are 2-amino-5-phenyl imidazole derivatives with substitution on N-1 of the imidazole ring. The 5-phenyl ring contains a urea functionality in the 3-position.

| 86 | [structure] | 16 (60) | 32 (60) | 32 (60) | 128 (60) | 256 (60) | 256 (60) | | | | | | |
| 87 | [structure] | 16 (60) | 32 (60) | 32 (60) | 128 (60) | 256 (60) | 256 (60) | | | | | | |
| 88 | [structure] | 4 (30) | 2 (30) | 4 (30) | 4 (60) 8 (30) | 4 (60) 8 (30) | 2 (60) 4 (30) | 128 (60) | 128 (30) | 128 (30) | | | |

TABLE 1-continued

Minimal inhibitory concentration (MIC) values upon addition of compound

| | MIC (µg/mL) (µM of 2-AI Compound Used) | | | | | | | | | | | |
|---|---|---|---|---|---|---|---|---|---|---|---|---|
| | *A. baumannii* ATCC BAA-1605 | | | *A. baumannii* AB5075 | | | *K. pneumoniae* ATCC BAA-2146 | | | *K. pneumoniae* ATCC BAA-1705 | | |
| Compound | I | M | D | I | M | D | I | M | D | I | M | D |
| None Structure | 32 | 32 | 32 | 32 | 32 | 32 | 128 | 256 | 256 | 64 | 64 | 64 |

The following compounds are 2-amino-4-phenyl derivatives with a urea functionality on the 3-position of the phenyl ring. These ureas contain an aliphatic substituent on the distal nitrogen of the urea. From this limited data set, it appears that an alkyl chain is slightly more active than the cyclic alkane.

| Compound | Structure | I | M | D | I | M | D | I | M | D | I | M | D |
|---|---|---|---|---|---|---|---|---|---|---|---|---|---|
| 89 | [structure] | 4 (60) | | | 8 (60) | 8 (60) | 2 (60) | 128 (60) | 256 (60) | 256 (60) | | | |
| 90 | [structure] | | | | 32 (60) | 32 (60) | 32 (60) | 128 (60) | 256 (60) | 256 (60) | | | |

The following compounds are 2-amino-4-phenyl thioureas with a substituted phenyl ring on the distal nitrogen of the thiourea. From the limited amount of data, these compounds appear to be slightly less active than the urea derivatives.

| Compound | Structure | I | M | D | I | M | D | I | M | D | I | M | D |
|---|---|---|---|---|---|---|---|---|---|---|---|---|---|
| 91 | [structure] | 8 (15) | 16 (15) | 8 (15) | 8 (30) 16 (15) | 4 (30) 8 (15) | 4 (30) 8 (15) | 128 (15) | 256 (15) | 256 (15) | | | |

These derivatives are urea compounds in which a 2-aminoimidazo functionality appears on each nitrogen of the urea. Some are symmetrical and some are not.

| Compound | Structure | I | M | D | I | M | D | I | M | D | I | M | D |
|---|---|---|---|---|---|---|---|---|---|---|---|---|---|
| 92 | [structure] | 4 (10) 16 (7) | 4 (10) 16 (7) | 8 (10) 8 (7) | 4 (15) 8 (10) | 4 (15) 4 (10) | 8 (15) 8 (10) | 128 (30) 128 (10) | 128 (30) 256 (10) | 256 (30) 256 (10) | 64 (30) 64 (10) | 32 (30) 32 (10) | 64 (30) 64 (10) |
| 93 | [structure] | 6 (15) | 2 (30) 4 (15) | 4 (15) | 3 (30) 8 (15) 16 (5) | 3 (30) 4 (15) 32 (5) | 3 (30) 4 (15) 16 (5) | 128 (60) | 128 (60) | 128 (60) | 32 (60) | 16 (60) | 24 (60) |
| 94 | [structure] | 4 (15) 16 (10) 16 (7) | 4 (15) 8 (10) 16 (7) | 4 (15) 8 (10) 16 (7) | 4 (15) 8 (10) 16 (7) | 2 (15) 4 (10) 16 (7) | 2 (15) 4 (10) 8 (7) | 128 (60) | 128 (60) | 128 (60) | 64 (60) | 64 (60) | 64 (60) |

TABLE 1-continued

Minimal inhibitory concentration (MIC) values upon addition of compound

| Compound | Structure | A. baumannii ATCC BAA-1605 MIC (µg/mL) (µM of 2-AI Compound Used) | | | A. baumannii AB5075 | | | K. pneumoniae ATCC BAA-2146 | | | K pneumoniae ATCC BAA-1705 | | |
|---|---|---|---|---|---|---|---|---|---|---|---|---|---|
| | | I | M | D | I | M | D | I | M | D | I | M | D |
| None | | 32 | 32 | 32 | 32 | 32 | 32 | 128 | 256 | 256 | 64 | 64 | 64 |
| 95 | (structure) | 1 (30) | 2 (30) | 2 (30) | 3 (60) | 2 (60) | 2 (60) | 64 (60) | 64 (60) | 64 (60) | 64 (60) | 32 (60) | 32 (60) |
| | | 8 (15) | 8 (15) | 6 (15) | 4 (30) | 2 (30) | 3 (30) | | | | | | |
| | | 16 (10) | 16 (10) | 8 (10) | 8 (15) | 4 (15) | 4 (15) | | | | | | |
| | | | | | 8 (10) | 8 (10) | 8 (10) | | | | | | |
| 96 | (structure) | 2 (15) | 4 (15) | 2 (15) | 2 (15) | 2 (15) | 2 (15) | 128 (30) | 256 (30) | 128 (30) | 64 (15) | 32 (15) | 64 (15) |
| | | 4 (7) | 4 (7) | 4 (7) | 8 (7) | 4 (7) | 4 (7) | | | | | | |
| 97 | (structure) | 8 (2) | 4 (2) | 2 (2) | 4 (4) | 2 (4) | 2 (4) | 64 (60) | 128 (60) | 128 (60) | 64 (60) | 32 (60) | 32 (60) |
| | | | | | 16 (2) | 16 (2) | 8 (2) | | | | | | |
| 98 | (structure) | 8 (4) | 4 (4) | | 4 (4) | 4 (4) | | 128 (60) | 256 (60) | 256 (60) | 64 (60) | 64 (60) | 64 (60) |

EXAMPLE 2: Six compounds were assessed for their activity in combination with meropenem against carbapenem resistant strains of *A. baumannii* (Ab), *K. pneumoniae* (Kp), and *E. coli* acquired from the Center for Disease Control (CDC). AR #—assigned AR-BANK number from the CDC.

TABLE 2

MIC values according to compounds.

| Cpd | Structure | Minimum Inhibitory Concentration of Meropenem (μg/mL) (μM of 2-amino imidazole Compound used) | | | | | | | | | | | | | | | | |
|---|---|---|---|---|---|---|---|---|---|---|---|---|---|---|---|---|---|---|
| | | Ab AR# 33 | Ab AR# 35 | Ab AR# 36 | Ab AR# 37 | Ab AR# 45 | Ab AR# 52 | Ab AR# 56 | Ab AR# 63 | Ab AR# 70 | Ab AR# 83 | Ab AR# 88 | Kp AR# 40 | Kp AR# 41 | Kp AR# 68 | Kp AR# 98 | E. coli AR# 48 | E. coli AR# 55 |
| None | | 128 | 128 | 128 | 256 | 16 | 8 | 32 | 128 | 8 | 256 | 512 | 1024 | 64 | 512 | 128 | 256 | 256 |
| 2 | 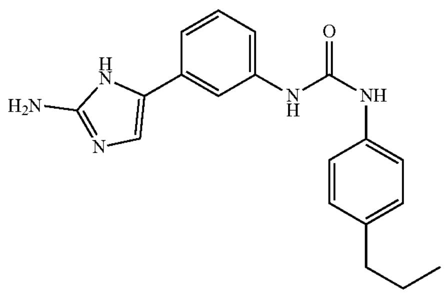 [SMILES: CCCc1ccc(NC(=O)Nc2cccc(-c3cnc(N)[nH]3)c2)cc1] | 32 (15) | 16 (15) | 4 (30) | 64 (15) | 1.5 (15) | 1.5 (15) | 8 (15) | 8 (30) | 2 (7) | 96 (15) | 128 (15) | 1024 (64) | 32 (64) | 256 (32) | 64 (64) | 128 (64) | 64 (64) |
| 92 | 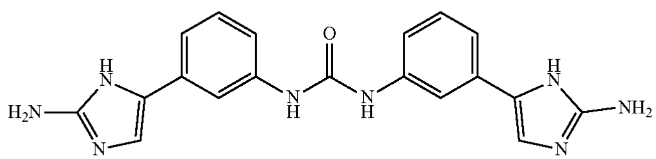 [SMILES: Nc1ncc(-c2cccc(NC(=O)Nc3cccc(-c4cnc(N)[nH]4)c3)c2)[nH]1] | 12 (15) | 8 (30) | 4 (15) | 32 (15) | 2 (7) | 2 (2) | 8 (15) | 8 (7) | 4 (2) | 64 (15) | 64 (15) | 256 (60) | 64 (60) | 64 (30) | 64 (60) | 256 (7) | 128 (15) |
| 7 | 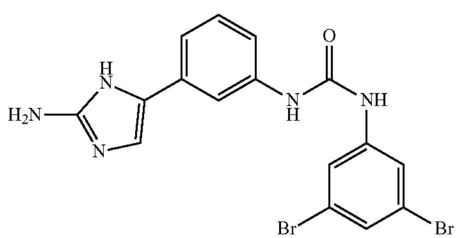 [SMILES: Nc1ncc(-c2cccc(NC(=O)Nc3cc(Br)cc(Br)c3)c2)[nH]1] | 16 (15) | 32 (30) | 8 (7) | 32 (7) | 1 (15) | 2 (4) | 8 (15) | 32 (4) | 4 (2) | 24 (15) | 64 (15) | 64 (15) | 8 (15) | 128 (7) | 64 (7) | 64 (15) | 64 (15) |

TABLE 2-continued

MIC values according to compounds.

| Cpd None | Structure | Minimum Inhibitory Concentration of Meropenem (µg/mL) (µM of 2-amino imidazole Compound used) | | | | | | | | | | | | | |
|---|---|---|---|---|---|---|---|---|---|---|---|---|---|---|
| | | Ab AR# 33 | Ab AR# 35 | Ab AR# 36 | Ab AR# 37 | Ab AR# 45 | Ab AR# 52 | Ab AR# 56 | Ab AR# 63 | Ab AR# 70 | Ab AR# 83 | Ab AR# 88 | Kp AR# 40 | Kp AR# 41 | Kp AR# 68 | Kp AR# 98 | E. coli AR# 48 | E. coli AR# 55 |
| 93 | [structure] | 128 (7) | 32 (15) | 16 (15) | 64 (7) | 2 (7) | 3 (4) | 16 (15) | 8 (15) | 1 (7) | 64 (15) | 64 (7) | 1024 (64) | 8 (64) | 32 (32) | 32 (32) | 256 | 128 (16) |
| 68 | [structure] | 64 (4) | 64 (4) | 48 (4) | 64 (4) | 3 (4) | 4 (4) | 4 (4) | 128 (2) | 1 (4) | 64 (4) | 64 (7) | 64 (7) | 64 (4) | 128 (7) | 32 (7) | 128 (4) | 64 (4) |
| 97 | [structure] | 4 (16) | 2 (8) | 1 (8) | 32 (8) | 1 (8) | 2 (2) | 2 (8) | 8 (8) | 0.5 (8) | 16 (8) | 32 (16) | 1024 (64) | 16 (64) | 64 (32) | 32 (16) | 128 (16) | 256 (32) |

The foregoing is illustrative of the present invention, and is not to be construed as limiting thereof. The invention is defined by the following claims, with equivalents of the claims to be included therein.

That which is claimed is:

1. A compound of Formula (I):

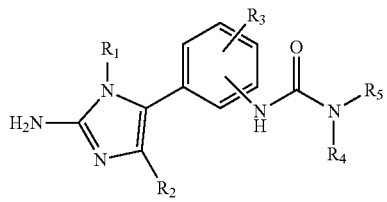

(I)

wherein:
R$_1$ is selected from the group consisting of H and lower alkyl;
R$_2$ is selected from the group consisting of H, lower alkyl, aryl, and heteroaryl;
R$_3$ is selected from the group consisting of H, halo and alkoxy;
or R$_2$ and R$_3$ together form a fused ring; and
R$_4$ and R$_5$ are each independently selected from the group consisting of H, alkyl, aryl, cycloalkyl, heterocyclo, and heteroaryl,
or a pharmaceutically acceptable salt or prodrug thereof.

2. The compound of claim 1, wherein said compound is a compound of Formula (I)(a):

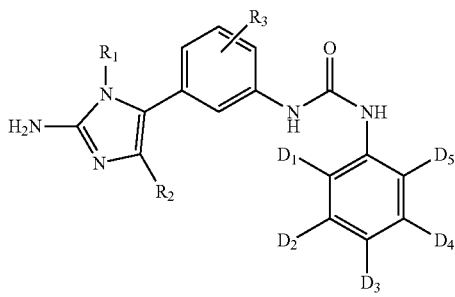

(I)(a)

wherein:
R$_1$, R$_2$ and R$_3$ are as defined above, and
D$_1$, D$_2$, D$_3$, D$_4$, and D$_5$ are each independently selected from the group consisting of H, halo, alkyl, acyl, alkoxy, aryl, heteroaryl, amino, amide, nitro, hydroxyl, thiol, sulfone, sulfoxide, nitrile, nitro, and haloalkyl,
or wherein D$_1$ and D$_2$, D$_2$ and D$_3$, D$_3$ and D$_4$, or D$_4$ and D$_5$ together form a fused ring, optionally substituted,
or a pharmaceutically acceptable salt or prodrug thereof.

3. The compound of claim 2, wherein at least one of D$_1$, D$_2$, D$_3$, D$_4$, and D$_5$ is lower alkyl,
or a pharmaceutically acceptable salt thereof.

4. The compound of claim 2, wherein D$_3$ is lower alkyl,
or a pharmaceutically acceptable salt thereof.

5. The compound of claim 4, wherein D$_3$ is n-propyl or n-butyl,
or a pharmaceutically acceptable salt thereof.

6. The compound of claim 5, wherein said compound is a compound of Formula (I)(a)(1):

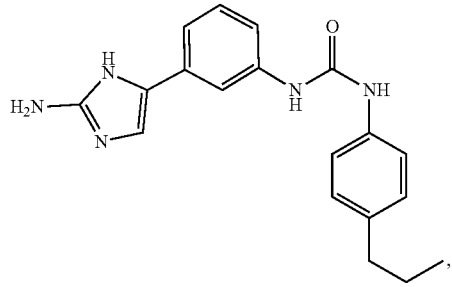

(I)(a)(1)

or a pharmaceutically acceptable salt thereof.

7. The compound of claim 2, wherein at least one of D$_1$, D$_2$, D$_3$, D$_4$, and D$_5$ is heteroaryl,
or a pharmaceutically acceptable salt thereof.

8. The compound of claim 2, wherein D$_2$ is heteroaryl,
or a pharmaceutically acceptable salt thereof.

9. The compound of claim 8, wherein D$_2$ is 2-amino imidazole,
or a pharmaceutically acceptable salt thereof.

10. The compound of claim 9, wherein said compound is a compound of Formula (I)(a)(2):

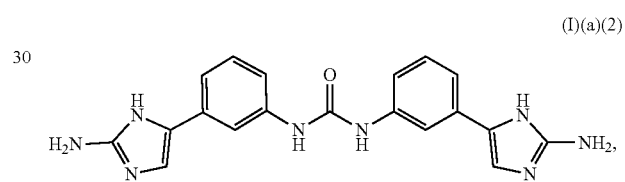

(I)(a)(2)

or a pharmaceutically acceptable salt thereof.

11. The compound of claim 2, wherein at least one of D$_1$, D$_2$, D$_3$, D$_4$, and D$_5$ is halo,
or a pharmaceutically acceptable salt thereof.

12. The compound of claim 2, wherein D$_2$ and D$_4$ are each halo,
or a pharmaceutically acceptable salt thereof.

13. The compound of claim 12, wherein D$_2$ and D$_4$ are each Br,
or a pharmaceutically acceptable salt thereof.

14. The compound of claim 13, wherein said compound is a compound of Formula (I)(a)(3):

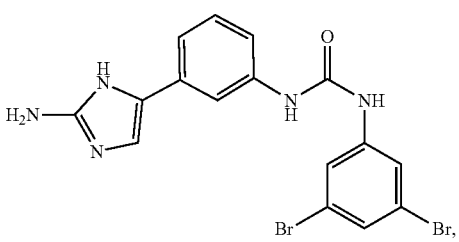

(I)(a)(3)

or a pharmaceutically acceptable salt thereof.

15. The compound of claim 2, wherein:
at least one of D$_1$, D$_2$, D$_3$, D$_4$, and D$_5$ is halo; and
at least one of D$_1$, D$_2$, D$_3$, D$_4$, and D$_5$ is haloalkyl,
or a pharmaceutically acceptable salt thereof.

16. The compound of claim 15, wherein $D_3$ is fluoroalkyl, and $D_4$ is halo,
or a pharmaceutically acceptable salt thereof.

17. The compound of claim 16, wherein $D_3$ is trifluoromethyl, and $D_4$ is Cl,
or a pharmaceutically acceptable salt thereof.

18. The compound of claim 17, wherein $R_2$ is lower alkyl,
or a pharmaceutically acceptable salt thereof.

19. The compound of claim 18, wherein said compound is a compound of Formula (I)(a)(4):

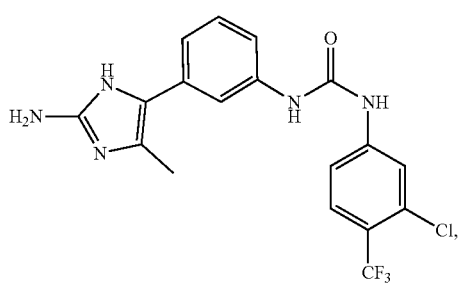

(I)(a)(4)

or a pharmaceutically acceptable salt thereof.

20. The compound of claim 1, wherein said compound is a compound of Formula (I)(b):

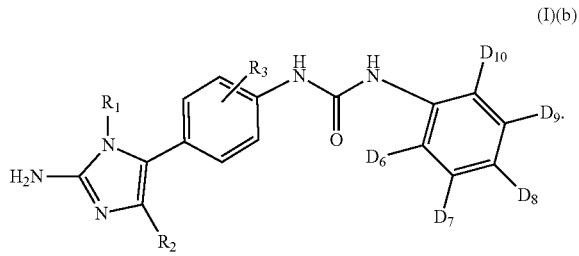

(I)(b)

wherein:
$R_1$, $R_2$ and $R_3$ are as defined above, and
$D_6$, $D_7$, $D_8$, $D_9$, and $D_{10}$ are each independently selected from the group consisting of H, halo, alkyl, acyl, alkoxy, aryl, heteroaryl, amino, amide, nitro, hydroxyl, thiol, sulfone, sulfoxide, nitrile, nitro, and haloalkyl,
or wherein $D_6$ and $D_7$, $D_7$ and $D_8$, $D_8$ and $D_9$, or $D_9$ and $D_{10}$ together form a fused ring,
or a pharmaceutically acceptable salt thereof.

21. The compound of claim 20, wherein at least one of $D_6$, $D_7$, $D_8$, $D_9$, and $D_{10}$ is heteroaryl,
or a pharmaceutically acceptable salt thereof.

22. The compound of claim 21, wherein $D_8$ is heteroaryl,
or a pharmaceutically acceptable salt thereof.

23. The compound of claim 22, wherein $D_8$ is 2-amino imidazole,
or a pharmaceutically acceptable salt thereof.

24. The compound of claim 23, wherein said compound is a compound of Formula (I)(b)(1):

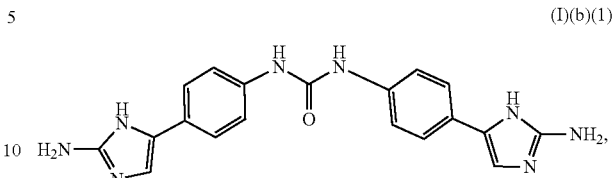

(I)(b)(1)

or a pharmaceutically acceptable salt thereof.

25. The compound of claim 20, wherein $D_8$ and $D_9$ together form a fused ring, optionally substituted,
or a pharmaceutically acceptable salt thereof.

26. The compound of claim 25, wherein $D_8$ and $D_9$ form a cyclohexane or cyclohexene fused ring, optionally substituted,
or a pharmaceutically acceptable salt thereof.

27. The compound of claim 26, wherein said compound is a compound of Formula (I)(b)(2):

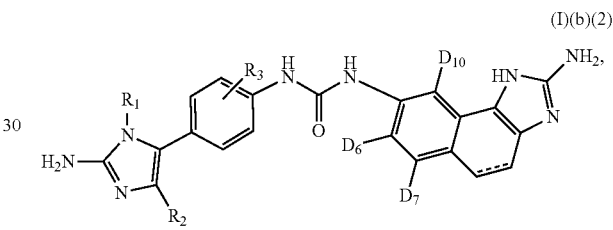

(I)(b)(2)

or a pharmaceutically acceptable salt thereof.

28. The compound of claim 27, said compound is a compound of Formula (I)(b)(3):

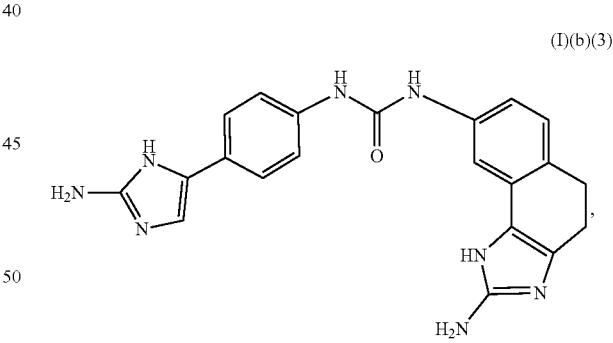

(I)(b)(3)

or a pharmaceutically acceptable salt thereof.

29. A composition comprising a carrier and an effective amount of the compound of claim 1.

30. The composition of claim 29, wherein said composition is formulated for topical use.

31. The composition of claim 29, wherein said composition is an ointment, cream, lotion, paste, gel, spray, aerosol, or oil.

32. A composition comprising the compound of claim 1 covalently coupled to a substrate.

33. A coating composition, comprising:
(a) a film-forming resin;
(b) a solvent that disperses said resin;

(c) an effective amount of the compound of claim 1, wherein said effective amount of said compound enhances the effects of an antibiotic that is administered in combination with the compound; and (d) optionally, at least one pigment.

34. The coating composition of claim 33, wherein said compound is covalently coupled to said resin.

35. The coating composition of claim 33, wherein said resin comprises a polymeric material.

36. A substrate coated with the coating composition of claim 33.

37. A method of reducing microbial growth on a substrate comprising the step of contacting the compound of claim 1 to said substrate in an amount effective to enhance the effects of an antibiotic that is administered in combination with the compound.

38. The method of claim 37, wherein said microbial growth is Gram-negative bacterial growth.

39. The method of claim 38, wherein said bacterial growth is *Acinetobacter baumannii, Klebsiella pneumoniae*, or *Escherichia coli*.

40. The method of claim 38, wherein said bacterial growth is carbapenem resistant strains of *Acinetobacter baumannii, Klebsiella pneumoniae*, or *Escherichia coli*.

41. A method for treating a bacterial infection in a subject in need thereof, comprising administering to said subject the compound of claim 1 in an amount effective to enhance the effects of an antibiotic that is administered in combination with the compound.

42. The method of claim 41, wherein said bacterial infection comprises Gram-negative bacteria.

43. The method of claim 41, wherein said bacterial infection comprises *Acinetobacter baumannii, Klebsiella pneumoniae*, or *Escherichia coli*.

44. The method of claim 41, wherein said bacterial infection comprises carbapenem resistant strains of *Acinetobacter baumannii, Klebsiella pneumoniae*, or *Escherichia coli*.

45. The method of claim 41, wherein a biocide is administered to said subject in combination with the compound.

46. The method of claim 45, wherein the compound is administered to said subject in an amount effective to enhance the effects of the biocide.

47. A medical device comprising:

(a) a medical device substrate; and (b) an effective amount of the compound of claim 1, either coating the substrate, or incorporated into the substrate, wherein said effective amount of said compound enhance the effects of an antibiotic that is administered in combination with the compound.

48. The medical device of claim 47, wherein said medical device substrate is selected from the group consisting of stents, fasteners, ports, catheters, scaffolds and grafts.

49. The medical device of claim 47, wherein said compound is covalently coupled to said substrate.

* * * * *